US008044044B2

(12) United States Patent
Hubschwerlen et al.

(10) Patent No.: US 8,044,044 B2
(45) Date of Patent: Oct. 25, 2011

(54) 4-(1-AMINO-ETHYL)-CYCLOHEXYLAMINE DERIVATIVES

(75) Inventors: Christian Hubschwerlen, Durmenach (FR); Georg Rueedi, Allschwil (CH); Jean-Philippe Surivet, Kembs (FR); Cornelia Zumbrunn-Acklin, Basel (CH)

(73) Assignee: Actelion Pharmaceutical Ltd., Allschwil (CH)

( * ) Notice: Subject to any disclaimer, the term of this patent is extended or adjusted under 35 U.S.C. 154(b) by 150 days.

(21) Appl. No.: 12/520,580

(22) PCT Filed: Dec. 21, 2007

(86) PCT No.: PCT/IB2007/055281
§ 371 (c)(1),
(2), (4) Date: Jun. 22, 2009

(87) PCT Pub. No.: WO2008/078305
PCT Pub. Date: Jul. 3, 2008

(65) Prior Publication Data
US 2010/0029623 A1    Feb. 4, 2010

(30) Foreign Application Priority Data

Dec. 22, 2006   (WO) .................. PCT/IB2006/055026
Jul. 13, 2007   (WO) .................. PCT/IB2007/052805

(51) Int. Cl.
*A61K 31/542*    (2006.01)
*A61K 31/5415*   (2006.01)
(52) U.S. Cl. ......... 514/224.2; 514/300; 544/48; 544/51; 544/105; 546/122
(58) Field of Classification Search .................... 546/122
See application file for complete search history.

(56) References Cited

U.S. PATENT DOCUMENTS 5,536,725 A    7/1996   Cullen et al.

FOREIGN PATENT DOCUMENTS

| WO | WO 00/24717    | 5/2000 |
|----|----------------|--------|
| WO | WO 03/051887   | 6/2003 |
| WO | WO 03/087098   | 10/2003 |
| WO | WO 2004/002992 | 1/2004 |
| WO | WO 2004/035569 | 4/2004 |
| WO | WO 2004/058144 | 7/2004 |
| WO | WO 2006/021448 | 3/2006 |
| WO | WO 2006/032466 | 3/2006 |
| WO | WO 2006/046552 | 5/2006 |
| WO | WO 2006/093253 | 9/2006 |

OTHER PUBLICATIONS

Blakemore, P., "The Modified Julia Olefination: Alkene Synthesis via the Condensation of Metallated Hetroarylalkylsulfones with Carbonyl Compounds", Journal Chem. Soc., Perkin Trans. 1 (2002), 2563-2585 28.

Corey, E. J. et al., A Synthetic Method for Formyl-Ethynyl Conversion (RCHO RC=CH or RC=CR) Tetrahedron Letters (1972), No. 36, 3769-3772.

DeLoux, L. and Srebnik, M., "Asymmetric Boron-Catalyzed Reactions", Chem. Rev. (1993), 93, 763-764, 15.

Dess, D. et al., "A Useful 12-I-5 Triacetoxyperiodinane (the Dess-Martin Periodinane) for the Selective Oxidation of Primary or Secondary Alcohols and a Variety of Related 12-I-5 Species", Journal American Chemical Society (1991), 113, pp. 7277-7287.

Echavarren, A., "Palladium-Catalyzed Coupling of Aryl Triflates with Organostannanes", Journal of American Chemical Soc. (1987), 109, 5478 32.

Fukuyama, T., 2-and 4 Nitrobenzenesulfamides Exceptionally Versatile Means for Preparation of Secondary Amines and Protection of Amines, Tetrahedron Letters (1995), vol. 36, 6373.

Gould, P., "Salt Selection for Basic Drugs", International Journal of Pharmaceutics, (1986), 33, pp. 201-217.

Greene, T.W., "Protection for the Amino Group", Protecting Groups in Organic Synthesis, $3^{rd}$ Ed (1999), pp. 494-653.

Greene, T.W., "Protection for the Carboxyl Group", Protecting Groups in Organic Synthesis 3rd Ed; 1999, 369 441; T.W. Greene, P.G.M. Wuts.

Hanessian, S. et al., "Generation of Functional Diversity Via Nitroaldol Condensations of α-Aminaacid Aldehydes—A New and Stereocontrolled Route to Acyclic 1,3-Diamino-2-Alcohols", Tetrahedron Letters, vol. 37, No. 7, pp. 987-990, (1996).

Heck, R., "Palladium-Catalyzed Vinylation of Organic Halides", Org. Resct. (1982), 27, 345-390.

Hodgson, D.M. et al., "Extended Scope of Dirhodium (II)-Catalysed Enantioselective Intramolecular 1,3-Dipolar Cycloadditions of Carbonyl Ylides with Alkene and Alkyne Dipolarophiles", Synlett (2003), 59-62.

Itagaki, N., "Organocatalytic Entry to Chiral Bicyclo [3.n.1] Alkanones via Direct Asymmetric Intramolecular Aldolization" Organic Letters (2005), 7, 4185.

Kolb, H. et al., "Catalytic Asymmetric Dihydroxylation", Chemical Review (1994), vol. 94, pp. 2483-2547.

Ley, S. et al., "Tetrapropylammonium Perruthenate, Pr4 N+RuO4, TPAP: Catalytic Oxidant for Organic Synthesis", Synthesis, (1994), 7, 639-666.

(Continued)

*Primary Examiner* — James O Wilson
*Assistant Examiner* — Brian McDowell
(74) *Attorney, Agent, or Firm* — Hunton & Williams LLP

(57) ABSTRACT

The invention relates to compounds of formula (I) wherein $R^0$ represents H or OH; $R^1$ represents alkoxy; U and W represent N, V represents CH and $R^2$ represents H or F, or U and V represent CH, W represents N and $R^2$ represents H or F, or U and V represent N, W represents CH and $R^2$ represents H, or U represents N, V represents CH, W represents $CR^a$ and $R^2$ represents H; $R^a$ represents $CH_2OH$ or alkoxycarbonyl; A represents the group CH=CH—B or a binuclear heterocyclic system D, B representing a mono- or di-substituted phenyl group wherein the substituents are halogen atoms and D representing one of the following groups wherein Z represents CH or N, and Q represents O or S; and to salts of such compounds. These compounds are useful as antibacterial agents.

8 Claims, No Drawings

OTHER PUBLICATIONS

Luzzio, F., The Henry Reaction: Recent Examples, Tetrahedron Letters vol. 57, 915-945, (2001).

Meijere, A. and Meyer, F., "Fine Feathers Make Fine Birds: The Heck Reaction in Modern Garb", Angew. Chem. Int. Ed. Engl. (1994), 33 (23-24), 2379-2411.

Mitsunobu, O., "The Use of Diethyl Azodicarboxylate and Triphenylphosphine in Syntersis and Transformation of Natural Products", Synthesis (1981), 165.

Muller, S. et al., "An Improved One-Pot Procedure for the Synthesis of Alkynes from Aldehydes", Synlett (1996), 521-522.

Ohira, S., "Methanolysis of Dimethyl (1-Diazo-2-Oxopropyl) Phosphonate: Generation of Dimethyl (Diazomethyl) Phosphonate and Reaction with Carbonyl Compounds", Synthetic Communications, (1989), vol. 19, 561-564.

Sato, S. et al., "One-Pot Reductive Amination of Aldehydes and Ketones with α-Picoline-Borane in Methanol, in Water, and in Neat Conditions", Tetrahedron Letters (2004), vol. 60,7899-7906.

Schultz, H., New Catalysts for the Oxidation of Sulfides to Sulfones with Hydrogen Peroxide, Journal of Organic Chemistry (1963), vol. 28, 1140.

Shioiri, T., "Degradation Reactions", Comprehensive Organic Synthesis; Trost, B. M., Fleming, I., Eds.; Pergamon: Oxford, 1991; vol. 6, p. 795.

Sonogashira, K. in Metal-Catalyzed Cross Coupling Reactions, Diedrich, F., Stang, P.J., Eds; Wiley-VCH: New York 1998.

Suggs, J.W., "Facile Synthesis of 8-Substituted Quinolines", Journal of Organic Chemistry (1980), 45,1514.

Talbot, G., "Bad Bugs Need Drugs: An Update on the Development Pipeline from the Antimicrobal Availability Task Force of the Infectious Diseases Society of America", Clinical Infectious Diseases (2006); (42) 657-68.

Trost, B. et al., "Chemoselective Oxidation of Sulfides to Sulfones with Potassium Hydrogen Persulfate", Tetrahedron Letters, vol. 22, No. 4, (1981), 1287-1290.

Trost, B. et al., Asymmetric Alkylation of Nitroalkanes, Angew Chern. Int. Ed. (2000), 3122-3124.

Wadsworth, W. et al., "The Utility of Phosphonate Carbanions in Olefin Synthesis", Journal of the American Chemical Soc. (1961), vol. 83,1733 1 B.

Wright, S. et al., Convenient Preparations of T-Butyl Esters and Ethers from T-Butanol, Tetrahedron Letters, vol. 38, No. 42, pp. 7345-7348, (1997).

Zhang, H.X. et al., Palladium and Molybdenum Catalyzed Hydrostannation of Alkynes a Novel Access to Regio and Stereodefined Vinylstannanes, Journal of Organic Chemistry (1990), vol. 55, 1B57.

International Search Report for Application No. PCT/IB2007/055281 mailed Jun. 19, 2008.

Greene et al., Protective Groups in Organic Synthesis, 3rd Edition, pp. 17-245, particularly pp. 23-147, 133-139 and 142-143 (Publisher: John Wiley and Sons, Inc., New York, N.Y.) (1999).

Siegel, et al., Heterogeneous Catalytic Hydrogenation of C=C and C=C, University of Arkansas, Fayetteville, AR, Pergamon Press: New York, vol. 8, pp. 417-488 (1991).

Troy et al., Index of Remington: The Science and Practice of Pharmacy, 21st Edition, published by Lippincott Williams & Wilkins (2005).

4-(1-AMINO-ETHYL)-CYCLOHEXYLAMINE DERIVATIVES

CROSS-REFERENCE TO RELATED APPLICATIONS

This application is the national phase application of PCT/IB2007/055281, filed Dec. 21, 2007, which claims the benefit of PCT/IB2006/055026, filed Dec. 22, 2006 and PCT/2007/052805, filed Jul. 13, 2007, the contents of all of which are hereby incorporated by reference as if fully set forth herein.

FIELD OF THE INVENTION

The present invention concerns novel 4-(1-amino-ethyl)-cyclohexylamine derivatives, pharmaceutical antibacterial compositions containing them and the use of these compounds in the manufacture of a medicament for the treatment of infections (e.g. bacterial infections). These compounds are useful antimicrobial agents effective against a variety of human and veterinary pathogens including among others Gram positive and Gram negative aerobic and anaerobic bacteria and mycobacteria.

BACKGROUND OF THE INVENTION

The intensive use of antibiotics has exerted a selective evolutionary pressure on micro-organisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:

- *S. aureus* is resistant to β-lactams, quinolones and now even to vancomycin;
- *S. pneumoniae* is becoming resistant to penicillin or quinolone antibiotics and even to new macrolides;
- *Enteroccocci* are quinolone and vancomycin resistant and β-lactam antibiotics are inefficacious against these strains;
- Enterobacteriacea are cephalosporin and quinolone resistant;
- *P. aeruginosa* are β-lactam and quinolone resistant.

Furthermore, the incidence of multi-drug-resistant Gram negative strains such as Enterobacteriacea and *Pseudomonas aeruginosa*, is steadily increasing and new emerging organisms like *Acinetobacter* spp. and *C. difficile*, which have been selected during therapy with the currently used antibiotics, are becoming a real problem in hospital settings. Therefore, there is a high medical need for new antibacterial agents which overcome multidrug-resistant gram-negative bacilli such as *A. baumannii*, ESBL-producing *E. coli* and *Klebsiella* species and *Pseudomonas aeruginosa* (*Clinical Infectious Diseases* (2006); 42657-68).

In addition, microorganisms that are causing persistent infections are increasingly being recognized as causative agents or cofactors of severe chronic diseases like peptic ulcers or heart diseases.

WO 03/087098 discloses, among others, compounds of the general formula (A1)

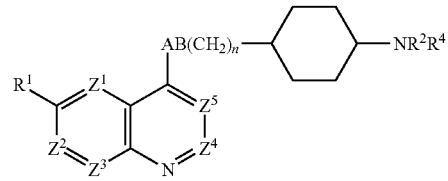

(A1)

wherein
one of $Z^1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH;

$R^1$ and $R^{1a}$ can notably be independently selected from hydrogen, halogen and $C_1$-$C_6$ alkoxy, provided that when $Z^1$, $Z^2$, $Z^3$, $Z^4$ and $Z^5$ are $CR^{1a}$ or CH, then $R^1$ is not hydrogen;

n is 0 or 1 and AB can notably represent a $CR^6R^7$—$CR^8R^9$ radical wherein each of $R^6$, $R^7$, $R^8$ and $R^9$ is independently selected from. H; $(C_{1-6})$alkoxy; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl which may be substituted; $(C_{2-6})$alkenylsulphonyl; or $(C_{1-6})$aminosulphonyl wherein the amino group is optionally substituted by $(C_{1-6})$ alkyl or $(C_{2-6})$alkenyl; or $R^6$ and $R^8$ together represent a bond and $R^7$ and $R^9$ are as above defined;

$R^2$ can be hydrogen, and
$R^4$ can be a group —U—$R^5_2$ in which $R^5_2$ is an optionally substituted bicyclic carbocyclic or heterocyclic ring system (A)

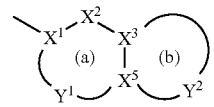

(A)

containing up to four heteroatoms in each ring in which at least one of rings (a) and (b) is aromatic, $X^1$ is C or N when part of an aromatic ring or $CR^{14}$ when part of a non aromatic ring;

$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;

$X^3$ and $X^5$ are independently N or C;

$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring, $Y^2$ is a 2 to 6 atom linker group, each atom of $Y^2$ being independently selected from N, $NR^{13}$, O, $S(O)_x$, CO and $CR^{14}$ when part of an aromatic or non-aromatic ring or may additionally be $CR^{14}R^{15}$ when part of a non aromatic ring;

each $R^{13}$ can notably be hydrogen;
each of $R^{14}$ and $R^{15}$ can notably be hydrogen;
each x is independently 0, 1 or 2;
U is CO, $SO_2$ or $CH_2$; or
$R^4$ can also be a group —$X^{1a}$—$X^{2a}$—$X^{3a}$—$X^{4a}$ wherein the group $X^{1a}$—$X^{2a}$—$X^{3a}$ can notably be $CH_2CH$=CH or COCH=CH and $X^{4a}$ can notably be a phenyl substituted one to three times wherein the substituents are notably selected from halogen atoms;

which compounds of formula (A1) can be used as antibacterials.

WO 2004/002992 discloses, among others, compounds of the general formula (A2)

(A2)

$$\left(\begin{matrix} Z^1 \\ Z^5-Z^4 \\ Z^2 \end{matrix} \begin{matrix} (x) \\ (y) \end{matrix} Z^3 \right) - AB(CH_2)_n - \underset{}{\bigcirc} - NR^2R^4$$

wherein
both rings (x) and (y) can be aromatic,
$Z^1$ can be a 3 atom linker group each atom of which can be independently selected from N and CH,
$Z^2$ can be a 3 atom linker group each atom of which can be independently selected from N and CH,
$Z^3$ can be CH,
$Z^4$ and $Z^5$ can both be carbon atoms,
n is 0 or 1 and AB represents notably a $CR^6R^7$—$CR^8R^9$ radical wherein each of $R^6$, $R^7$, $R^8$ and $R^9$ is independently selected from. H; ($C_{1-6}$)alkoxy; ($C_{1-6}$)alkylthio; halo; trifluoromethyl; azido; ($C_{1-6}$)alkyl; ($C_{2-6}$)alkenyl; ($C_{1-6}$)alkoxycarbonyl; ($C_{1-6}$)alkylcarbonyl; ($C_{2-6}$)alkenyloxycarbonyl; ($C_{2-6}$)alkenylcarbonyl; hydroxy, amino or aminocarbonyl which may be substituted; ($C_{2-6}$)alkenylsulphonyl; or ($C_{1-6}$) aminosulphonyl wherein the amino group is optionally substituted by ($C_{1-6}$) alkyl or ($C_{2-6}$)alkenyl; or $R^6$ and $R^8$ together represent a bond and $R^7$ and $R^9$ are as above defined;
$R^2$ can be hydrogen, and
$R^4$ can be a group —U—$R^5{}_2$ wherein U can be $CH_2$ and $R^5{}_2$ is an optionally substituted bicyclic carbocyclic or heterocyclic ring system (A)

(A)

$$\overset{X^1}{\underset{Y^1}{\diagdown}}\overset{X^2}{\underset{X^5}{\diagup}}\overset{X^3}{\underset{Y^2}{\diagdown}}$$

containing up to four heteroatoms in each ring in which at least one of rings (a) and (b) is aromatic,
$X^1$ is C or N when part of an aromatic ring or $CR^{14}$ when part of a non aromatic ring;
$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;
$X^2$ is N, $NR^{13}$, O, $S(O)_x$, CO or $CR^{14}$ when part of an aromatic or non-aromatic ring or may in addition be $CR^{14}R^{15}$ when part of a non aromatic ring;
$Y^1$ is a 0 to 4 atom linker group each atom of which is independently selected from N, $NR^{13}$, O, $S(O)_x$, CO and $CR^{14}$ when part of an aromatic or non-aromatic ring or may additionally be $CR^{14}R^{15}$ when part of a non aromatic ring,
$Y^2$ is a 2 to 6 atom linker group, each atom of $Y^2$ being independently selected from N, $NR^{13}$, O, $S(O)_x$, CO and $CR^{14}$ when part of an aromatic or non-aromatic ring or may additionally be $CR^{14}R^{15}$ when part of a non aromatic ring;
each $R^{13}$ can notably be hydrogen;
each of $R^{14}$ and $R^{15}$ can notably be hydrogen;
each x is independently 0, 1 or 2;
U is CO, $SO_2$ or $CH_2$;

$R^4$ can also be a group —$X^{1a}$—$X^{2a}$—$X^{3a}$—$X^{4a}$ wherein the group $X^{1a}$—$X^{2a}$—$X^{3a}$ can notably be $CH_2CH=CH$ or $COCH=CH$ and $X^{4a}$ can notably be a phenyl substituted one to three times wherein the substituents are notably selected from halogen atoms;
which compounds of formula (A2) can be used as antibacterials.
WO 2004/035569 discloses antibacterial compounds of formula (A3)

(A3)

$$R^1\underset{X_5}{\overset{X_1}{\diagdown}}\underset{X_4}{\overset{A}{\diagup}}\underset{N}{\overset{R^3}{\diagdown}}\underset{X_3}{\overset{X_3}{\diagup}}$$

wherein
$R^1$ represents notably an alkoxy group;
each of $X_1$, $X_2$, $X_3$, $X_4$ and $X_5$ independently represents nitrogen atom or a $CR^2$ group;
$R^2$ represents a hydrogen atom, a halogen atom, a hydroxy group, an alkyloxy group or a heteroalkyloxy group;
A represents notably an alkylene chain or a heteroalkylene chain;
$R^3$ represents notably the group $$-\!\!\!\!\!-\!\!\!\!\!\diagup\!\!\!\!\bigcirc\!\!\!\!\!-\!R^5$$
$$\quad\quad R^4{}_n$$

wherein
n can be 0 (the group $R^4$ being then absent), and
$R^5$ can notably be a group of the formula —Y-Cy, Y being notably a $C_1$-$C_6$ heteroalkylene group and Cy being notably a possibly substituted phenyl or heteroaryl group;
whereby
an alkyl group may be straight or branched, comprise 1 to 20 carbon atoms and possibly include one or more halogen atoms in replacement of one or more of the hydrogen atoms of the alkyl group; and
a heteroalkyl group/a heteroalkylene chain stands for a straight or branched alkyl group/alkylene chain wherein one or more of the carbon atoms has/have been replaced by one or more heteroatoms which are each independently selected from inter alia an oxygen, a nitrogen and a sulphur atom;
by heteroaryl group shall be understood (notably) an aromatic group consisting of one or more rings and containing 5 to 14 ring atoms, one or more of these ring atoms being each independently selected from inter alia an oxygen, a nitrogen and a sulphur atom, which aromatic group can be unsubstituted or substituted by substituents which are each independently selected from inter alia halogen atoms, OH and $NH_2$.

It should however be noted that no specific example of compound of formula I as defined in this application is taught in WO 03/087098, WO 2004/002992 or WO 2004/035569.

It has now surprisingly been found that certain aminoethyl cyclohexyl derivatives are especially potent antimicrobial agents that are notably effective against a variety of both Gram positive and negative multi-drug resistant bacteria and especially against *P. aeruginosa* and *Acinetobacter* species.

BRIEF SUMMARY OF THE INVENTION

Various embodiments of the instant invention are presented hereafter:

i) The invention firstly relates to aminoethyl cyclohexyl derivatives of formula I

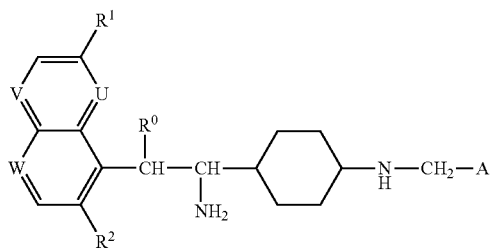

I wherein
$R^0$ represents H or OH;
$R^1$ represents alkoxy;
U and W represent N, V represents CH and $R^2$ represents H or F, or
U and V represent CH, W represents N and $R^2$ represents H or F, or
U and V represent N, W represents CH and $R^2$ represents H, or
U represents N, V represents CH, W represents $CR^a$ and $R^2$ represents H;
$R^a$ represents $CH_2OH$ or alkoxycarbonyl;
A represents the group CH=CH—B or a binuclear heterocyclic system D;
B represents a mono- or di-substituted phenyl group wherein the substituents are halogen atoms;
D represents either the group

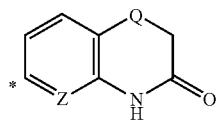

wherein
Z represents CH or N, and
Q represents O or S,
or the group

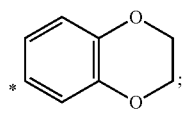

and to salts of compounds of formula I.

The compounds of formula I according to this invention may contain one or more stereogenic or asymmetric centers, such as one or more asymmetric carbon atoms. Substituents at a double bond may be present in the Z- or E-configuration unless indicated otherwise. The compounds of formula I may thus be present as mixtures of stereoisomers or preferably as pure stereoisomers. Mixtures of stereoisomers can be separated in a manner known to a person skilled in the art.

The relative configuration of stereoisomers is denoted as follows: for example, trans-(4R*,5R*)-4-{4-[(E)-3-(2,5-difluoro-phenyl)-allylamino]-cyclohexyl}-5-(6-methoxy-[1,5]naphthyridin-4-yl)-oxazolidin-2-one denominates trans-(4R,5R)-4-{4-[(E)-3-(2,5-difluoro-phenyl)-allylamino]-cyclohexyl}-5-(6-methoxy-[1,5]naphthyridin-4-yl)-oxazolidin-2-one, or trans-(4S,5S)-4-{4-[(E)-3-(2,5-difluoro-phenyl)-allylamino]-cyclohexyl}-5-(6-methoxy-[1,5]naphthyridin-4-yl)-oxazolidin-2-one, or mixtures of these two stereoisomers.

DETAILED DESCRIPTION OF THE PREFERRED EMBODIMENTS

The following paragraphs provide definitions of the various chemical moieties for the compounds according to the invention and are intended to apply uniformly throughout the specification and claims, unless an otherwise expressly set out definition provides a broader or narrower definition:

The term "alkyl", used alone or in combination, refers to a saturated straight or branched chain alkyl group, containing from one to four carbon atoms. Representative examples of alkyl groups include methyl, ethyl, propyl, iso-propyl, n-butyl, iso-butyl, sec-butyl and tert-butyl. The term "$(C_1-C_x)$alkyl" (x being an integer) refers to a straight or branched chain alkyl group containing 1 to x carbon atoms.

The term "alkoxy", used alone or in combination, refers to a saturated straight or branched chain alkoxy group, containing from one to four carbon atoms. Representative examples of alkoxy groups include methoxy, ethoxy, propoxy, iso-propoxy, n-butoxy, iso-butoxy, sec-butoxy and tert-butoxy. The term "$(C_1-C_x)$alkoxy" refers to a straight or branched chain alkoxy group containing 1 to x carbon atoms.

The term "halogen" refers to fluorine, chlorine, bromine or iodine, preferably to fluorine or chlorine.

The term "alkoxycarbonyl" refers to an alkoxycarbonyl group wherein the alkoxy group is a saturated straight or branched chain alkoxy group containing from one to four carbon atoms. Representative examples of alkoxycarbonyl include, but are not limited to, methoxycarbonyl and ethoxycarbonyl.

When in the formula

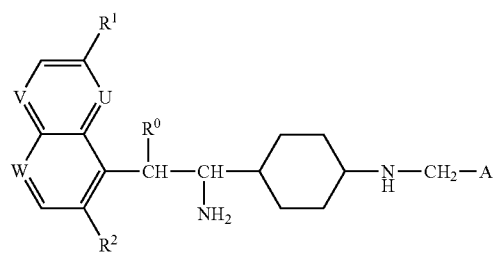

A represents the radical CH=CH—B, this means specifically that the terminal CH of the CH=CH—B radical is attached to the $CH_2$ group.

Moreover, the sign "*" placed near an atom will be used to designate the point of attachment of a radical to the rest of a molecule. For example:

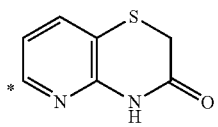

designates the 3-oxo-3,4,4a,8a-tetrahydro-2H-pyrido[3,2-b][1,4]thiazin-6-yl radical.

ii) In particular, the invention relates to compounds of formula I that are also compounds of formula $I_{CE}$

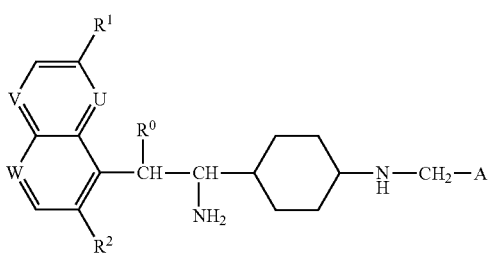

$I_{CE}$ wherein
$R^0$ represents H or OH;
$R^1$ represents alkoxy (in particular methoxy);
U and W represent N, V represents CH and $R^2$ represents H or F, or
U and V represent CH, W represents N and $R^2$ represents H or F (and notably F), or
U and V represent N, W represents CH and $R^2$ represents H, or
U represents N, V represents CH, W represents $CR^a$ and $R^2$ represents H;
$R^a$ represents $CH_2OH$ or alkoxycarbonyl;
A represents the group CH=CH—B or a binuclear heterocyclic system D;
B represents a di-substituted phenyl group wherein the substituents are halogen atoms (in particular fluorine atoms), especially the 2,5-difluorophenyl group;
D represents either the group

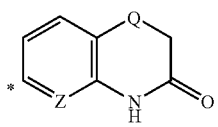

wherein
Z represents CH or N, and
Q represents O or S;
or the group

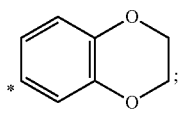

and to salts of compounds of formula $I_{CE}$.

iii) The present invention further relates to compounds of formula I as defined in embodiment i) which are also compounds of formula $I_P$

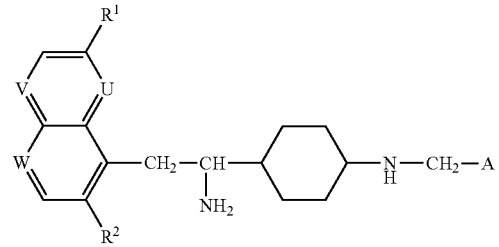

$I_P$ wherein
$R^1$ represents alkoxy;
U and W represent N, V represents CH and $R^2$ represents H or F, or
U and V represent CH, W represents N and $R^2$ represents H or F, or
U and V represent N, W represents CH and $R^2$ represents H, or
U represents N, V represents CH, W represents $CR^a$ and $R^2$ represents H;
$R^a$ represents $CH_2OH$ or alkoxycarbonyl;
A represents the group CH=CH—B or a binuclear heterocyclic system D;
B represents a mono- or di-substituted phenyl group wherein the substituents are halogen atoms;
D represents the group

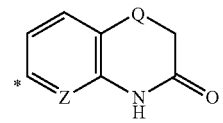

wherein
Z represents CH or N, and
Q represents O or S;
and to salts of compounds of formula $I_P$.

iv) According to a particular variant of embodiment iii), the invention relates to compounds of formula $I_P$ that are also compounds of formula $I_{CEP}$

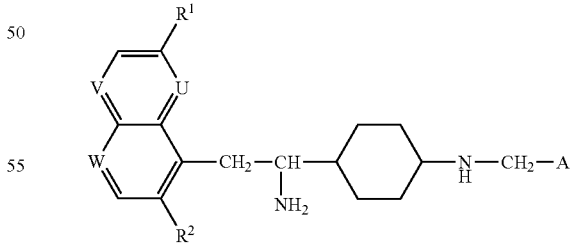

$I_{CEP}$ wherein
$R^1$ represents alkoxy (in particular methoxy);
U and W represent N, V represents CH and $R^2$ represents H or F, or
U and V represent CH, W represents N and $R^2$ represents F, or
U and V represent N, W represents CH and $R^2$ represents H, or U represents N, V represents CH, W represents CR$^a$ and R$^2$ represents H;

R$^a$ represents CH$_2$OH or alkoxycarbonyl;

A represents the group CH=CH—B or a binuclear heterocyclic system D;

B represents a di-substituted phenyl group wherein the substituents are halogen atoms (in particular fluorine atoms), especially the 2,5-difluorophenyl group;

D represents the group

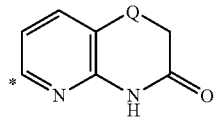

wherein

Z represents CH or N, and

Q represents O or S;

and to salts of compounds of formula I$_{CEP}$.

v) Preferred compounds of formula I or I$_P$ are those wherein at least one of the following characteristics is present:

R$^1$ represents (C$_1$-C$_3$)alkoxy;

A represents the group CH=CH—B wherein B represents a mono- or di-substituted phenyl group wherein the substituents are fluorine atoms (and notably a di-substituted phenyl group wherein the substituents are fluorine atoms, in particular 2,5-difluorophenyl), or A is a binuclear heterocyclic system D, D representing the group

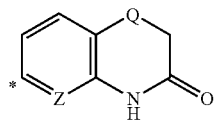

wherein

Z represents N, and

Q represents O or S;

U and W represent N, V represents CH and R$^2$ represents H or F, or

U and V represent CH, W represents N and R$^2$ represents F, or

U and V represent N, W represents CH and R$^2$ represents H, or

U represents N, V represents CH, W represents CR$^a$ and R$^2$ represents H;

R$^a$ represents CH$_2$OH or alkoxycarbonyl.

vi) More preferred compounds of formula I or I$_P$ are those wherein at least one of the following characteristics is present:

R$^1$ represents methoxy or ethoxy;

A represents the group CH=CH—B wherein B represents 2,5-difluorophenyl, or A represents a binuclear heterocyclic system D, D representing the group

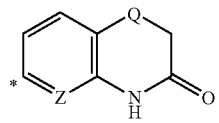

wherein

Z represents N, and

Q represents O or S;

U and W represent N, V represents CH and R$^2$ represents H or F, or

U and V represent CH, W represents N and R$^2$ represents F, or

U and V represent N, W represents CH and R$^2$ represents H, or

U represents N, V represents CH, W represents CR$^a$ and R$^2$ represents H;

R$^a$ represents CH$_2$OH.

vii) Particularly preferred compounds of formula I or I$_P$ are those wherein at least one of the following characteristics is present:

R$^1$ represents methoxy;

A represents 3-oxo-3,4,4a,8a-tetrahydro-2H-pyrido[3,2-b][1,4]thiazin-6-yl, 3-oxo-3,4,4a,8a-tetrahydro-2H-pyrido[3,2-b][1,4]oxazin-6-yl (and in particular 3-oxo-3,4,4a,8a-tetrahydro-2H-pyrido[3,2-b][1,4]thiazin-6-yl);

U and W represent N, V represents CH and R$^2$ represents H or F, or

U and V represent CH, W represents N and R$^2$ represents F, or

U and V represent N, W represents CH and R$^2$ represents H.

viii) According to one embodiment of this invention, the compounds of formula I or I$_P$ will be such that A represents the group CH=CH—B.

ix) According to another embodiment of this invention, the compounds of formula I or I$_P$ will be such that A represents the binuclear heterocyclic system D.

x) According to one variant of embodiment ix), the compounds of formula I or I$_P$ will be such that D represents the group.

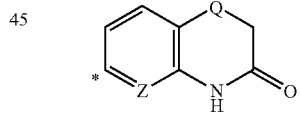

wherein

Z represents CH or N (and notably N), and

Q represents O or S.

xi) According to another variant of embodiment ix), the compounds of formula I or I$_P$ will be such that D represents the group.

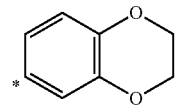

xii) According to yet another embodiment of this invention, the compounds of formula I will be such that R$^0$ represents H. These compounds will hereafter be called "compounds of formula I$_H$".

xiii) According to a further embodiment of this invention, the compounds of formula I will be such that $R^0$ represents OH. These compounds will hereafter be called "compounds of formula $I_{OH}$".

xiv) According to a first main variant of this invention, the compounds of formula I or $I_P$ will be such that U and W represent N, V represents CH and $R^2$ represents H or F.

xv) According to a second main variant of this invention, the compounds of formula I or $I_P$ will be such that U and V represent CH, W represents N and $R^2$ represents H or F (in particular F).

xvi) According to a third main variant of this invention, the compounds of formula I or $I_P$ will be such that U and V represent N, W represents CH and $R^2$ represents H.

xvii) According to a fourth main variant of this invention, the compounds of formula I or $I_P$ will be such that U represents N, V represents CH, W represents $CR^a$ and $R^2$ represents H.

xviii) The compounds of formula I or $I_P$ according to embodiment xvii) will preferably be such that $R^a$ represents $CH_2OH$.

xix) In a general manner, the compounds of formula I or $I_P$ wherein U and W represent N, V represents CH and $R^2$ represents H or F, or U and V represent CH, W represents N and $R^2$ represents F, or U and V represent N, W represents CH and $R^2$ represents H will be preferred.

xx) Especially preferred are compounds of formula I or of formula $I_{CE}$ wherein the two non-hydrogen substituents in positions 1 and 4 of the cyclohexyl ring are trans configured and wherein the amino and hydroxyl groups are syn configured as depicted in structure Ia

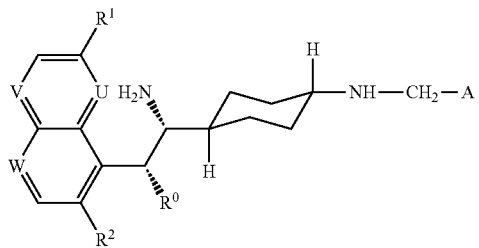

Ia

In other words, compounds of formula I or $I_{CE}$ wherein $R^0$ is H and the carbon atom bearing the $NH_2$ group has an (S) absolute configuration or compounds of formula I or $I_{CE}$ wherein $R^0$ is OH, the carbon atom bearing the $NH_2$ group has an (R) absolute configuration and the carbon atom bearing the OH group has an (R) absolute configuration are especially preferred.

xxi) Also especially preferred are compounds of formula $I_P$ or of formula $I_{CEP}$ wherein the two non-hydrogen substituents in positions 1 and 4 of the cyclohexyl ring are trans configured and wherein the stereochemistry of the carbon bearing the amino group is as depicted in structure $Ia_P$

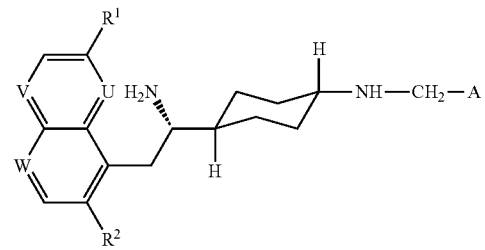

$Ia_P$

In other words, compounds of formula $I_P$ or of formula $I_{CEP}$ wherein the carbon atom bearing the $NH_2$ group has an (S) absolute configuration are especially preferred.

xxii) Moreover, compounds of formula I wherein A represents 3-oxo-3,4,4a,8a-tetrahydro-2H-pyrido[3,2-b][1,4]thiazin-6-yl, 3-oxo-3,4,4a,8a-tetrahydro-2H-pyrido[3,2-b][1,4]oxazin-6-yl, 2,3-dihydro-benzo[1,4]dioxin-6-yl or 2-(2,5-difluoro-phenyl)-vinyl (notably compounds of formula I wherein A represents 3-oxo-3,4,4a,8a-tetrahydro-2H-pyrido[3,2-b][1,4]thiazin-6-yl, 3-oxo-3,4,4a,8a-tetrahydro-2H-pyrido[3,2-b][1,4]oxazin-6-yl or 2-(2,5-difluoro-phenyl)-vinyl and especially compounds of formula I wherein A represents 3-oxo-3,4,4a,8a-tetrahydro-2H-pyrido[3,2-b][1,4]thiazin-6-yl or 3-oxo-3,4,4a,8a-tetrahydro-2H-pyrido[3,2-b][1,4]oxazin-6-yl) will be particularly preferred.

xxiii) The following compounds of formula I are preferred:
6-(trans-{4-[(1R)-1-amino-2-(6-methoxy-[1,5]naphthyridin-4-yl)-ethyl]-cyclohexylamino}-methyl)-4H-pyrido[3,2-b][1,4]thiazin-3-one;
6-(trans-{4-[(1S)-1-amino-2-(6-methoxy-[1,5]naphthyridin-4-yl)-ethyl]-cyclohexylamino}-methyl)-4H-pyrido[3,2-b][1,4]thiazin-3-one;
6-(trans-{4-[(1R*,2R*)-1-amino-2-hydroxy-2-(6-methoxy-[1,5]naphthyridin-4-yl)-ethyl]-cyclohexylamino}-methyl)-4H-pyrido[3,2-b][1,4]thiazin-3-one;
trans-{4-[1-amino-2-(6-methoxy-[1,5]naphthyridin-4-yl)-ethyl]-cyclohexyl}-[3-(2,5-difluoro-phenyl)-allyl]-amine;
8-[2-amino-2-trans-{4-[(E)-3-(2,5-difluoro-phenyl)-allylamino]-cyclohexyl}-ethyl]-2-methoxy-quinoline-5-carboxylic acid methyl ester;
[8-(2-amino-2-trans-{4-[3-(E)-(2,5-difluoro-phenyl)-allylamino]-cyclohexyl}-ethyl)-2-methoxy-quinolin-5-yl]-methanol;
6-(trans-{4-[1-amino-2-(3-methoxy-quinoxalin-5-yl)-ethyl]-cyclohexylamino}-methyl)-4H-pyrido[3,2-b][1,4]thiazin-3-one;
6-(cis-{4-[1-amino-2-(3-methoxy-quinoxalin-5-yl)-ethyl]-cyclohexylamino}-methyl)-4H-pyrido[3,2-b][1,4]thiazin-3-one;
6-(trans-{4-[1-amino-2-(6-methoxy-[1,5]naphthyridin-4-yl)-ethyl]-cyclohexylamino}-methyl)-4H-pyrido[3,2-b][1,4]oxazin-3-one;
trans-6-({4-[1-amino-2-(3-fluoro-6-methoxy-quinolin-4-yl)-ethyl]-cyclohexylamino}-methyl)-4H-pyrido[3,2-b][1,4]thiazin-3-one;
cis-6-({4-[1-amino-2-(3-fluoro-6-methoxy-quinolin-4-yl)-ethyl]-cyclohexylamino}-methyl)-4H-pyrido[3,2-b][1,4]thiazin-3-one;
trans-{4-[1-amino-2-(3-fluoro-6-methoxy-quinolin-4-yl)-ethyl]-cyclohexyl}-[3-(E)-(2,5-difluoro-phenyl)-allyl]-amine;
cis-{4-[1-amino-2-(3-fluoro-6-methoxy-quinolin-4-yl)-ethyl]-cyclohexyl}-[3-(E)-(2,5-difluoro-phenyl)-allyl]-amine;

trans-6-({4-[1-amino-2-(3-fluoro-6-methoxy-[1,5]naphthyridin-4-yl)-ethyl]-cyclohexylamino}-methyl)-4H-pyrido[3,2-b][1,4]thiazin-3-one;
cis-6-({4-[1-amino-2-(3-fluoro-6-methoxy-[1,5]naphthyridin-4-yl)-ethyl]-cyclohexylamino}-methyl)-4H-pyrido[3,2-b][1,4]thiazin-3-one;
trans-6-({4-[1-amino-2-(3-fluoro-6-methoxy-quinolin-4-yl)-ethyl]-cyclohexylamino}-methyl)-4H-benzo[1,4]oxazin-3-one;
trans-(1R*,2R*)-2-amino-2-{4-[(2,3-dihydro-benzo[1,4]dioxin-6-ylmethyl)-amino]-cyclohexyl}-1-(6-methoxy-[1,5]naphthyridin-4-yl)-ethanol;
trans-(1R*,2R*)-2-amino-2-{4-[(E)-3-(2,5-difluoro-phenyl)-allylamino]-cyclohexyl}-1-(6-methoxy-[1,5]naphthyridin-4-yl)-ethanol;
trans-6-({4-[1-amino-2-(6-methoxy-quinolin-4-yl)-ethyl]-cyclohexylamino}-methyl)-4H-benzo[1,4]oxazin-3-one;
trans-6-({4-[1-amino-2-(6-methoxy-quinolin-4-yl)-ethyl]-cyclohexylamino}-methyl)-4H-pyrido[3,2-b][1,4]thiazin-3-one;
trans-6-({4-[1-amino-2-(6-methoxy-quinolin-4-yl)-ethyl]-cyclohexylamino}-methyl)-4H-pyrido[3,2-b][1,4]oxazin-3-one;

as well as the salts (in particular the pharmaceutically acceptable salts) thereof.

xxiv) The following compounds of formula I are also preferred:

6-(trans-{4-[(1R)-1-amino-2-(6-methoxy-[1,5]naphthyridin-4-yl)-ethyl]-cyclohexylamino}-methyl)-4H-pyrido[3,2-b][1,4]thiazin-3-one;
6-(trans-{4-[(1S)-1-amino-2-(6-methoxy-[1,5]naphthyridin-4-yl)-ethyl]-cyclohexylamino}-methyl)-4H-pyrido[3,2-b][1,4]thiazin-3-one;
6-(trans-{4-[(1R,2R)-1-amino-2-hydroxy-2-(6-methoxy-[1,5]naphthyridin-4-yl)-ethyl]-cyclohexylamino}-methyl)-4H-pyrido[3,2-b][1,4]thiazin-3-one;
6-(trans-{4-[(1S,2S)-1-amino-2-hydroxy-2-(6-methoxy-[1,5]naphthyridin-4-yl)-ethyl]-cyclohexylamino}-methyl)-4H-pyrido[3,2-b][1,4]thiazin-3-one;
trans-{4-[(1R)-1-amino-2-(6-methoxy-[1,5]naphthyridin-4-yl)-ethyl]-cyclohexyl}-[3-(2,5-difluoro-phenyl)-allyl]-amine;
trans-{4-[(1S)-1-amino-2-(6-methoxy-[1,5]naphthyridin-4-yl)-ethyl]-cyclohexyl}-[3-(2,5-difluoro-phenyl)-allyl]-amine;
8-[(2R)-2-amino-2-trans-{4-[(E)-3-(2,5-difluoro-phenyl)-allylamino]-cyclohexyl}-ethyl]-2-methoxy-quinoline-5-carboxylic acid methyl ester;
8-[(2S)-2-amino-2-trans-{4-[(E)-3-(2,5-difluoro-phenyl)-allylamino]-cyclohexyl}-ethyl]-2-methoxy-quinoline-5-carboxylic acid methyl ester;
[8-((2R)-2-amino-2-trans-{4-[3-(E)-(2,5-difluoro-phenyl)-allylamino]-cyclohexyl}-ethyl)-2-methoxy-quinolin-5-yl]-methanol;
[8-((2S)-2-amino-2-trans-{4-[3-(E)-(2,5-difluoro-phenyl)-allylamino]-cyclohexyl}-ethyl)-2-methoxy-quinolin-5-yl]-methanol;
6-(trans-{4-[(1R)-1-amino-2-(3-methoxy-quinoxalin-5-yl)-ethyl]-cyclohexylamino}-methyl)-4H-pyrido[3,2-b][1,4]thiazin-3-one;
6-(trans-{4-[(1S)-1-amino-2-(3-methoxy-quinoxalin-5-yl)-ethyl]-cyclohexylamino}-methyl)-4H-pyrido[3,2-b][1,4]thiazin-3-one;
6-(cis-{4-[(1R)-1-amino-2-(3-methoxy-quinoxalin-5-yl)-ethyl]-cyclohexylamino}-methyl)-4H-pyrido[3,2-b][1,4]thiazin-3-one;
6-(cis-{4-[(1S)-1-amino-2-(3-methoxy-quinoxalin-5-yl)-ethyl]-cyclohexylamino}-methyl)-4H-pyrido[3,2-b][1,4]thiazin-3-one;
6-(trans-{4-[(1R)-1-amino-2-(6-methoxy-[1,5]naphthyridin-4-yl)-ethyl]-cyclohexylamino}-methyl)-4H-pyrido[3,2-b][1,4]oxazin-3-one;
6-(trans-{4-[(1S)-1-amino-2-(6-methoxy-[1,5]naphthyridin-4-yl)-ethyl]-cyclohexylamino}-methyl)-4H-pyrido[3,2-b][1,4]oxazin-3-one;
trans-6-({4-[(1R)-1-amino-2-(3-fluoro-6-methoxy-quinolin-4-yl)-ethyl]-cyclohexylamino}-methyl)-4H-pyrido[3,2-b][1,4]thiazin-3-one;
trans-6-({4-[(1S)-1-amino-2-(3-fluoro-6-methoxy-quinolin-4-yl)-ethyl]-cyclohexylamino}-methyl)-4H-pyrido[3,2-b][1,4]thiazin-3-one;
cis-6-({4-[(1R)-1-amino-2-(3-fluoro-6-methoxy-quinolin-4-yl)-ethyl]-cyclohexylamino}-methyl)-4H-pyrido[3,2-b][1,4]thiazin-3-one;
cis-6-({4-[(1S)-1-amino-2-(3-fluoro-6-methoxy-quinolin-4-yl)-ethyl]-cyclohexylamino}-methyl)-4H-pyrido[3,2-b][1,4]thiazin-3-one;
trans-{4-[(1R)-1-amino-2-(3-fluoro-6-methoxy-quinolin-4-yl)-ethyl]-cyclohexyl}-[3-(E)-(2,5-difluoro-phenyl)-allyl]-amine;
trans-{4-[(1S)-1-amino-2-(3-fluoro-6-methoxy-quinolin-4-yl)-ethyl]-cyclohexyl}-[3-(E)-(2,5-difluoro-phenyl)-allyl]-amine;
cis-{4-[(1R)-1-amino-2-(3-fluoro-6-methoxy-quinolin-4-yl)-ethyl]-cyclohexyl}-[3-(E)-(2,5-difluoro-phenyl)-allyl]-amine;
cis-{4-[(1S)-1-amino-2-(3-fluoro-6-methoxy-quinolin-4-yl)-ethyl]-cyclohexyl}-[3-(E)-(2,5-difluoro-phenyl)-allyl]-amine;
trans-6-({4-[(1R)-1-amino-2-(3-fluoro-6-methoxy-[1,5]naphthyridin-4-yl)-ethyl]-cyclohexylamino}-methyl)-4H-pyrido[3,2-b][1,4]thiazin-3-one;
trans-6-({4-[(1S)-1-amino-2-(3-fluoro-6-methoxy-[1,5]naphthyridin-4-yl)-ethyl]-cyclohexylamino}-methyl)-4H-pyrido[3,2-b][1,4]thiazin-3-one;
cis-6-({4-[(1R)-1-amino-2-(3-fluoro-6-methoxy-[1,5]naphthyridin-4-yl)-ethyl]-cyclohexylamino}-methyl)-4H-pyrido[3,2-b][1,4]thiazin-3-one;
cis-6-({4-[(1S)-1-amino-2-(3-fluoro-6-methoxy-[1,5]naphthyridin-4-yl)-ethyl]-cyclohexylamino}-methyl)-4H-pyrido[3,2-b][1,4]thiazin-3-one;
trans-6-({4-[(1R)-1-amino-2-(3-fluoro-6-methoxy-quinolin-4-yl)-ethyl]-cyclohexylamino}-methyl)-4H-benzo[1,4]oxazin-3-one;
trans-6-({4-[(1S)-1-amino-2-(3-fluoro-6-methoxy-quinolin-4-yl)-ethyl]-cyclohexylamino}-methyl)-4H-benzo[1,4]oxazin-3-one;
trans-(1R,2R)-2-amino-2-{4-[(2,3-dihydro-benzo[1,4]dioxin-6-ylmethyl)-amino]-cyclohexyl}-1-(6-methoxy-[1,5]naphthyridin-4-yl)-ethanol;
trans-(1S,2S)-2-amino-2-{4-[(2,3-dihydro-benzo[1,4]dioxin-6-ylmethyl)-amino]-cyclohexyl}-1-(6-methoxy-[1,5]naphthyridin-4-yl)-ethanol;
trans-(1R,2R)-2-amino-2-{4-[(E)-3-(2,5-difluoro-phenyl)-allylamino]-cyclohexyl}-1-(6-methoxy-[1,5]naphthyridin-4-yl)-ethanol;
trans-(1S,2S)-2-amino-2-{4-[(E)-3-(2,5-difluoro-phenyl)-allylamino]-cyclohexyl}-1-(6-methoxy-[1,5]naphthyridin-4-yl)-ethanol;
trans-6-({4-[(1R)-1-amino-2-(6-methoxy-quinolin-4-yl)-ethyl]-cyclohexylamino}-methyl)-4H-benzo[1,4]oxazin-3-one;

trans-6-({4-[(1S)-1-amino-2-(6-methoxy-quinolin-4-yl)-ethyl]-cyclohexylamino}-methyl)-4H-benzo[1,4]oxazin-3-one;
trans-6-({4-[(1R)-amino-2-(6-methoxy-quinolin-4-yl)-ethyl]-cyclohexylamino}-methyl)-4H-pyrido[3,2-b][1,4]thiazin-3-one;
trans-6-({4-[(1S)-amino-2-(6-methoxy-quinolin-4-yl)-ethyl]-cyclohexylamino}-methyl)-4H-pyrido[3,2-b][1,4]thiazin-3-one;
trans-6-({4-[(1R)-1-amino-2-(6-methoxy-quinolin-4-yl)-ethyl]-cyclohexylamino}-methyl)-4H-pyrido[3,2-b][1,4]oxazin-3-one;
trans-6-({4-[(1S)-1-amino-2-(6-methoxy-quinolin-4-yl)-ethyl]-cyclohexylamino}-methyl)-4H-pyrido[3,2-b][1,4]oxazin-3-one;

as well as the salts (in particular the pharmaceutically acceptable salts) thereof.

xxv) Particularly preferred are the following compounds of formula I:

6-(trans-{4-[(1R)-1-amino-2-(6-methoxy-[1,5]naphthyridin-4-yl)-ethyl]-cyclohexylamino}-methyl)-4H-pyrido[3,2-b][1,4]thiazin-3-one;
6-(trans-{4-[(1S)-1-amino-2-(6-methoxy-[1,5]naphthyridin-4-yl)-ethyl]-cyclohexylamino}-methyl)-4H-pyrido[3,2-b][1,4]thiazin-3-one;
6-(trans-{4-[(1R,2R)-1-amino-2-hydroxy-2-(6-methoxy-[1,5]naphthyridin-4-yl)-ethyl]-cyclohexylamino}-methyl)-4H-pyrido[3,2-b][1,4]thiazin-3-one;
6-(trans-{4-[(1S,2S)-1-amino-2-hydroxy-2-(6-methoxy-[1,5]naphthyridin-4-yl)-ethyl]-cyclohexylamino}-methyl)-4H-pyrido[3,2-b][1,4]thiazin-3-one;
trans-{4-[(1R)-1-amino-2-(6-methoxy-[1,5]naphthyridin-4-yl)-ethyl]-cyclohexyl}-[3-(2,5-difluoro-phenyl)-allyl]-amine;
trans-{4-[(1S)-1-amino-2-(6-methoxy-[1,5]naphthyridin-4-yl)-ethyl]-cyclohexyl}-[3-(2,5-difluoro-phenyl)-allyl]-amine;
8-[(2R)-2-amino-2-trans-{4-[(E)-3-(2,5-difluoro-phenyl)-allylamino]-cyclohexyl}-ethyl]-2-methoxy-quinoline-5-carboxylic acid methyl ester;
8-[(2S)-2-amino-2-trans-{4-[(E)-3-(2,5-difluoro-phenyl)-allylamino]-cyclohexyl}-ethyl]-2-methoxy-quinoline-5-carboxylic acid methyl ester;
[8-((2R)-2-amino-2-trans-{4-[3-(E)-(2,5-difluoro-phenyl)-allylamino]-cyclohexyl}-ethyl)-2-methoxy-quinolin-5-yl]-methanol;
[8-((2S)-2-amino-2-trans-{4-[3-(E)-(2,5-difluoro-phenyl)-allylamino]-cyclohexyl}-ethyl)-2-methoxy-quinolin-5-yl]-methanol;
6-(trans-{4-[(1R)-1-amino-2-(3-methoxy-quinoxalin-5-yl)-ethyl]-cyclohexylamino}-methyl)-4H-pyrido[3,2-b][1,4]thiazin-3-one;
6-(trans-{4-[(1S)-1-amino-2-(3-methoxy-quinoxalin-5-yl)-ethyl]-cyclohexylamino}-methyl)-4H-pyrido[3,2-b][1,4]thiazin-3-one;
6-(cis-{4-[(1R)-1-amino-2-(3-methoxy-quinoxalin-5-yl)-ethyl]-cyclohexylamino}-methyl)-4H-pyrido[3,2-b][1,4]thiazin-3-one;
6-(cis-{4-[(1S)-1-amino-2-(3-methoxy-quinoxalin-5-yl)-ethyl]-cyclohexylamino}-methyl)-4H-pyrido[3,2-b][1,4]thiazin-3-one;
6-(trans-{4-[(1R)-1-amino-2-(6-methoxy-[1,5]naphthyridin-4-yl)-ethyl]-cyclohexylamino}-methyl)-4H-pyrido[3,2-b][1,4]oxazin-3-one;
6-(trans-{4-[(1S)-1-amino-2-(6-methoxy-[1,5]naphthyridin-4-yl)-ethyl]-cyclohexylamino}-methyl)-4H-pyrido[3,2-b][1,4]oxazin-3-one;
trans-6-({4-[(1R)-1-amino-2-(3-fluoro-6-methoxy-quinolin-4-yl)-ethyl]-cyclohexylamino}-methyl)-4H-pyrido[3,2-b][1,4]thiazin-3-one;
trans-6-({4-[(1S)-1-amino-2-(3-fluoro-6-methoxy-quinolin-4-yl)-ethyl]-cyclohexylamino}-methyl)-4H-pyrido[3,2-b][1,4]thiazin-3-one;
cis-6-({4-[(1R)-1-amino-2-(3-fluoro-6-methoxy-quinolin-4-yl)-ethyl]-cyclohexylamino}-methyl)-4H-pyrido[3,2-b][1,4]thiazin-3-one;
cis-6-({4-[(1S)-1-amino-2-(3-fluoro-6-methoxy-quinolin-4-yl)-ethyl]-cyclohexylamino}-methyl)-4H-pyrido[3,2-b][1,4]thiazin-3-one;
trans-{4-[(1R)-1-amino-2-(3-fluoro-6-methoxy-quinolin-4-yl)-ethyl]-cyclohexyl}-[3-(E)-(2,5-difluoro-phenyl)-allyl]-amine;
trans-{4-[(1S)-1-amino-2-(3-fluoro-6-methoxy-quinolin-4-yl)-ethyl]-cyclohexyl}-[3-(E)-(2,5-difluoro-phenyl)-allyl]-amine;
cis-{4-[(1R)-1-amino-2-(3-fluoro-6-methoxy-quinolin-4-yl)-ethyl]-cyclohexyl}-[3-(E)-(2,5-difluoro-phenyl)-allyl]-amine;
cis-{4-[(1S)-1-amino-2-(3-fluoro-6-methoxy-quinolin-4-yl)-ethyl]-cyclohexyl}-[3-(E)-(2,5-difluoro-phenyl)-allyl]-amine;
trans-6-({4-[(1R)-1-amino-2-(3-fluoro-6-methoxy-[1,5]naphthyridin-4-yl)-ethyl]-cyclohexylamino}-methyl)-4H-pyrido[3,2-b][1,4]thiazin-3-one;
trans-6-({4-[(1S)-1-amino-2-(3-fluoro-6-methoxy-[1,5]naphthyridin-4-yl)ethyl]-cyclohexylamino}-methyl)-4H-pyrido[3,2-b][1,4]thiazin-3-one;
cis-6-({4-[(1R)-1-amino-2-(3-fluoro-6-methoxy-[1,5]naphthyridin-4-yl)-ethyl]-cyclohexylamino}-methyl)-4H-pyrido[3,2-b][1,4]thiazin-3-one;
cis-6-({4-[(1S)-1-amino-2-(3-fluoro-6-methoxy-[1,5]naphthyridin-4-yl)-ethyl]-cyclohexylamino}-methyl)-4H-pyrido[3,2-b][1,4]thiazin-3-one;
trans-6-({4-[(1R)-1-amino-2-(3-fluoro-6-methoxy-quinolin-4-yl)-ethyl]-cyclohexylamino}-methyl)-4H-benzo[1,4]oxazin-3-one;
trans-6-({4-[(1S)-1-amino-2-(3-fluoro-6-methoxy-quinolin-4-yl)-ethyl]-cyclohexylamino}-methyl)-4H-benzo[1,4]oxazin-3-one;
trans-(1R,2R)-2-amino-2-{4-[(2,3-dihydro-benzo[1,4]dioxin-6-ylmethyl)-amino]-cyclohexyl}-1-(6-methoxy-[1,5]naphthyridin-4-yl)-ethanol;
trans-(1S,2S)-2-amino-2-{4-[(2,3-dihydro-benzo[1,4]dioxin-6-ylmethyl)-amino]-cyclohexyl}-1-(6-methoxy-[1,5]naphthyridin-4-yl)-ethanol;
trans-(1R,2R)-2-amino-2-{4-[(E)-3-(2,5-difluoro-phenyl)-allylamino]-cyclohexyl}-1-(6-methoxy-[1,5]naphthyridin-4-yl)-ethanol;
trans-(1S,2S)-2-amino-2-{4-[(E)-3-(2,5-difluoro-phenyl)-allylamino]-cyclohexyl}-1-(6-methoxy-[1,5]naphthyridin-4-yl)-ethanol;

and the salts (in particular pharmaceutically acceptable salts) thereof.

xxvi) According to a particular variant of embodiment xxv), the following compounds of formula I will be preferred:

6-(trans-{4-[(1R)-1-amino-2-(6-methoxy-[1,5]naphthyridin-4-yl)-ethyl]-cyclohexylamino}-methyl)-4H-pyrido[3,2-b][1,4]thiazin-3-one;
6-(trans-{4-[(1S)-1-amino-2-(6-methoxy-[1,5]naphthyridin-4-yl)-ethyl]-cyclohexylamino}-methyl)-4H-pyrido[3,2-b][1,4]thiazin-3-one;
trans-{4-[(1R)-1-amino-2-(6-methoxy-[1,5]naphthyridin-4-yl)-ethyl]-cyclohexyl}-[3-(2,5-difluoro-phenyl)-allyl]-amine;

trans-{4-[(1S)-1-amino-2-(6-methoxy-[1,5]naphthyridin-4-yl)-ethyl]-cyclohexyl}-[3-(2,5-difluoro-phenyl)-allyl]-amine;

8-[(2R)-2-amino-2-trans-{4-[(E)-3-(2,5-difluoro-phenyl)-allylamino]-cyclohexyl}-ethyl]-2-methoxy-quinoline-5-carboxylic acid methyl ester;

8-[(2S)-2-amino-2-trans-{4-[(E)-3-(2,5-difluoro-phenyl)-allylamino]-cyclohexyl}-ethyl]-2-methoxy-quinoline-5-carboxylic acid methyl ester;

[8-((2R)-2-amino-2-trans-{4-[3-(E)-(2,5-difluoro-phenyl)-allylamino]-cyclohexyl}-ethyl)-2-methoxy-quinolin-5-yl]-methanol;

[8-((2S)-2-amino-2-trans-{4-[3-(E)-(2,5-difluoro-phenyl)-allylamino]-cyclohexyl}-ethyl)-2-methoxy-quinolin-5-yl]-methanol;

6-(trans-{4-[(1R)-1-amino-2-(3-methoxy-quinoxalin-5-yl)-ethyl]-cyclohexylamino}-methyl)-4H-pyrido[3,2-b][1,4]thiazin-3-one;

6-(trans-{4-[(1S)-1-amino-2-(3-methoxy-quinoxalin-5-yl)-ethyl]-cyclohexylamino}-methyl)-4H-pyrido[3,2-b][1,4]thiazin-3-one;

6-(cis-{4-[(1R)-1-amino-2-(3-methoxy-quinoxalin-5-yl)-ethyl]-cyclohexylamino}-methyl)-4H-pyrido[3,2-b][1,4]thiazin-3-one;

6-(cis-{4-[(1S)-1-amino-2-(3-methoxy-quinoxalin-5-yl)-ethyl]-cyclohexylamino}-methyl)-4H-pyrido[3,2-b][1,4]thiazin-3-one;

6-(trans-{4-[(1R)-1-amino-2-(6-methoxy-[1,5]naphthyridin-4-yl)-ethyl]-cyclohexylamino}-methyl)-4H-pyrido[3,2-b][1,4]oxazin-3-one;

6-(trans-{4-[(1S)-1-amino-2-(6-methoxy-[1,5]naphthyridin-4-yl)-ethyl]-cyclohexylamino}-methyl)-4H-pyrido[3,2-b][1,4]oxazin-3-one;

trans-6-({4-[(1R)-1-amino-2-(3-fluoro-6-methoxy-quinolin-4-yl)-ethyl]-cyclohexylamino}-methyl)-4H-pyrido[3,2-b][1,4]thiazin-3-one;

trans-6-({4-[(1S)-1-amino-2-(3-fluoro-6-methoxy-quinolin-4-yl)-ethyl]-cyclohexylamino}-methyl)-4H-pyrido[3,2-b][1,4]thiazin-3-one;

cis-6-({4-[(1R)-1-amino-2-(3-fluoro-6-methoxy-quinolin-4-yl)-ethyl]-cyclohexylamino}-methyl)-4H-pyrido[3,2-b][1,4]thiazin-3-one;

cis-6-({4-[(1S)-1-amino-2-(3-fluoro-6-methoxy-quinolin-4-yl)-ethyl]-cyclohexylamino}-methyl)-4H-pyrido[3,2-b][1,4]thiazin-3-one;

trans-{4-[(1R)-1-amino-2-(3-fluoro-6-methoxy-quinolin-4-yl)-ethyl]-cyclohexyl}-[3-(E)-(2,5-difluoro-phenyl)-allyl]-amine;

trans-{4-[(1S)-1-amino-2-(3-fluoro-6-methoxy-quinolin-4-yl)-ethyl]-cyclohexyl}-[3-(E)-(2,5-difluoro-phenyl)-allyl]-amine;

cis-{4-[(1R)-1-amino-2-(3-fluoro-6-methoxy-quinolin-4-yl)-ethyl]-cyclohexyl}-[3-(E)-(2,5-difluoro-phenyl)-allyl]-amine;

cis-{4-[(1S)-1-amino-2-(3-fluoro-6-methoxy-quinolin-4-yl)-ethyl]-cyclohexyl}-[3-(E)-(2,5-difluoro-phenyl)-allyl]-amine;

trans-6-({4-[(1R)-1-amino-2-(3-fluoro-6-methoxy-[1,5]naphthyridin-4-yl)-ethyl]-cyclohexylamino}-methyl)-4H-pyrido[3,2-b][1,4]thiazin-3-one;

trans-6-({4-[(1S)-1-amino-2-(3-fluoro-6-methoxy-[1,5]naphthyridin-4-yl)-ethyl]-cyclohexylamino}-methyl)-4H-pyrido[3,2-b][1,4]thiazin-3-one;

cis-6-({4-[(1R)-1-amino-2-(3-fluoro-6-methoxy-[1,5]naphthyridin-4-yl)-ethyl]-cyclohexylamino}-methyl)-4H-pyrido[3,2-b][1,4]thiazin-3-one;

cis-6-({4-[(1S)-1-amino-2-(3-fluoro-6-methoxy-[1,5]naphthyridin-4-yl)-ethyl]-cyclohexylamino}-methyl)-4H-pyrido[3,2-b][1,4]thiazin-3-one;

as well as the salts (in particular the pharmaceutically acceptable salts) thereof.

Compounds of formula I are suitable for the use as chemotherapeutic active compounds in human and veterinary medicine and as substances for preserving inorganic and organic materials in particular all types of organic materials for example polymers, lubricants, paints, fibres, leather, paper and wood.

These compounds according to the invention (i.e. according to one of embodiments i) to xxvi)) are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus*, or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum*, or *Neisserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacterium avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

Compounds of formula I according to the present invention (i.e. according to one of embodiments i) to xxvi)) are further useful for the preparation of a medicament for the treatment of infections that are mediated by bacteria such as *E. coli, Klebsiella pneumoniae* and other Enterobacteriaceae, *Acinetobacter* spp., *Stenothrophomonas maltophilia, Neisseria meningitidis, C. difficile, Bacillus cereus, Bacillus anthracis, Corynebacterium* spp., *Propionibacterium acnes* and *bacteroide* spp.

Compounds of formula I according to the present invention (i.e. according to one of embodiments i) to xxvi)) are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

The compounds of formula I (i.e. according to one of embodiments i) to xxvi)), or the pharmaceutically acceptable salts thereof, are suitable and/or may be used for the preparation of a medicament for the prevention or treatment of diseases bacterial infections, especially those by the bacteria mentioned above.

One aspect of this invention therefore relates to the use of a compound of formula I according to this invention (i.e. according to one of embodiments i) to xxvi)), or of a pharmaceutically acceptable salt thereof, for the manufacture of a medicament for the prevention or treatment of a bacterial infection.

As well as in humans, bacterial infections can also be treated using compounds of formula I (or pharmaceutically acceptable salts thereof) in other species like pigs, ruminants, horses, dogs, cats and poultry.

The present invention also relates to pharmacologically acceptable salts and to compositions and formulations of compounds of formula I.

Any reference to a compound of formula I is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

A pharmaceutical composition according to the present invention contains at least one compound of formula I (or a pharmaceutically acceptable salt thereof) as the active agent and optionally carriers and/or diluents and/or adjuvants, and may also contain additional known antibiotics.

The production of pharmaceutical compositions can be effected in a manner which will be familiar to any person skilled in the art (see for example Remington, *The Science and Practice of Pharmacy*, 21st Edition (2005), Part 5, "Pharmaceutical Manufacturing" [published by Lippincott Williams & Wilkins]) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula I and their pharmaceutically acceptable salts can be used as medicaments, e.g. in the form of pharmaceutical compositions for enteral or parenteral administration.

Another aspect of the invention concerns a method for the prevention or the treatment of a bacterial infection in a patient comprising the administration to said patient of a pharmaceutically active amount of a derivative according to formula I or a pharmaceutically acceptable salt thereof.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

Besides, any preferences indicated for the compounds of formula I (whether for the compounds themselves, salts thereof, compositions containing the compounds or salts thereof, uses of the compounds or salts thereof, etc.) apply *mutatis mutandis* to compounds of formula $I_P$, of formula $I_{CE}$, of formula $I_{CEP}$, of formula Ia or of formula Ia$_P$, and vice versa.

The compounds of formula I can be manufactured in accordance with the present invention using the procedures described hereafter.

Preparation of Compounds of Formula I

Abbreviations:

The following abbreviations are used throughout the specification and the examples:

*A. baumannii Acetinobacter baumannii*
Ac acetyl
AcOH acetic acid
AD-mix α 1,4-bis(dihydroquinine)phthalazine, $K_3Fe(CN)_6$, $K_2CO_3$ and $K_2OsO_4.2H_2O$
AD-mix β 1,4-bis(dihydroquinidine)phthalazine, $K_3Fe(CN)_6$, $K_2CO_3$ and $K_2OsO_4.2H_2O$
AIBN azobisisobutyronitrile
Alloc allyloxycarbonyl
aq. aqueous
Boc tert-butoxycarbonyl
br. broad
n-BuLi n-butyllithium
*C. difficile Clostridium difficile*
Cbz benzyloxycarbonyl
1,2-DCE 1,2-dichloroethane
DCM dichloromethane
DEAD diethyl azodicarboxylate
DIAD diisopropyl azodicarboxylate
DIBAH diisobutylaluminium hydride
DIPA N,N-diisopropylamine
DIPEA N,N-diisopropylethylamine
DMAP 4-dimethylaminopyridine
1,2-DME 1,2-dimethoxyethane
DMF N,N-dimethylformamide
DMSO dimethylsulfoxide
DPPA diphenyl phosphoryl azide
*E. coli Escherichia coli*
*E. faecalis Enterococcus faecalis*
*E. faecium Enterococcus faecium*
EA ethyl acetate
ESI Electron Spray Ionisation
ether diethyl ether
EtOH ethanol
Fmoc 9-fluorenylmethylcarbonyl
HATU O-(7-azabenzotriazol-1-yl)-N,N,N',N'-tetramethyluronium hexafluorophosphate
Hex hexane
Hept heptane
HMPT hexamethylphosphorous triamide
$H_2O_2$ hydrogen peroxide
HV high vacuum conditions
KHMDS potassium hexamethyldisilazide LDA lithium diisopropylamide
LiHMDS lithium hexamethyldisilazide
MCPBA meta-chloroperbenzoic acid
MeCN acetonitrile
MeOH methanol
MS Mass Spectroscopy
Ms methanesulfonyl
NBS N-bromosuccinimide
org. organic
*P. aeruginosa* Pseudomonas aeruginosa
Pd/C or Pd(OH)$_2$/C palladium or palladium dihydroxide on carbon
Ph phenyl
PTSA para-toluenesulfonic acid
quant. quantitative
Rf retention factor
rt room temperature
*S. aureus* Staphylococcus aureus
*S. pneumoniae* Streptococcus pneumoniae
sat. saturated
SiO$_2$ silica gel
TBAF tetrabutylammonium fluoride
TEA triethyl amine
Tf triflyl (=trifluoromethanesulfonyl)
TFA trifluoroacetic acid
THF tetrahydrofuran
Ts tosyl (=toluenesulfonyl)
p-TsCl para-toluenesulfonyl chloride General Reaction Techniques:

1. Amine Protection:
  1.1. Amines are usually protected as carbamates such as Alloc, Cbz, Fmoc or Boc. They are obtained by reacting the amine with allyl, fluorenylmethyl or benzyl chloroformate or with di tert-butyl dicarbonate in presence of a base such as NaOH, TEA, DMAP or imidazole.
  1.2. They can also be protected as N-benzyl derivatives by reaction with benzyl bromide or chloride in presence of a base such as sodium carbonate or TEA. Alternatively, N-benzyl derivatives can be obtained through reductive amination in presence of benzaldehyde (see section 7. below).
  1.3. They can also be protected as N-acetyl derivative through reaction with acetyl chloride in presence of a a base such as sodium carbonate or TEA or with acetic acid anhydride in presence of sodium acetate.
  1.4. Amines can furthermore be protected as sulphonamides by their reaction with 2-nitro- or 4-nitro-phenylsulphonyl chloride in a solvent such as DCM or THF in presence of a base such as TEA or NaOH between −10° C. and 40° C.
  1.5. Further strategies to introduce other amine protecting groups have been described in *Protecting Groups in Organic Synthesis*, 3$^{rd}$ Ed (1999), 494-653; T. W. Greene, P. G. M. Wuts; (Publisher: John Wiley and Sons, Inc., New York, N.Y.).

2. Amine Deprotection:
  2.1. The benzyl carbamates are deprotected by hydrogenolysis over a noble catalyst (e.g. Pd/C). The Boc group is removed under acidic conditions such as HCl in an organic solvent such as EA, or TFA neat or diluted in a solvent such DCM. The Alloc group is removed in presence of tetrakis (triphenylphosphine)palladium(0) in presence of an allyl cation scavenger such as morpholine, dimedone or tributyltin hydride between 0° C. and 50° C. in a solvent such as THF.
  2.2. The N-benzyl protected amines are deprotected by hydrogenolysis over a noble catalyst (e.g. Pd(OH)$_2$).
  2.3. The N-acetyl protecting group is removed under basic conditions such as Na$_2$CO$_3$, LiOH or NaOH in aq. MeOH or THF, or under acidic conditions such as aq. HCl in THF.
  2.4. The Fmoc protecting group is removed under mild basic conditions such as diluted morpholine or piperidine in DMF.
  2.5. The 2- or 4-nitro-phenylsulphonamides can be deprotected by using thiophenol in DMF in presence of a base such as K$_2$CO$_3$ (see *Tetrahedron Lett.* (1995), 36, 6373).
  2.6. Further general methods to remove amine protecting groups have been described in *Protecting Groups in Organic Synthesis*, 3$^{rd}$ Ed (1999), 494-653; T. W. Greene, P. G. M. Wuts; (Publisher: John Wiley and Sons, Inc., New York, N.Y.).

3. Leukart Reaction:
  The reaction is performed in formic acid or an inert high boiling solvent such as toluene or xylene at a temperature between 60° C. and 120° C. The resulting N-formamide intermediate is subsequently hydrolysed in acidic media such as aq HCl between 20° C. and 50° C.

4. Nitro Group Reduction:
  Typical reducing agents which can be used for such reaction are:
  4.1. an alkali metal hydride such as LAH or NaBH$_4$ in presence of CoCl$_2$ or NiCl$_2$, or a metal such as iron or zinc in acidic medium (HCl or AcOH); or
  4.2. hydrogen over Raney nickel or hydrogen or ammonium formate over a noble metal catalyst such as palladium on charcoal or platinum oxide.
  Further reagents such as aluminium amalgam, ferrous sulphate may also be used.

5. Mitsunobu Reaction:
  The alcohol is reacted with different nucleophiles such as phthalimide or hydrazoic acid, generated from NaN$_3$ in acidic medium, in presence of triphenylphosphine and diethyl or diisopropyl azodicarboxylate (DEAD or DIAD) in a solvent such as THF, DMF, DCM or DME between −20° C. and 60° C. as reviewed by O. Mitsunobu, in Synthesis (1981), 1. In the particular case of basic amines, the reaction is performed with the corresponding 2- or 4-nitro-phenylsulfonamides; the free amine is subsequently liberated as described in paragraph 2.4 above. The reaction might also be performed using a polymer-supported triphenylphosphine.

6. Mesylate, Tosylate or Triflate Formation:
  The alcohol is reacted with MsCl, TfCl or TsCl in presence of a base such as TEA in a dry aprotic solvent such as pyridine, THF or DCM between −30° C. and 50° C. In the case of the triflate or mesylate, Tf$_2$O or Ms$_2$O can also be used.

7. Reductive Amination:
  The reaction between the amine and the aldehyde or ketone is performed in a solvent system allowing the removal of the formed water through physical or chemical means (e.g. distillation of the solvent-water azeotrope or presence of drying agents such as molecular sieves, MgSO$_4$ or Na$_2$SO$_4$). Such solvent is typically toluene, Hex, THF, DCM or DCE or mixture of solvents such as MeOH-DCE. The reaction can be catalyzed by traces of acid (usually AcOH). The intermediate imine is reduced with a suitable reducing agent (e.g. NaBH$_4$, NaBHCN$_3$, or NaBH(OAc)$_3$ or through hydrogenation over a noble catalyst such as Pd/C. The reaction is carried out between −10° C. and 110° C., preferably between 0° C. and 60° C. The reaction can also be carried out in one pot. It can also be performed in protic solvents such as MeOH or water in presence of a picoline-borane complex (*Tetrahedron* (2004), 60, 7899-7906).

8. Conversion of an Ester into a Carboxylic Acid:
  When the ester side chain is a linear alkyl, the hydrolysis is usually performed by treatment with an alkali hydroxide such as LiOH, KOH or NaOH in a water-dioxan or water—THF mixture between 0° C. and 80° C. When the ester side chain is tert-butyl, the hydrolysis can also be performed in neat TFA or diluted TFA or HCl in an organic solvent such as ether or THF. When the ester side chain is the allyl group, the reaction is performed in presence of tetrakis(triphenylphosphine)palladium(0) in presence of an allyl cation scavenger such as morpholine, dimedone or tributyltin hydride between 0° C. and 50° C. in a solvent such as THF. When the ester side chain is benzyl, the reaction is performed under hydrogen in presence of a noble metal catalyst such as Pd/C in a solvent such as MeOH, THF or EA. Further strategies to introduce other acid protecting groups and general methods to remove them have been described in Protecting Groups in Organic Synthesis 3$^{rd}$ Ed; 1999, 369-441; T. W. Greene, P. G. M. Wuts; (Publisher: John Wiley and Sons, Inc., New York, N.Y.).

9. Curtius Reaction:

The reaction between the carboxylic acid and diphenylphosphoryl azide is performed in an inert solvent such as toluene between 50° C. and 110° C. The resulting isocyanate is trapped in situ with an alcohol such as benzyl, allyl or tert-butyl alcohol affording the corresponding Cbz, Alloc or Boc carbamates. Alternatively, the isocyanate can be hydrolyzed with water, affording the corresponding primary amine. Further detailed on this reaction can be obtained in T. Shioiri; *Compendium of Organic Synthesis* (1991), 6, 795-828.

10. Nitroaldol Reaction and Elimination:

The reaction between the aldehyde and the nitro derivative is performed in a solvent such as DCM or THF between 0° C. and 60° C. is presence of a basic catalyst such as ammonium acetate, TBAF or sodium methylate (*Tetrahedron. Lett.* (1996), 37, 987). In a second step, the intermediate nitroaldol compound is transformed into its corresponding nitroalkene derivative by elimination of water or after transformation of the alcohol into its corresponding chloride by reaction with thionyl chloride or into its corresponding mesylate followed by treatment with a base such as sodium methylate. Further details can be found in *Tetrahedron* (2001), 915-945.

11. Heck Reaction:

The unsaturated halide or triflate is reacted with an alkene and a strong base such as triethylamine, potassium carbonate, cesium carbonate or sodium acetate and an organopalladium catalyst such as tetrakis(triphenylphosphine)palladium(0), palladium chloride or palladium(II) acetate in a solvent such as DMF. The ligand is triphenylphosphine or BINAP. Further details can be obtained in R. F. Heck, *Org. React.* (1982), 27, 345-390 or A. de Meijere, F. E. Meyer, Jr., *Angew. Chem. Int. Ed. Engl.* (1994), 33(23-24), 2379-2411.

Preparation of the Compounds of Formula $I_H$:

General Preparation Methods:

The compounds of formula $I_H$ can be manufactured in accordance with the present invention by a) deprotecting, thanks to methods described in part 2 of the section "General reaction techniques", a compound of formula $II_H$

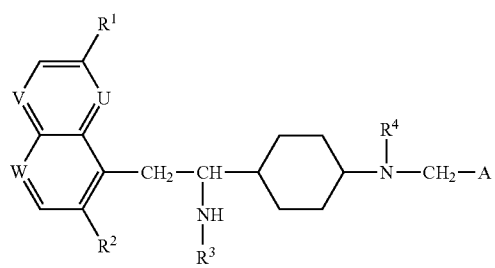

$II_H$ wherein $R^1$, $R^2$, U, V, W and A are as in formula I and

1. $R^3$ represents an amino protecting group such as COOR$^b$, COR$^c$, SO$_2$R$^d$ or benzyl, wherein R$^b$ is tert-butyl, allyl or benzyl, R$^c$ is (C$_1$-C$_4$)alkyl and R$^d$ represents 2-nitro-phenyl or 4-nitro-phenyl, and R$^4$ represents hydrogen (such compounds of formula II being referred to hereafter as "compounds of formula IIa"); or 2. $R^3$ represents hydrogen and R$^4$ represents an amino protecting group such as COOR$^e$, COR$^f$, SO$_2$R$^g$ or benzyl, wherein R$^e$ is tert-butyl, allyl or benzyl, R$^f$ is (C$_1$-C$_4$)alkyl and R$^g$ represents 2-nitro-phenyl or 4-nitro-phenyl (such compounds of formula II being referred to hereafter as "compounds of formula IIb"); or also 3. $R^3$ represents an amino protecting group such as COOR$^b$, COR$^c$, SO$_2$R$^d$ or benzyl, wherein R$^b$ is tert-butyl, allyl or benzyl, R$^c$ is (C$_1$-C$_4$)alkyl and R$^d$ represents 2-nitro-phenyl or 4-nitro-phenyl, and R$^4$ represents an amino protecting group such as COOR$^e$, COR$^f$, SO$_2$R$^g$ or benzyl, wherein R$^e$ is tert-butyl, allyl or benzyl, R$^f$ is (C$_1$-C$_4$)alkyl and R$^g$ represents 2-nitro-phenyl or 4-nitro-phenyl (such compounds of formula II being referred to hereafter as "compounds of formula IIc"); or b) reacting a compound of formula $III_H$

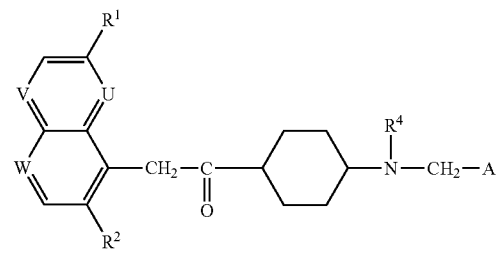

$III_H$ wherein $R^1$, $R^2$, U, V, W and A are as in formula I and $R^4$ is hydrogen or an amino protecting group as defined in a)2., with ammonium formate (which reaction is then preferably carried out using the conditions described in part 3 of the section "General reaction techniques") or ammonium acetate, hydroxylamine, alkyl or benzylhydroxylamine in presence of a hydride reagent such as LiAlH$_4$ or sodium cyanoborohydride, and, if applicable, removing the protecting group using methods described in part 2 of the section "General reaction techniques"; or c) reducing a compound of formula $IV_H$

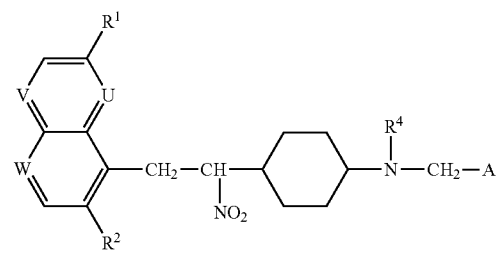

$IV_H$ wherein $R^1$, $R^2$, U, V, W and A are as in formula I and $R^4$ is hydrogen or an amino protecting group as defined in a)2. following one of the methods described in part 4 of the section "General reaction techniques";

and, if applicable, removing the protecting group using methods described in part 2 of the section "General reaction techniques"; or d) reducing a compound of formula $V_H$

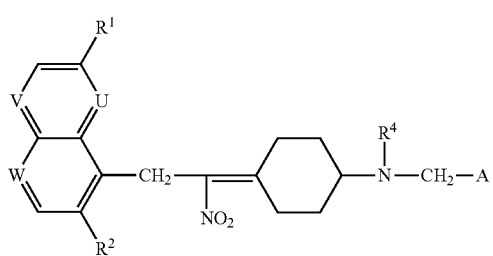

$V_H$ wherein $R^1$, $R^2$, U, V, W and A are as in formula I and $R^4$ is hydrogen or an amino protecting group as defined in a)2., following one of the methods described in paragraph 4.1 of the section "General reaction techniques", and, if applicable, removing the protecting group using methods described in part 2 of the section "General reaction techniques"; or e) reducing a compound of formula $VI_H$

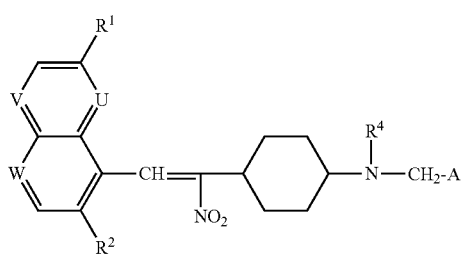

$VI_H$ wherein $R^1$, $R^2$, U, V, W and A are as in formula I and $R^4$ is hydrogen or an amino protecting group as defined in a)2., following one of the methods described in paragraph 4.1 of the section "General reaction techniques", and, if applicable, removing the protecting group using methods described in part 2 of the section "General reaction techniques"; or f) reacting a compound of formula $VII_H$

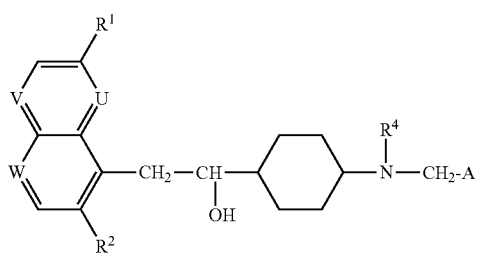

$VII_H$ wherein $R^1$, $R^2$, U, V, W and A are as in formula I and $R^4$ is hydrogen or an amino protecting group as defined in a)2. with sodium azide or phthalimide and subsequent transformation of the azide into an amine through reaction with $PPh_3$ in presence of water or transformation of the phthalimide into the corresponding amine through reaction with hydrazine, methyl hydrazine or an alkyl amine such as 3-N,N-dimethylaminopropylamine respectively, the reaction being performed either under Mitsunobu condition as described in part 5 of the section "General reaction techniques" or after transformation of the alcohol function of compounds of formula VII into a mesylate, triflate or tosylate as described in part 6 of the section "General reaction techniques", and, if applicable, removing the amino protecting group using methods described in part 2 of the section "General reaction techniques" (whereby the protecting group $R^4$ might also be removed during the reaction—for example, when $R^4$ is Cbz, it will be removed if a hydrogenolysis step is used); or g) reacting a compound of formula $VIII_H$

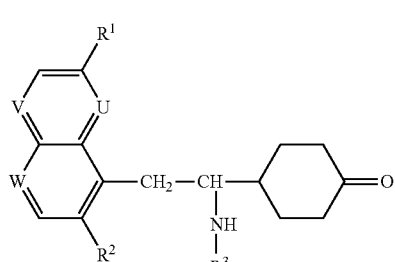

$VIII_H$ wherein $R^1$, $R^2$, U, V and W are as in formula I and $R^3$ is an amino protecting group as defined in a) 1. with a compound of formula IX $ACH_2NH_2$      IX wherein A is as in formula I under reductive amination conditions as described in part 7 of the section "General reaction techniques", and, if still present, removing the amino protecting group $R^3$ using methods described in part 2 of the section "General reaction techniques"; or h) reacting a compound of formula $X_H$

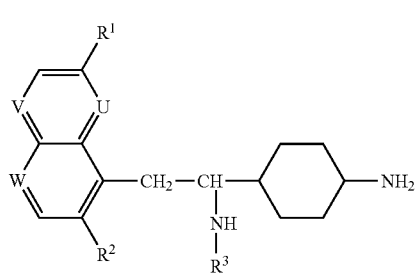

$X_H$ wherein $R^1$, $R^2$, U, V and W are as in formula I and $R^3$ is an amino protecting group as defined in a) 1. with a compound of formula XI

ACHO      XI wherein A is as in formula I under reductive amination conditions as described in part 7 of the section "General reaction techniques", and, if still present, removing the amino protecting group $R^3$ using methods described in part 2 of the section "General reaction techniques"; or i) reacting a compound of formula XII$_H$

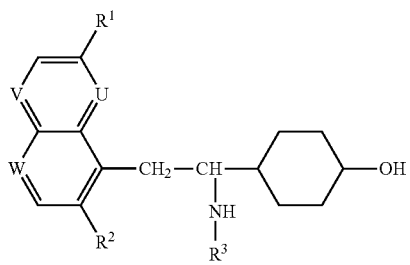

XII$_H$ wherein $R^1$, $R^2$, U, V and W are as in formula I and $R^3$ is an amino protecting group as defined in a)1. with a compound of formula IX after activation of either the alcohol function of compounds of formula XII as described in part 6 of the section "General reaction techniques" or the amine of formula IX as a 2-nitro- or 4-nitro-phenylsulphonamide and reaction under the conditions described in part 5 of the section "General reaction techniques" for basic amines, and, if still present, removing the amino protecting group $R^3$ using methods described in part 2 of the section "General reaction techniques"; or j) transforming a compound of formula II$_{Hest}$

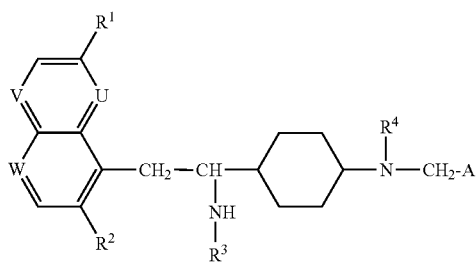

II$_{Hest}$ wherein U represents N, V represents CH, W represents $CR^a$, $R^a$ represents alkoxycarbonyl, $R^2$ represents H, $R^1$ and A are as in formula I and $R^3$ and $R^4$ are as defined in a) 1., a)2. or a)3. into its corresponding hydroxymethyl derivative by reduction with an hydride reagent such as DIBAH or LiAlH$_4$ and subsequent removal of the protecting groups.

Concerning variants d) and e) of the above process, it should be noted that, as an alternative, compounds of formula V and VI can be reduced to their corresponding saturated nitro derivatives of formula IV by reduction of the double bond using NaBH$_4$ in aq. THF as described in *Tetrahedron Lett.* (2003), 7345 and can be further converted into compounds of formula I by reduction of the nitro derivative following one of the methods described in paragraph 4.1 of the section "General reaction techniques".

The compounds of formula I$_H$ obtained according to the abovementioned general preparation methods may then, if desired, be converted into their salts, and notably into their pharmaceutically acceptable salts.

Compounds of formula I$_H$ with controlled stereochemistry at the carbon bearing the free amine group are obtained through separation of the two enantiomers by crystallisation with a chiral acid such as camphorsulfonic acid, by separation of the racemic mixture on a chiral column or by separation of the diastereomeric carbamates obtained from the amines and a chiral chloroformate such as (−)-menthyl chloroformate either by crystallization or on a non-chiral column. The compounds can also be obtained either from compounds of formula II-17 described later on wherein the stereochemistry at the carbon bearing the hydroxyl group is controlled, as described in variant f) of the above process or through enantioselective reduction of a compound of formula III$_H$ or its corresponding oximes or imines using for example chiral boron reagents as reviewed in *Chem. Rev.* (1993), 93, 763.

Preparation of the Various Synthesis Intermediates:

Preparation of the Compounds of Formula II$_H$

The intermediates of formula IIa can be obtained as summarized in Scheme 1 hereafter.

Scheme 1

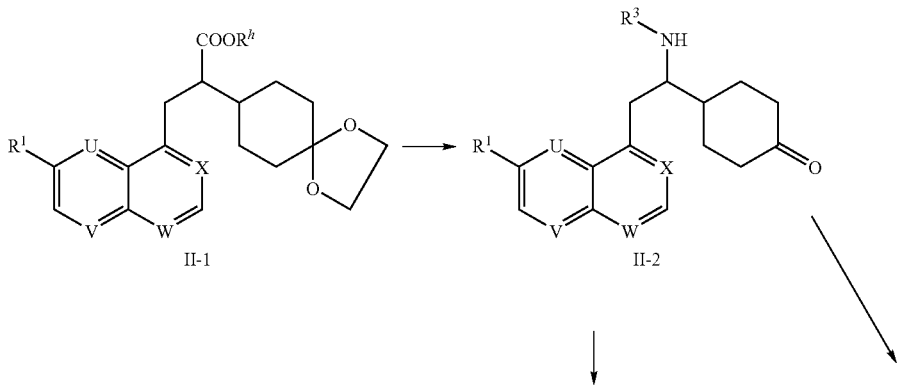

II-1    II-2

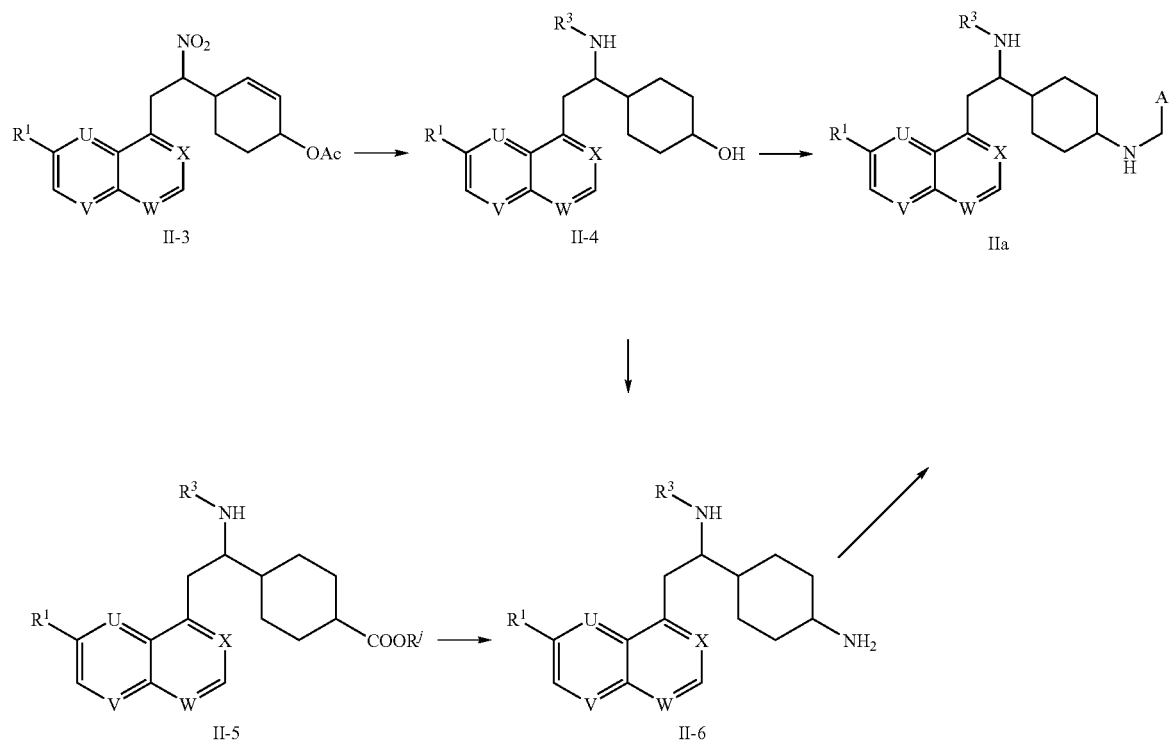

In Scheme 1, U, V, W and A have the same meaning as in formula I, $R^3$ is as described in formula IIa, X represents $CR^2$ and $R^2$ is as defined in formula I, $R^h$ is alkyl or benzyl and $R^j$ is alkyl or benzyl.

Compounds of formula IIa can be obtained (Scheme 1) through reductive amination of the ketones of formula II-2 with an amine of formula IX, substitution of the alcohols of formula II-4 with an amine of formula IX or through alkylation or reductive amination of the amines of formula II-6 with an halogenide of formula $ACH_2Hal$ wherein Hal is an halogen such as bromine or iodide, or an aldehyde of formula XI respectively. The substitution of the alcohol of formula II-4 can be performed after transformation of the alcohol into its mesylate (see part 6 of the section "General reaction techniques") and optionally into its corresponding iodide after reaction of the said mesylate with NaI; alternatively, the alcohol of formula II-4 can be reacted with the 2- or 4-nitrophenylsulfonamide derived from the amine of formula IX (as explained in part 5 of the section "General reaction techniques" for basic amines). The alkylation of the amines of formula II-6 is performed in a solvent such as THF or DCM in presence of a base such as $Na_2CO_3$ or TEA. The amine derivatives of formula II-6 can also be obtained from the alcohol of formula I-4 through reaction with hydrazoic acid under Mitsunobu conditions (see part 5 of the section "General reaction techniques") followed by reduction with $PPh_3$/water. They can further be obtained from the ketone of formula II-2 through reductive amination (see part 7 of the section "General reaction techniques") with ammonium acetate or benzylamine followed in the latter case through a hydrogenation step.

The ketone of formula II-2 is obtained from ketal of formula II-1 as detailed hereafter. After deprotection of the ester function of the ketal of formula II-1 (see part 8 of the section "General reaction techniques"), the resulting acid is transformed into its corresponding protected amine using a Curtius reaction (see part 9 of the section "General reaction techniques") or a variant thereof and finally the ketal group is removed upon mild acidic treatment such as PTSA in an aq. org. solvent such as THF or MeOH, or acetone. The reaction can also be performed using a polymer-supported reagent such as IR120.

The alcohol of formula II-4 is obtained from the corresponding nitro derivatives of formula II-3 as detailed hereafter. The nitro derivative of formula II-3 is reduced (see part 4 of the section "General reaction techniques") into the corresponding saturated amine, which is protected as a carbamate, a N-benzyl or a N-acetyl derivative (see part 1 of the section "General reaction techniques"). The protecting OAc group if still in place is subsequently removed by treatment with aq. $Na_2CO_3$ in MeOH or THF. Alternatively the alcohol of formula II-4 is obtained from the corresponding ketone derivatives of formula II-2 through reduction with a hydride reagent such as $NaBH_4$.

The amine derivatives of formula II-6 are obtained from the ester derivatives of formula II-5 after sequential hydrolysis into the corresponding acid followed by a Curtius reaction followed by hydrolysis of the intermediate isocyanate with water (see part 9 of the section "General reaction techniques").

The ketals of formula II-1 can be obtained as summarized in Scheme 2 hereafter.

Scheme 2

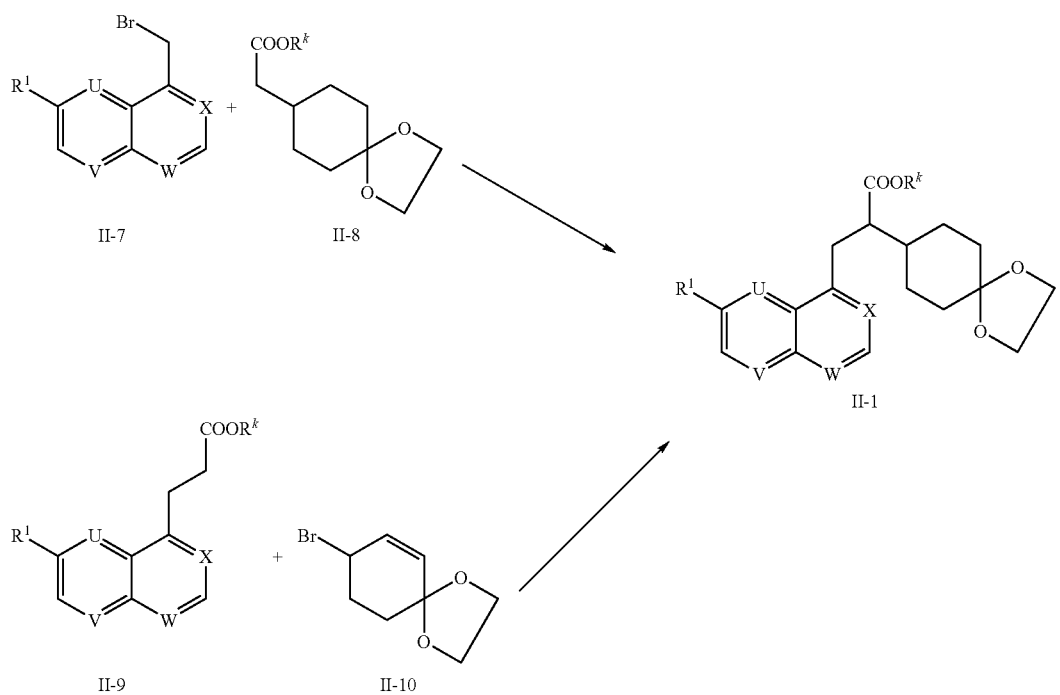

In Scheme 2, U, V and W have the same meaning as in formula I, X represents $CR^2$, $R^2$ being as defined in formula I and $R^k$ represents alkyl or benzyl.

The ketals of formula II-1 can be obtained (Scheme 2) by reaction of the anions of the acetate derivatives of formula II-8, which are generated with an organic base such as LDA or LiHMDS in a dry a protic solvent between −70° C. and −30° C., with the bromomethyl derivatives of formula II-7. These derivatives are prepared either through bromination of the corresponding methyl derivatives as described in WO 2006/046552 (U═N) or WO 2006/093253 (W═N) by treatment with NBS or bromine or through the transformation of the corresponding aldehydes obtained according to WO 2006/032466 or WO 2006/021448 into their benzyl alcohols through reduction with a borohydride reagent such as $NaBH_4$ and subsequent transformation into their corresponding bromo derivatives by reaction with $PBr_3$. Alternatively, the ketal of formula II-1 can be obtained by reaction of the anion generated by the reaction of the ester derivatives II-9 with an organic base such as LDA or LiHMDS in a dry aprotic solvent such as THF between −78° C. and −30° C. on the bromo derivatives of formula II-4 (prepared according to U.S. Pat. No. 5,536,725). The ester derivatives of formula II-9 can be obtained in a two-step process, which two-step process consists in the reaction of the triethylphosphonoacetate anion with the required aldehydes (e.g. according to *J. Am. Chem. Soc.* (1961), 83, 1733) followed by catalytic hydrogenation over a noble catalyst such as Pd/C. Alternatively, the ester derivatives of formula II-9 can be obtained using a Heck reaction (see part 11 of the section "General reaction techniques") involving the derivatives of formula II-11

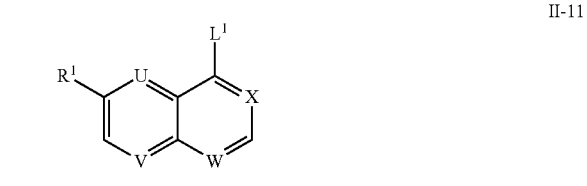

wherein U, V and W have the same meaning as in formula I, X represents $CR^2$, $R^2$ is as defined in formula I and $L^1$ is $OSO_2CF_3$ or halogen (preferably iodide or bromine), and the appropriate acrylate derivatives, followed by catalytic hydrogenation over a noble catalyst (e g. Pd/C).

The intermediates of formula II-3 can be obtained as summarized in Scheme 3 hereafter.

Scheme 3

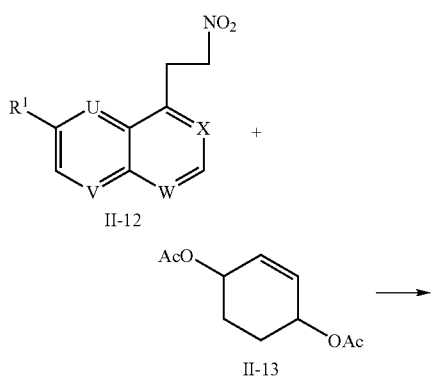

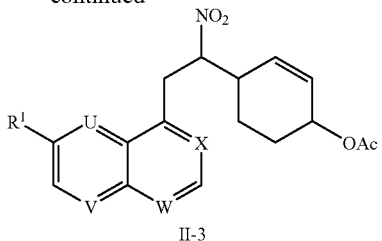

II-3

In Scheme 3, $R^1$, U, V and W have the same meaning as in formula I, X represents $CR^2$, $R^2$ being as defined in formula I.

The nitro derivatives of formula II-3 can be obtained (Scheme 3) by reaction between 1,4-diacetoxy-2-cyclohexene (compound of formula II-13; prepared according to WO 2003/051887) and the nitro derivative of formula II-12 via a palladium catalyzed asymmetric allylic alkylation using a Pd(0) catalyst such as tris(dibenzylideneacetone)dipalladium-chloroform complex and a diphenylphosphino benzoic acid based chiral ligand as described in *Angew. Chem. Int. Ed.* (2000), 3122. The nitro derivative of formula II-12 can be prepared by a tandem nitroaldol and elimination reaction (see part 10 of the section "General reaction techniques") between the corresponding aldehydes and nitromethane, followed by reduction using methods described earlier (e.g. hydrogenation over Pd/C).

The intermediates of formula IIb can be obtained as summarized in Scheme 4 hereafter.

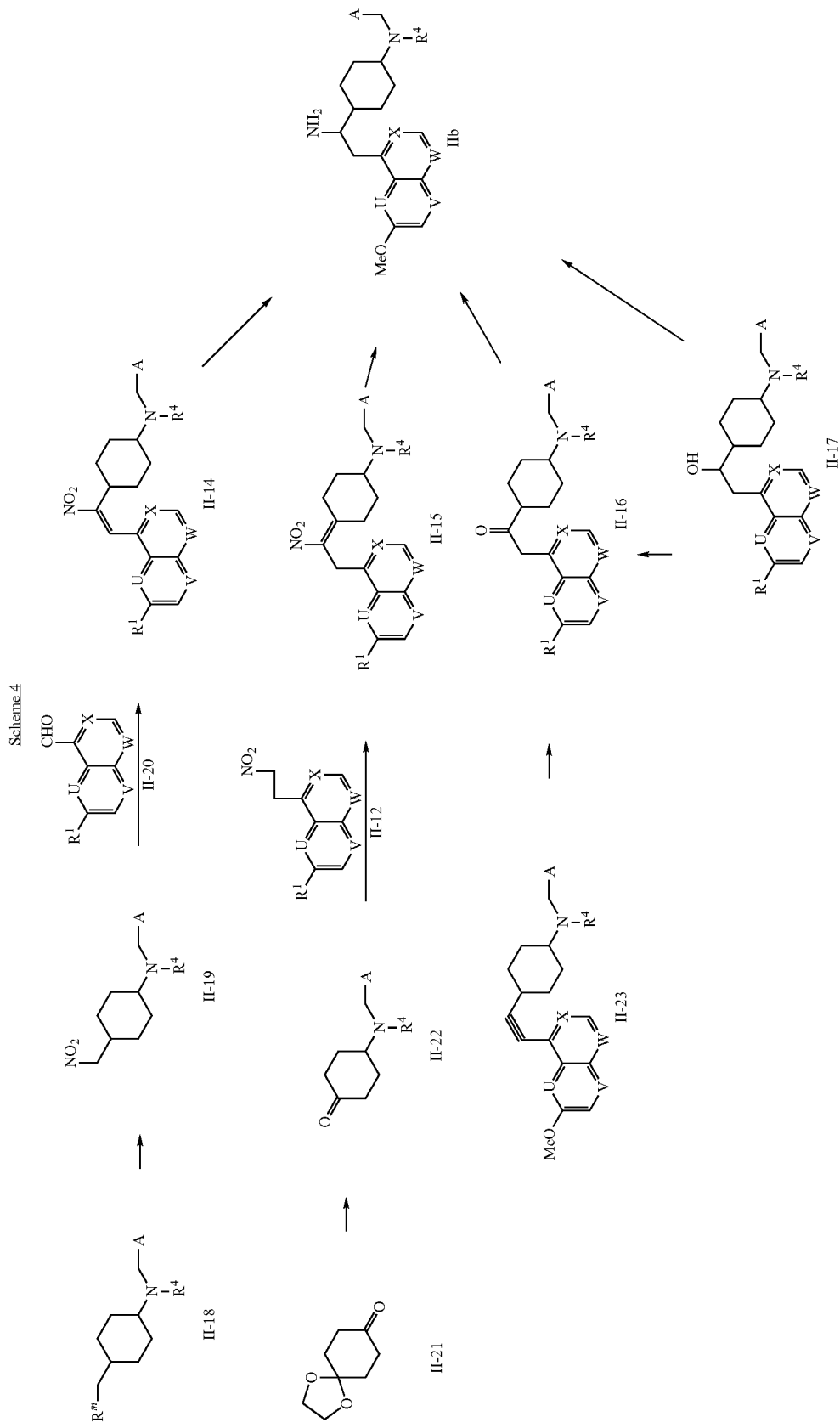

In Scheme 4, $R^1$, U, V, W and A have the same meaning as in formula I, X represents $CR^2$, $R^2$ being as defined in formula I, $R^4$ represents hydrogen or an amino protecting group as in the compounds of formula IIb, $R'''$ represents OH, $OSO_2R''$ or I and $R''$ represents Me, tolyl or $CF_3$.

Compounds of formula IIb can be obtained (Scheme 4) through reduction of the nitro derivatives of formula II-14 or II-15 like in variant f) or g) of the "General preparation methods" or through reductive amination of the ketones of formula II-16 (see part 7 of the section "General reaction techniques") or through the substitution of the alcohols of formula II-17 with azides under Mitsunobu conditions (see part 5 of the section "General reaction techniques") followed by hydrogenation over a noble catalyst such as Pd/C.

Compounds of formula II-14 can be obtained by nitroaldol reaction (see part 10 of the section "General reaction techniques") of the aldehydes of formula II-20 with the nitro derivatives of formula II-19. The latter derivatives can be obtained from the corresponding alcohols of formula II-18 ($R'''$=OH) after sequential transformation into its corresponding mesylate, tosylate or triflate of formula II-18 ($R'''$=$OSO_2R''$; $R''$=Me, tosyl or $CF_3$), reaction with NaI in a polar solvent such as acetone between 20° C. and 80° C. (compounds of formula II-18 wherein $R'''$=I) and reaction with sodium nitrite in a polar solvent such as THF, DMSO or DMF between 20° C. and 80° C. in presence of a base such as TEA or urea.

Compounds of formula II-15 can be obtained through a tandem nitroaldol elimination reaction of the ketones of formula II-22 with the nitro derivatives of formula II-12 (see part 10 of the section "General reaction techniques"). Compounds of formula II-22 can be obtained by reductive amination of reaction of 1,4-dioxaspiro[4.5]decan-8-one (the compound of formula II-21) with an amine of formula IX as defined earlier (see part 7 of the section "General reaction techniques"), subsequent deprotection of the ketal in acidic medium (e.g. diluted AcOH or hydrochloric acid) and final protection of the amine function with a Boc or Cbz group (preferably Boc; see paragraph 1.1 of the section "General reaction techniques").

Compounds of formula II-16 can be obtained either through oxidation of the corresponding alcohols II-17 using standard oxidation procedures such as Swern, Dess-Martin periodinate reactions or Ley's oxidation procedure using tetrapropylammonium perruthenate (*Synthesis* (1994), 7, 639-66), or through hydratation of the alkyne derivatives of formula II-23 as described in WO 2006/032466.

A possible preparation route for the alcohols of formula II-17 is summarised in Scheme 5 hereafter.

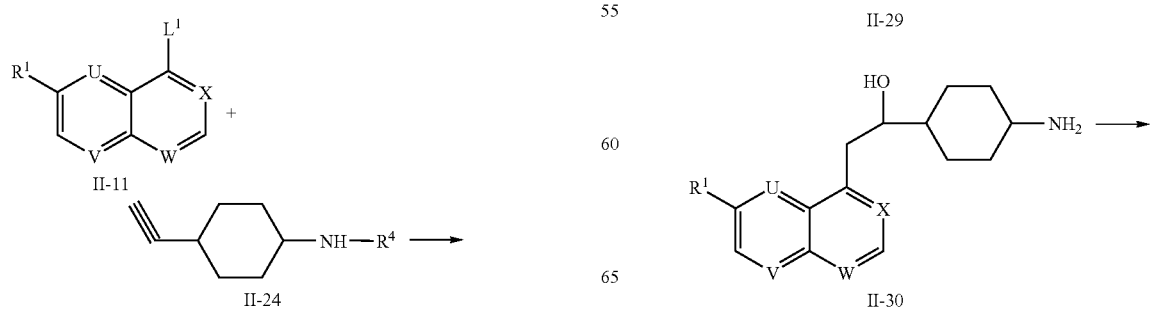

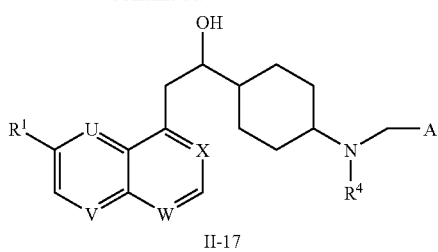

II-17

In Scheme 5, $L^1$ is $OSO_2CF_3$ or a halogen atom (preferably Br or Cl), $R^4$ is an amino protecting group as in the compounds of formula IIb (in particular Cbz or Boc), X represents $CR^2$, $R^2$ being as defined in formula I, and $R^1$, U, V, W and A have the same meanings as in formula I.

The compounds of formula II-17 can be obtained (Scheme 5) from compounds II-30 through reductive amination with an amine of formula IX (see part 7 of the section "General reaction techniques"). The intermediates of formula II-25 may be obtained from the compounds of formula II-11 mentioned earlier and the terminal alkyne derivatives of formula II-24. The alkynes of formula II-24 and the 4-trifluoromethanesulfonates of formula II-11 ($L^1=OSO_2CF_3$) can be coupled under Sonogashira conditions using catalytic amount of a palladium salt, an organic base such as TEA and a catalytic amount of a copper derivative (usually copper iodide) in a solvent such a DMF between 20° C. to 100° C. (see Sonogashira, K. in *Metal-Catalyzed Reactions*, Diedrich, F., Stang, P. J., Eds; Wiley-VCH: New York 1998). The resulting alkynes of formula II-25 can be hydrogenated to form the alkene of formula II-26 using methods reviewed by Siegel, S. et al. in *Comprehensive Organic Synthesis*, B. M. Trost, I. Fleming, Eds; Pergamon Press: New York (1991), vol. 8, p. 417-470. The (E)-alkenes of formula II-26 can be transformed into the corresponding chiral cis-diol derivative of formula II-27 by treatment with AD mixtures in presence of methanesulfonamide in a water/2-methyl-2-propanol mixture as described in *Chem. Rev.* (1994), 94, 2483. The sense of induction relies on the chiral ligand contained in the mixture, either a dihydroquinine-based ligand in AD-mix α or a dihydroquinidine-based ligand in AD-mix β. The chiral cis-diols of formula II-27 can be transformed into the corresponding cyclic carbonate of formula II-28 by treatment either with phosgene, diphosgene or triphosgene in presence of an organic base such as TEA or pyridine, or with carbonyldimidazole in an inert solvent such as DCM or THF at a temperature ranging between −78° C. and 50° C., and preferably at a temperature ranging between 0° C. and 20° C. The cyclic carbonates of formula II-28 can subsequently be transformed into the homobenzylic alcohols of formula II-29 by hydrogenolysis using a catalytic system such as Pd/C in presence of hydrogen in a solvent such as EA. The intermediates of formula IV-7 can be further transformed into compounds of formula II-17 by sequential removal of the protecting group $R^4$ (see part 2 of the section "General reaction techniques") to give the compound of formula II-30, reductive amination (see part 7 of the section "General reaction techniques") and reinstallation of the protecting group $R^4$ (see part 1 of the section "General reaction techniques").

The alkyne derivatives of formula II-24 can be prepared as shown in Scheme 6 hereafter.

Scheme 6

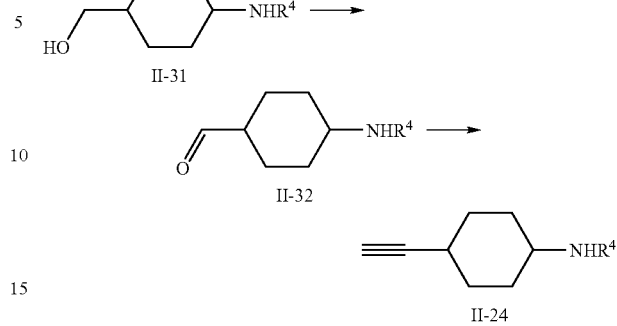

In Scheme 6, $R^4$ is an amino protecting group as defined in formula IIb (in particular Cbz or Boc).

The alkyne derivatives of formula II-24 can generally be obtained (Scheme 6) from the suitable alcohols of formula II-31 (e.g. those wherein $R^4$ is Boc), which can be converted first into the aldehydes of formula II-32 using for example the Moffat-Swern (see Synthesis (1981), 165), or the Dess-Martin periodinane (see *J. Am. Chem. Soc.* (1991), 113, 7277) oxidation protocols. The aldehyde is converted into the corresponding alkyne using either the Corey-Fuchs protocol (formation of the gem-dibromide then treatment with n-BuLi) as described in *Tetrahedron Letters* (1972), 3769 or using dimethyl-2-oxopropylphosphonate diazo derivative (so called Ohira's reagent, *Synth. Comm.* (1989), 19, 561) or dimethyldiazomethylphosphonate as described in *Synlett* (2003), 59 and *Synlett* (1996), 521.

An alternative reaction that can be used to obtain the (E)-alkenes of formula II-26 is shown in Scheme 7 hereafter.

Scheme 7

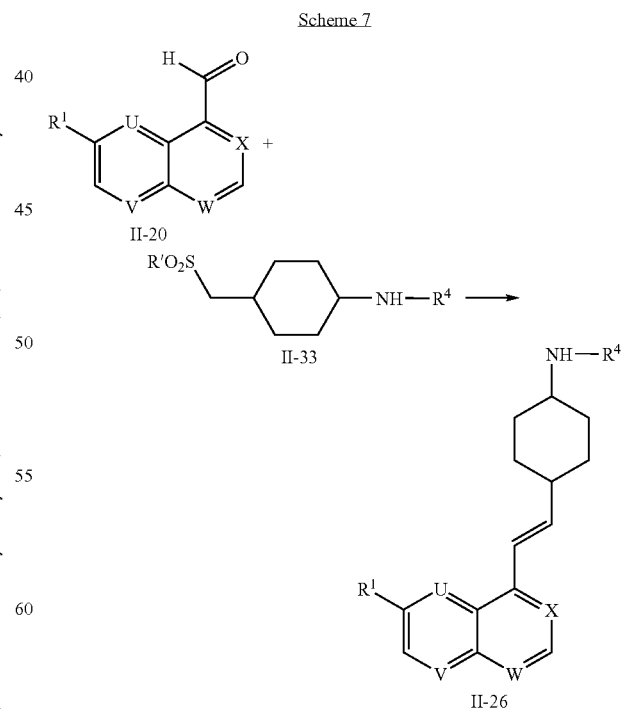

In Scheme 7, R' is 1-phenyl-1H-tetrazol-5-yl or benzothiazol-2-yl, $R^4$ is an amino protecting group as in the compounds of formula IIb (in particular Cbz or Boc), X represents $CR^2$, $R^2$ being as defined in formula I, and $R^1$, U, V and W have the same meanings as in formula I.

Accordingly, the compounds of formula II-26 can be obtained (Scheme 7) as (E)-isomers from the aldehyde derivatives of formula II-20 and the sulfones of formula II-33 after reaction in presence of KHMDS or LiHMDS in a solvent such as 1,2-DME, DMF or toluene between −78° C. and 0° C. as reviewed by Blakemore, P. R in *J. Chem. Soc., Perkin Trans.* 1 (2002), 2563-2585. The sulfones of formula II-33 can be obtained from the corresponding alcohol derivatives of formula II-31 (see Scheme 6) via a Mitsunobu coupling (see part 5 of the section "General reaction techniques") with 1-phenyl-1H-tetrazole-5-thiol or benzothiazol-2-thiol. An alternate route to form the intermediate sulphide requires the activation of the alcohols of formula II-31 as for example tosylates, triflates or mesylates (see part 6 of the section "General reaction techniques"). Once activated, the alcohols of formula II-31 can react with NaI or KI in acetone at a temperature ranging between 0° C. and 65° C., to form the corresponding iodides. The latter serve as alkylating agents of 1-phenyl-1H-tetrazole-5-thiol. The alkylation reaction is performed in presence of an inorganic base such as KOH or NaOH in a solvent such as EtOH at a temperature ranging between −20° C. and 70° C. The resulting intermediate sulfide derivatives were further oxidized into the corresponding sulfones of formula II-33. A wide range of oxidizing agents may be used to perform such a reaction, such as MCPBA in a solvent such as DCM, Oxone® in a solvent such as aq. MeOH (see *Tetrahedron Lett.* (1981), 22, 1287), or aq. hydrogen peroxide in presence of ammonium heptamolybdate tetrahydrate in EtOH (see *J. Org. Chem.* (1963), 28, 1140).

A further route to the (E)-alkenes of formula II-26 is shown in Scheme 8 hereafter.

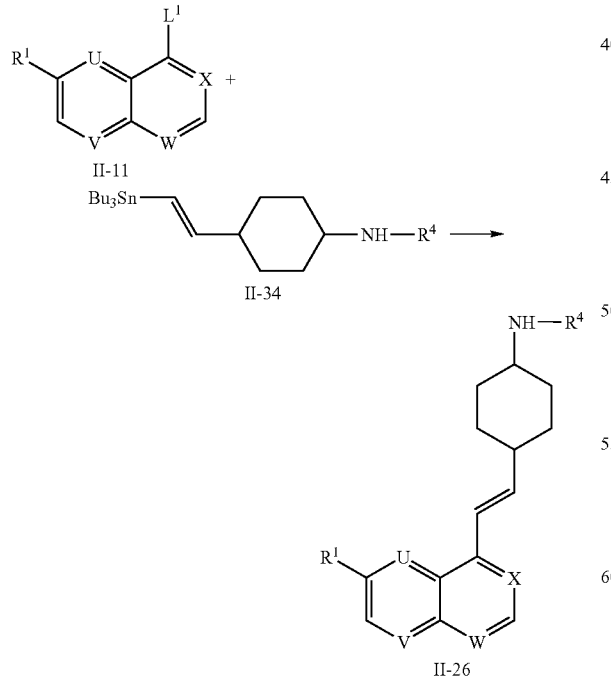

In Scheme 8, $L^1$ is $OSO_2CF_3$ or halogen, $R^4$ is an amino protecting group as in the compounds of formula IIb (in particular Cbz or Boc), X represents CH and $R^1$, U, V and W have the same meanings as in formula I.

Pursuant to this route, the 4-trifluoromethanesulfonate derivative of formula II-11 ($L^1=OSO_2CF_3$) can be coupled (Scheme 8) with the organostannane of formula II-34 deriving from the terminal alkyne derivative of formula II-24 (see Scheme 5) to yield the (E)-alkene of formula II-26. Indeed, hydrostannation reaction of the alkyne derivative of formula II-24 using tributyl tin hydride and a catalytic amount of either a palladium salt or a molybdenum complex generates an E:Z mixture of the vinylstannane intermediate as described in *J. Org. Chem.* (1990), 55, 1857. The vinylstannane is reacted with a 4-trifluoromethanesulfonate derivative of formula II-11 under Stille coupling conditions (as described in *J. Am. Chem. Soc.* (1987), 109, 5478). Typical reaction conditions involve a palladium(0) source such as tetrakis(triphenylphosphine) palladium or dichloro bis(triphenylphophine)palladium, LiCl and a radical scavenger such as 2,6-dimethyl-4-methylphenol in a solvent such as DMF or dioxane at a temperature ranging between 0° C. and 100° C., more preferably at a temperature ranging between 20° C. and 80° C. As the reaction proceeds normally at a faster rate using (E)-vinylstannane, the resulting (E)-alkene of formula II-26 is usually obtained with a high isomeric purity.

An alternative preparation method for obtaining the compounds of formula II-29 is summarised in Scheme 9 hereafter.

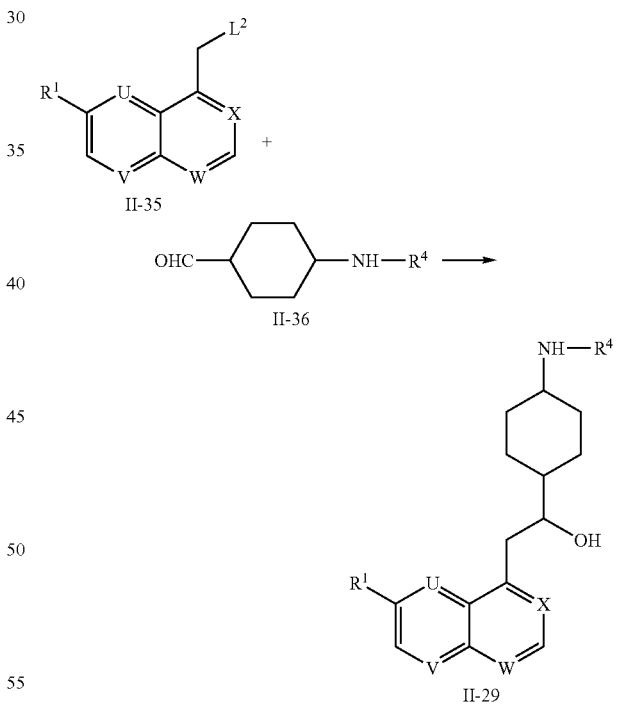

In Scheme 9, $L^2$ is MgCl, MgBr, Li or K, $R^4$ is an amino protecting group as in the compounds of formula IIb (in particular Cbz or Boc), X represents $CR^2$, $R^2$ being as defined in formula I, and $R^1$, U, V and W have the same meanings as in formula I.

As illustrated in Scheme 9, the compounds of formula II-29 can also be obtained by reacting the aldehyde derivative of formula II-36 either with a Grignard reagent of formula II-35 ($L^2$=MgCl, MgBr) in a dry solvent such as ether or THF between 0° C. and 60° C. or with a lithium or potassium derivative of formula II-35 (L²=Li, Na or K) in a solvent such as THF or ether between −78° C. and 20° C.

The intermediates of formula IIc can be obtained as summarized in Scheme 10 hereafter.

Preparation of the Compounds of Formula $V_H$

The intermediates of formula $V_H$ are actually intermediates of formula II-15 described earlier (see Scheme 4).

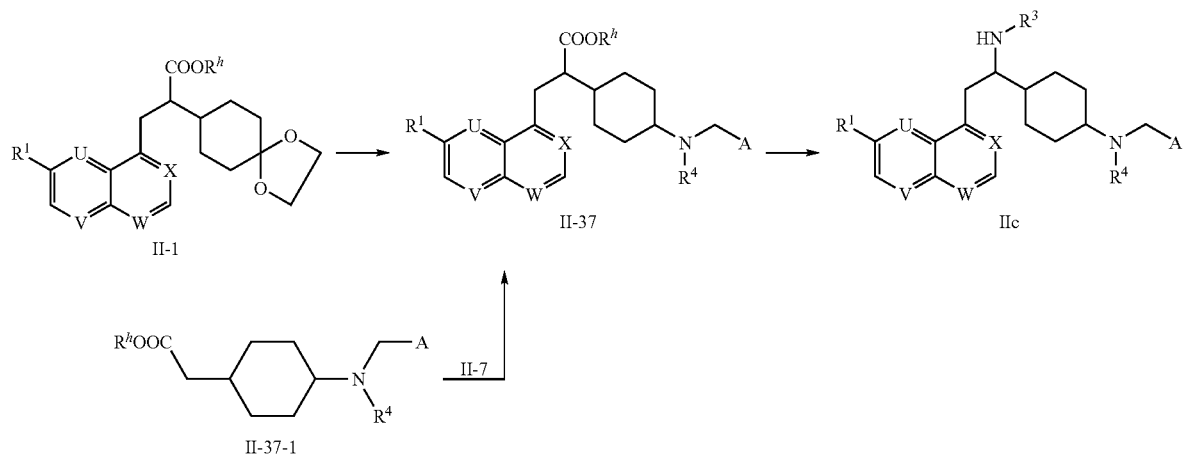

In Scheme 10, U, V, W and A have the same meaning as in formula I, $R^3$ and $R^4$ are amino protecting groups as defined in formula IIc (in particular Cbz or Boc), X represents $CR^2$, $R^2$ being as defined in formula I, $R^h$ is alkyl or benzyl and $R^1$, U, V and W have the same meanings as in formula I.

The compounds of formula IIc can be obtained (Scheme 10) by transforming the corresponding ester of formula II-37 into the corresponding protected amine derivative using a Curtius reaction or a variant thereof (see part 9 of the section "General reaction techniques"); in case water is used for quenching, an amine protection step is carried out after the Curtius reaction (see part 1 of the section "General reaction techniques"). The ester of formula II-37 can be obtained from the intermediate of formula II-1 by acidic deprotection of the ketal, followed by a reductive amination with an amine of formula IX as defined earlier (see part 7 of the section "General reaction techniques") and protection of the amine function as a carbamate (e.g. Boc or Cbz), as a N-benzyl derivative or as a N-acetyl derivative (see part 1 of the section "General reaction techniques"). The compounds of formula II-37 can also be obtained by reacting the bromo derivatives of formula II-7 with the esters of formula II-37-1 (following the method described for the formation of compounds of formula II-1, starting from the compounds of formula II-7; Scheme 10). The intermediates of formula II-37-1 are obtained by deprotection of the ketals of formula II-8 followed by reductive amination with the compounds of formula IX (ACH₂NH₂) (see part 7 of the section "General reaction techniques") and final protection of the secondary amine (see part 1 of the section "General reaction techniques").

Preparation of the Compounds of Formula $III_H$

The intermediates of formula $III_H$ are actually intermediates of formula II-16 described earlier (see Scheme 4).

Preparation of the Compounds of Formula $IV_H$

The intermediates of formula $IV_H$ can be made starting from compounds of formula V or from compounds of formula $VI_H$ as already described in the section "General preparation methods".

Preparation of the Compounds of Formula $VI_H$

The intermediates of formula $VI_H$ are actually intermediates of formula II-14 described earlier (see Scheme 4).

Preparation of the Compounds of Formula $VII_H$

The intermediates of formula $VII_H$ are actually intermediates of formula II-17 described earlier (see Scheme 3).

Preparation of the Compounds of Formula $VIII_H$

The intermediates of formula $VIII_H$ are actually intermediates of formula II-2 described earlier (see Scheme 1).

Preparation of the Compounds of Formula $X_H$

The intermediates of formula $X_H$ are actually intermediates of formula II-6 described earlier (see Scheme 1).

Preparation of the Compounds of Formula $XII_H$

The intermediates of formula $XII_H$ are actually intermediates of formula II-4 described earlier (see Scheme 1).

Preparation of the Compounds of Formula $II_{Hest}$

The intermediates of formula $II_{Hest}$ can be obtained by the same routes as the compounds of formula $II_H$.

Preparation of the Starting Quinoline, [1,5]-Naphthyridine and Quinoxaline Derivatives:

The required starting quinoline, [1,5]-naphthyridine and quinoxaline derivatives of formula II-7, II-11, II-20 or II-35 are prepared following literature procedures.

The compounds of formula II-7 wherein U=W=N, V=CH and R² is H, wherein U=V=N, W=CH and R² is H, wherein U=W=N, V=CH and R² is F or wherein W=N, U=V=CH and R² is F can be obtained by reduction of the known corresponding aldehydes of formula II-20 using an hydride reagent such as NaBH₄ in a solvent such as THF or MeOH and subsequent reaction with PBr₃ in a solvent such as DMF between 0° C. and 60° C.

The compounds of formula II-11 wherein U=V=N and R²=H can be obtained by reaction of the corresponding phenol derivative (wherein L¹ would be OH instead of OSO₂CF₃ or halogen) which can be prepared according to WO 2004/002490 using PBr₃ as described earlier.

The aldehyde of formula II-20 wherein W=N and R² is F can be obtained from the known corresponding quinoline derivative of formula II-38

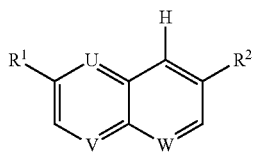

II-38 wherein $R^1$, U and V are as defined in formula I through reaction of the anion generated with a strong organic base such as LDA or alkyllithium such as n-BuLi, between −78° C. and −20° C. with DMF as described in *J. Org. Chem.* (1980), 45, 1514.

Compounds of formula II-35 wherein $L^2$ is MgBr are prepared from the corresponding derivatives of formula II-7 by reaction with magnesium in a dry solvent such as ether between 0° C. and 60° C.

Preparation of the Compounds of Formula $I_{OH}$:
General Preparation Methods:

The compounds of formula $I_{OH}$ can be manufactured in accordance with the present invention by
a) deprotecting, thanks to methods described in part 2 of the section "General reaction techniques", a compound of formula $II_{OH}$

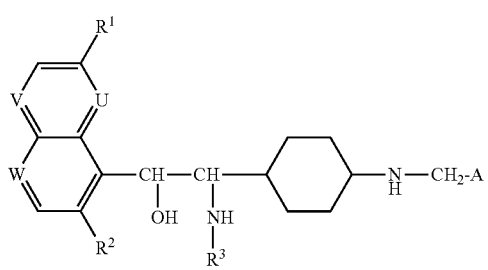

$II_{OH}$ wherein $R^1$, $R^2$, U, V, W and A are as in formula I and $R^3$ represents an amino protecting group such as $COOR^b$, $COR^c$, $SO_2R^d$ or benzyl, wherein $R^b$ is tert-butyl, allyl, benzyl or 9-fluorenylmethyl, $R^c$ is ($C_1$-$C_4$)alkyl and $R^d$ represents 2-nitro-phenyl or 4-nitro-phenyl; or
b) treating a compound of formula $III_{OH}$

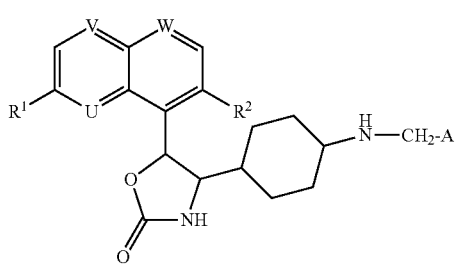

$III_{OH}$ wherein $R^1$, $R^2$, U, V, W and A are as in formula I with an inorganic base such as LiOH or Ba(OH)$_2$.

Compounds of formula $I_{OH}$ with controlled stereochemistry at the carbons bearing the free amine and hydroxy groups are obtained through separation of the diastereomers by crystallisation with a chiral acid such as camphorsulfonic acid, by separation of the diastereomeric mixture on a chiral column or by separation of the diastereomeric carbamates obtained from the amines and a chiral chloroformate such as (−)-menthyl chloroformate either by crystallization or on a non-chiral column.

Preparation of the Various Synthesis Intermediates:
Preparation of the Compounds of Formula $II_{OH}$ The intermediates of formula $II_{OH}$ can be obtained as summarized in Scheme 11 hereafter.

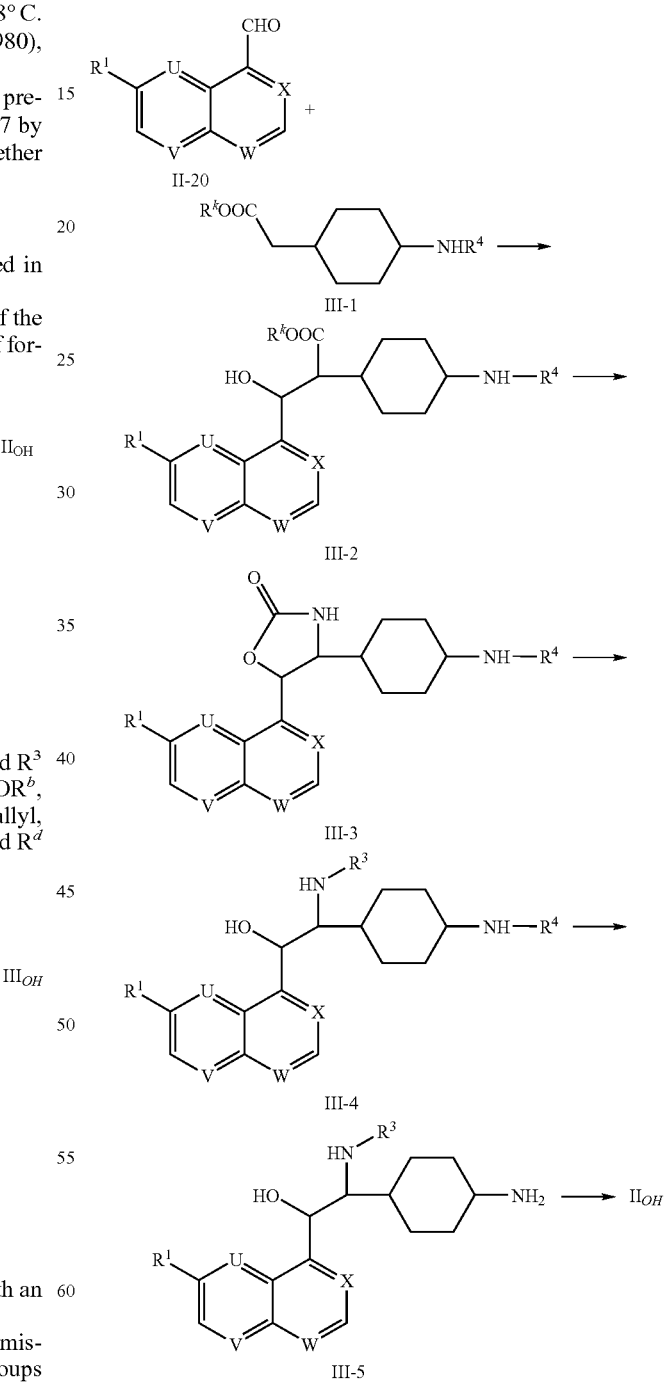

Scheme 11

In Scheme 11, $R^1$, U, V and W have the same meanings as in formula I, X represents $CR^2$, $R^2$ being as defined in formula I, R⁴ is an amino protecting group such as Boc or Cbz, R³ is an amino protecting group such as Fmoc, R^k represents a lower alkyl such as methyl or ethyl.

The anion obtained by the action of a strong organic base such as LiHMDS between −80° C. and −40° C. on the ester of formula III-1 (prepared according to WO 00/24717) can be reacted with the aldehyde of formula II-20, generating the hydroxyester of formula III-2. This ester can be transformed into the corresponding acid by saponification and further reaction with DPPA between 20° C. and 100° C., leading to the oxazolidinone of formula III-3. Further treatment with an inorganic base such as LiOH or Ba(OH)₂ leads to the formation of the corresponding aminoalcohol which can be protected to give the intermediate of formula III-4. Selective removal of the protecting group R⁴ affords the compound of formula III-5 which can be converted into the compound of formula III$_{OH}$ after reductive amination with the aldehyde of formula XI (see above) as described in part 7 of the section "General reaction techniques".

Preparation of the Compounds of Formula III$_{OH}$

The intermediates of formula III$_{OH}$ can be obtained as summarized in Scheme 12 hereafter.

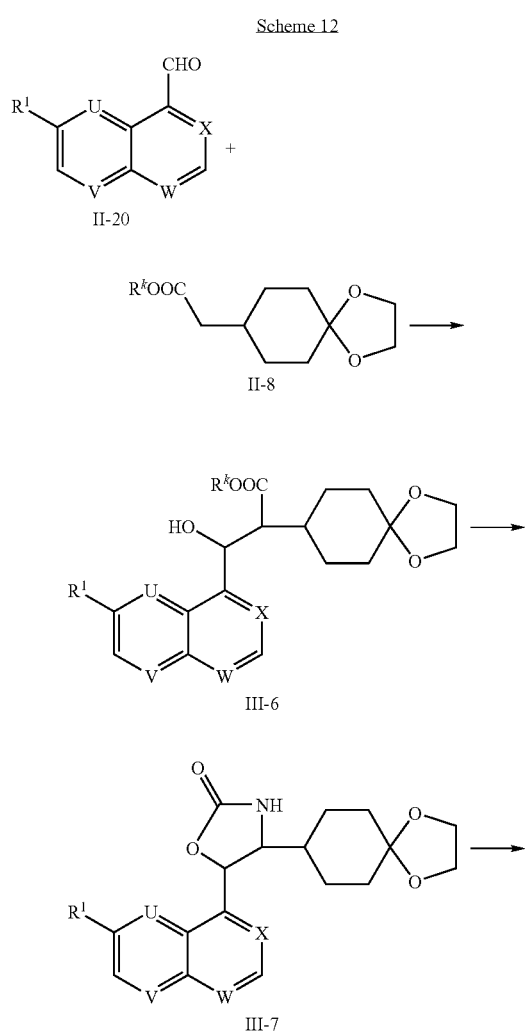

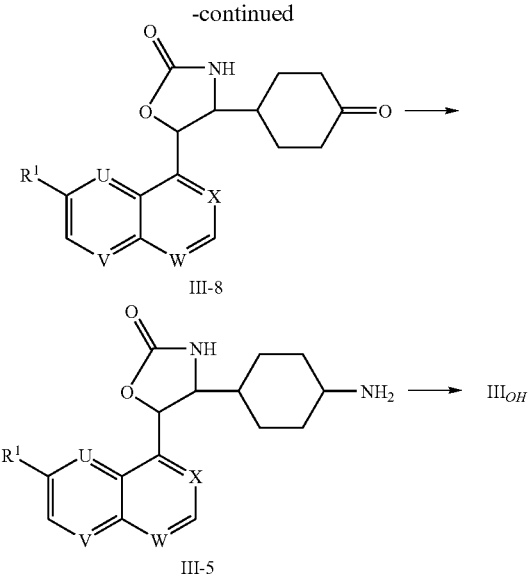

In Scheme 12, R¹, U, V and W have the same meanings as in formula I, X represents CR², R² being as defined in formula I, R^k represents a lower alkyl such as methyl or ethyl.

The anion obtained by the action of a strong organic base such as LiHMDS between −80° C. and −40° C. on the ester of formula II-8 can be reacted with the aldehyde of formula II-20, generating the hydroxyester of formula III-6. This ester can be transformed into the corresponding acid by saponification and further reaction with DPPA between 20° C. and 100° C., leading to the oxazolidinone of formula III-7. The ketal protecting group can be removed under acidic treatment and the resulting ketone be subjected to reductive amination with ammonium acetate as described in part 7 of the section "General reaction techniques", leading to the amine derivative of formula III-5 which can in turn be subjected to reductive amination with the aldehyde of formula XI (see above) as described in part 7 of the section "General reaction techniques", affording the compound of formula III$_{OH}$.

Particular embodiments of the invention are described in the following Examples, which serve to illustrate the invention in more detail without limiting its scope in any way.

EXAMPLES

All temperatures are stated in ° C. All analytical and preparative HPLC investigations on non-chiral phases are performed using RP-C18 based columns.

Preparation A: (E)-3-(2,5-difluoro-phenyl)-propenal

A.i. (E)-3-(2,5-difluoro-phenyl)-acrylic acid ethyl ester

To an iced chilled suspension of NaH (1.13 g, 60% in oil dispersion, 28.2 mmol) in THF (32 mL) was added triethylphosphonoacetate (5.6 ml, 28.2 mmol). The reaction mixture was stirred at rt for 20 min. 2,5-difluoro-benzaldehyde (3.34 g, 23.5 mmol) was added drop wise. After 30 min, 10% aq. NaHSO₄ (100 mL) was added and the mixture was diluted with EA (150 mL). The two phases were separated and the aq. layer was extracted twice with EA (2×100 mL). The combined org. layers were washed with brine (100 mL), dried over Na₂SO₄, filtered and concentrated to dryness. The residue was chromatographed over SiO$_2$ (Hex-EA 19-1) to afford the title ester (5.0 g, 100% yield) as a colourless oil.

$^1$H NMR (CDCl$_3$) δ: 7.76 (dd, J=1, 16.1 Hz, 1H); 7.26-7.21 (m, 1H); 7.13-7.03 (m, 2H); 6.52 (d, J=16.1 Hz, 1H); 4.29 (q, J=7.1 Hz, 2H); 1.36 (t, J=7.1 Hz, 3H).

A.ii. (E)-3-(2,5-difluoro-phenyl)-prop-2-en-1-ol

To a solution of intermediate A.i (5.0 g, 23.5 mmol) in ether (100 ml), cooled to 0° C., was added a solution of DIBAH (1M in Hex, 60 ml, 60 mmol). The mixture was stirred at the same temperature for 40 min. Water (6 ml) was added and the mixture was stirred 30 min. The solid was filtered off and thoroughly washed with ether. The filtrate was concentrated to dryness to afford the title alcohol (4.0 g, 98% yield) as a colourless oil.

$^1$H NMR (CDCl$_3$) δ: 7.15 (ddd, J=3.1, 5.9, 9.0 Hz, 1H); 7.00 (td, J=4.6, 9.0 Hz, 1H); 6.95-6.87 (m, 1H); 6.75 (dd, J=1.3, 16.1 Hz, 1H); 6.45 (td, J=5.3, 16.1 Hz, 1H); 4.38 (br d, J=5.3 Hz, 2H); 1.63 (s, 1H).

A.iii. (E)-3-(2,5-difluoro-phenyl)-propenal

To a solution of intermediate A.ii (1.70 g, 10 mmol) in DCM (20 ml) was added at rt, a solution of Dess-Martin periodinane (15 wt % in DCM, 20 ml). The mixture was stirred at rt for 3 h. After concentration to dryness, the residue was chromatographed over SiO$_2$ (Hex-EA 9-1) to afford the title aldehyde (1.06 g, 63% yield) as a white solid.

$^1$H NMR (d6-DMSO) δ: 9.74 (d, J=7.6 Hz, 1H); 7.88-7.81 (m, 1H); 7.79 (overlapped dd, J=1.4, 16.0 Hz, 1H); 7.46-7.37 (m, 2H); 6.67 (dd, J=7.6, 16.0 Hz, 1H).

Example 1

6-(trans-{4-[(1R)-1-amino-2-(6-methoxy-[1,5]naphthyridin-4-yl)-ethyl]-cyclohexylamino}-methyl)-4H-pyrido[3,2-b][1,4]thiazin-3-one 1.i. Toluene-4-sulfonic acid trans-4-tert-butoxycarbonylamino-cyclohexylmethyl ester To an ice-chilled solution of trans-(4-hydroxymethyl-cyclohexyl)-carbamic acid tert-butyl ester (7.06 g, 30.8 mmol) in DCM (120 mL) and THF (30 mL) were added TEA (8.5 mL, 2 eq.) and p-TsCl (7 g, 1.2 eq.). The mixture was then stirred at rt overnight. DMAP (1 g) was added and the reaction proceeded for 2 h. Saturated NaHCO$_3$ (100 ml) was added. The org. layer was further washed with saturated CuSO$_4$ (2×100 mL), water (100 mL) and brine. The org. layer was then concentrated to dryness. The resulting solid was filtered off, washed with water and dried under vacuum. The title tosylate was obtained as a white solid (11.7 g, 99% yield).

MS (ESI, m/z): 384.3 [M+H]$^+$.

1.ii. trans-(4-iodomethyl-cyclohexyl)-carbamic acid tert-butyl ester

To a solution of intermediate 1.i (11.7 g, 30.5 mmol) in acetone (100 mL) was added NaI (13.7 g, 3 eq.). The solution was heated at 60° C. overnight. The reaction mixture was concentrated to dryness and the residue was taken up in water, filtered off and the solid was thoroughly washed with water. The solid was collected and dried under HV to afford the title iodide as a white solid (10.2 g, 98% yield).

MS (ESI, m/z): 340.1 [M+H]$^+$.

1.iii. trans-[4-(1-phenyl-1H-tetrazol-5-ylsulfanylmethyl)-cyclohexyl]-carbamic acid tert-butyl ester To a solution of 1-phenyl-1H-tetrazole-5-thiol (5.84 g, 32.8 mmol) in EtOH (65 mL) was added powdered KOH (2 g, 35.7 mmol) and the resulting mixture was stirred 1 h under reflux. Intermediate 1.ii (10.1 g, 29.8 mmol) was then added and the reaction stirred at reflux overnight. The reaction mixture was cooled to rt and concentrated to dryness. The residue was resuspended in water, filtered, washed with water, and dried to a constant weight (11.15 g, 96% yield).

$^1$H NMR (d6-DMSO) δ: 7.66 (br s, 5H); 6.70 (br d, J=7.9 Hz, 1H); 3.24 (d, J=6.8 Hz, 2H); 3.18 (m, 1H); 1.82-1.75 (m, 4H); 1.58 (m, 1H); 1.36 (s, 9H); 1.36-1.01 (m, 4H).

MS (ESI, m/z): 340.1 [M+H]$^+$.

1.iv. trans-[4-(1-phenyl-1H-tetrazole-5-sulfonylmethyl)-cyclohexyl]-carbamic acid tert-butyl ester To a stirred solution of intermediate 1.iii (11.2 g, 28.6 mmol) in EtOH (265 mL) was added at rt a solution of ammonium molybdate heptahydrate (4.4 g, 3.6 mmol) in 30% aq. H$_2$O$_2$ (38 mL). The reaction was stirred at rt for 3 h, before heating at 75° C. for 1 h. The solvent was carefully removed under reduced pressure and the solid was diluted with water, filtered and washed with water. The title sulfone was further dried to a constant weight (11.0 g, 91% yield).

$^1$H NMR (CDCl$_3$) δ: 7.63-7.49 (m, 5H); 4.82 (br s, 1H); 4.30 (m, 1H); 3.60 (d, J=6.0 Hz, 2H); 3.35 (m, 1H); 2.06-1.96 (m, 4H); 1.36 (s, 9H); 1.28-1.04 (m, 4H).

1.v. {4-[(E)-2-(6-methoxy-[1,5]naphthyridin-4-yl)-vinyl]-cyclohexyl}-carbamic acid tert-butyl ester To a solution of intermediate 1.iv (14 g, 33.2 mmol) (14 g, 33.2 mmol) and 6-methoxy-[1,5]naphthyridine-4-carbaldehyde (6.56 g, 34.8 mmol) in 1,2-DME (150 mL), cooled to −78° C., was added drop wise a solution of KHMDS (100 mL, 0.5M in toluene, 49.82 mmol) over 1 h. The reaction mixture was stirred 1 h at this temperature before warming to rt. After further stirring for 1 h, the reaction was quenched with brine (75 mL). The two layers were separated and the aq. layer was extracted with EA (3×100 mL). The combined org. layers were dried over MgSO$_4$, filtered and concentrated to dryness. The residue was triturated in Hept-ether (1-1, 300 mL), filtered and dried under HV to afford the title compound as a beige powder (9.25 g, 73% yield).

$^1$H NMR (CDCl$_3$) δ: 8.70 (d, J=2.8 Hz, 1H); 7.96 (d, J=8.1 Hz, 1H); 7.62-7.49 (m, 3H); 6.94 (d, J=15.4 Hz, 1H); 6.19 (dd, J=7.1, 15.4 Hz, 1H); 4.42 (m, 1H); 3.99 (s, 3H); 3.49 (m, 1H); 2.22 (m, 1H); 2.19-2.10 (m, 2H); 2.00-1.95 (m, 2H); 1.48 (s, 9H); 1.48-1.34 (m, 2H); 1.30-1.21 (m, 2H).

MS (ESI, m/z): 383.3 [M+H]$^+$.

1.vi. trans-{4-[(1S,2S)-1,2-dihydroxy-2-(6-methoxy-[1,5]naphthyridin-4-yl)-ethyl]-cyclohexyl}-carbamic acid tert-butyl ester To a solution of intermediate 1.v (9.25 g, 24.1 mmol) in 2-methyl-2-propanol (100 mL) and water (100 mL) were added methanesulfonamide (2.6 g, 26.5 mmol) and AD-mix α (37 g). The resulting mixture was stirred at rt overnight. Sodium bisulfite (36 g) was added portion wise. After stirring for 20 min, the two layers were decanted. The aq. layer was further extracted with EA (150 mL). The combined org. layers were dried over MgSO$_4$, filtered and concentrated to dryness. The residue was chromatographed (EA to EA-MeOH 9:1) to afford the title diol as a beige solid (6.86 g, 68% yield).

$^1$H NMR (d6-DMSO) δ: 8.75 (d, J=4.5 Hz, 1H); 8.25 (d, J=9.0 Hz, 1H); 7.74 (d, J=4.5 Hz, 1H); 7.24 (d, J=9.0 Hz, 1H); 6.81 (br s, 1H); 6.68 (d, J=7.9 Hz, 1H); 5.70 (dd, J=1.6, 6.6 Hz, 1H); 5.24 (d, J=6.6 Hz, 1H); 4.17 (d, J=8.0 Hz, 1H); 3.99 (s, 3H); 3.47 (td, J=2.0, 8.0 Hz, 1H); 3.17 (br s, 1H); 2.09-1.96 (m, 2H); 1.84-1.76 (m, 2H); 1.48 (m, 1H); 1.37 (s, 9H); 1.23-0.93 (m, 3H).

1.vii. trans-{4-[(4S,5S)-5-(6-methoxy-[1,5]naphthyridin-4-yl)-2-oxo-[1,3]dioxolan-4-yl]-cyclohexyl}-carbamic acid tert-butyl ester To an ice-chilled solution of intermediate 1.vi (6.86 g, 16.4 mmol) in DCM (100 mL) were added pyridine (7.93 mL, 98.5 mmol) and triphosgene (2.49 g, 8.2 mmol) portion wise. The reaction was stirred 30 min at this temperature and then 30 min at rt. The reaction mixture was diluted with a sat. NaHCO$_3$ and the two layers were decanted. The aq. layer was extracted once with DCM (100 mL) and the combined org. layers were dried over MgSO$_4$, filtered, and concentrated to dryness to afford the title compound as an orange foam (6.81 g, 94% yield).

$^1$H NMR (d6-DMSO) δ: 8.83 (d, J=4.5 Hz, 1H); 8.32 (d, J=9.0 Hz, 1H); 7.82 (d, J=4.5 Hz, 1H); 7.32 (d, J=9.0 Hz, 1H); 6.70 (d, J=8.1 Hz, 1H); 6.09 (d, J=6.0 Hz, 1H); 4.80 (t, J=6.0 Hz, 1H); 3.99 (s, 3H); 3.13 (m, 1H); 1.88-1.68 (m, 5H); 1.38 (s, 9H); 1.18-1.13 (m, 4H).

MS (ESI, m/z): 444.0 [M+H$^+$].

1.viii. trans-{4-[(1R)-1-hydroxy-2-(6-methoxy-[1,5]naphthyridin-4-yl)-ethyl]-cyclohexyl}-carbamic acid tert-butyl ester To a solution of intermediate 1.vii (3.7 g, 8.34 mmol) in EA (50 mL) was added 20% Pd(OH)$_2$/C (moisturized, 1.8 g). The mixture was stirred under hydrogen atmosphere for 3 h. The reaction mixture was diluted with EA (100 mL) and MeOH (20 mL). The catalyst was removed by filtration and the filtrate was concentrated to dryness. The residue was chromatographed (DCM-MeOH 93-7 containing 0.3% aq. NH$_4$OH) to afford the title compound as a white solid (1.9 g, 56% yield).

$^1$H NMR (CDCl$_3$) δ: 8.68 (d, J=4.2 Hz, 1H); 8.21 (d, J=9.0 Hz, 1H); 7.39 (d, J=4.2 Hz, 1H); 7.12 (d, J=9.0 Hz, 1H); 4.37 (m, 1H); 4.23 (m, 1H); 4.06 (s, 3H); 3.75 (m, 1H); 3.40-3.20 (m, 3H); 2.11-1.91 (m, 4H); 1.44 (s, 9H); 1.40-1.15 (m, 5H).

MS (ESI, m/z): 402.0 [M+H$^+$].

1.ix. trans-{4-[(1R)-1-hydroxy-2-(6-methoxy-[1,5]naphthyridin-4-yl)-ethyl]-cyclohexyl}-carbamic acid benzyl ester A solution of intermediate 1.viii (1.9 g) in TFA (10 mL) was stirred at rt for 15 min. The solvent was removed in vacuo and the residue was dissolved in 2N NaOH until a white emulsion formed. The aq. layer was extracted three times with DCM-MeOH (9-1, 3×100 mL). The combined org. layers were washed with brine, dried over Na$_2$SO$_4$, filtered and concentrated to dryness. The residue was taken up in acetone (25 mL) and water (15 mL) and cooled to 0° C. NaHCO$_3$ (0.8 g) and Cbz-Cl (0.75 mL) were added. The mixture was stirred overnight at rt. The solvent was removed in vacuo. The resulting solid was filtered off, washed with water and dried under HV to afford the title compound as a white solid (1.55 g).

$^1$H NMR (d6-DMSO) δ: 8.63 (d, J=4.2 Hz, 1H); 8.21 (d, J=9.0 Hz, 1H); 7.52 (d, J=4.2 Hz 1H); 7.37-7.28 (m 5H); 7.22 (d, J=9.0 Hz 1H); 7.11 (d, J=7.8 Hz, 1H); 4.98 (s, 2H); 4.43 (d, J=6.3 Hz, 1H); 3.99 (s, 3H); 3.69 (m, 1H); 3.53 (dd, J=2.7, 12.3 Hz, 1H); 3.21 (m, 1H); 2.77 (dd, J=9.3, 13.2 Hz, 1H); 1.93-1.76 (m, 4H); 1.22-1.10 (m, 5H).

1.x. Trans-{4-[2-(6-methoxy-[1,5]naphthyridin-4-yl)-acetyl]-cyclohexyl}-carbamic acid benzyl ester To a solution of intermediate 1.ix (3.0 g, 6.88 mmol) in DCM (20 mL) cooled to 0° C. was added dropwise DIPEA (3.5 mL, 3 eq.). A mixture of sulfur trioxide pyridine complex (2.7 g, 48%, 8.26 mmol) in DMSO (8.5 mL) was then added dropwise. The reaction mixture was stirred overnight at rt. The volatiles were removed under reduced pressure and water was added. The precipitate was filtered, washed with water and taken up in DCM (200 mL). The org. layer was washed with brine, dried over Na$_2$SO$_4$, filtered and concentrated to dryness. The residue was purified by column chromatography (DCM-MeOH 93-7) to afford the tilte ketone as a yellowish solid (1.45 g, 48% yield).

$^1$H NMR (d6-DMSO) δ: 8.69 (d, J=4.5 Hz, 1H); 8.24 (d, J=9.0 Hz, 1H); 7.51 (d, J=4.5 Hz, 1H); 7.35-7.26 (m, 5H); 7.24 (d, J=9.0 Hz, 1H); 7.18 (d, J=7.8 Hz, 1H); 4.32 s, 2H); 3.92 (s, 3H); 3.23 (m, 1H); 2.53 (m, 1H); 1.67 (m, 2H); 1.87 (m, 2H); 1.39-1.13 (m, 4H).

MS (ESI, m/z): 434.0 [M+H$^+$].

1.xi. (RS)-trans-{4-[1-amino-2-(6-methoxy-[1,5]naphthyridin-4-yl)-ethyl]-cyclohexyl}-carbamic acid benzyl ester To a solution of intermediate 1.x (1.45 g, 3.33 mmol) in MeOH (25 mL) were added ammonium acetate (6.5 g, 25 eq.) and sodium cyanoborohydride (0.251 g, 4 mmol). The reaction mixture was stirred at rt overnight and then concentrated to dryness. The residue was partitioned between saturated NaHCO$_3$ (100 mL) and DCM-MeOH (9-1, 150 mL). The phases were separated and the aq. layer extracted once more with DCM-MeOH 9-1. The combined org. layers were dried over MgSO$_4$, filtered and evaporated to dryness. The residue was purified by column chromatography (DCM-MeOH 93-7 containing 0.7% aq. NH$_4$OH) to afford the title amine as a white solid (1.04 g, 71% yield). MS (ESI, m/z): 435.3 [M+H$^+$].

1.xii. (RS)-[trans-1-(4-amino-cyclohexyl)-2-(6-methoxy-[1,5]naphthyridin-4-yl)-ethyl]-carbamic acid tert-butyl ester To a solution of intermediate 1.xi. (1.0 g, 2.3 mmol) in DCM (20 mL) were added triethylamine (0.64 mL, 2 eq.) and di-tert-butyl-dicarbonate (0.75 g, 1.5 eq.). The reaction was stirred at rt for 3 h. The reaction was concentrated to dryness and the residue was triturated in Hept. The solid was filtered off, dried under HV to afford the title compound (1.05 g) as white solid. The latter was taken up in EA (60 mL) and MeOH (15 mL), warmed to 45° C. and 20% Pd(OH)$_2$/C (moisturized, 0.5 g) was added. The reaction was stirred under hydrogen atmosphere for 1 h. The catalyst was removed by filtration and the filtrate was concentrated to dryness, further dried under HV to afford the title amine as a white solid (0.78 g).

MS (ESI, m/z): 401.3 [M+H$^+$].

1.xiii. (RS)-(trans-2-(6-methoxy-[1,5]naphthyridin-4-yl)-1-{4-[(3-oxo-3,4-dihydro-2H-pyrido[3,2-b][1,4]thiazin-6-ylmethyl)-amino]-cyclohexyl}-ethyl)-carbamic acid tert-butyl ester To a solution of intermediate 1.xii (0.783 g, 1.95 mmol) in 1,2-DCE (35 mL) and MeOH (12 mL) were added 3-oxo-3,4-dihydro-2H-pyrido[3,2-b][1,4]thiazine-6-carbaldehyde (0.417 g, 1.1 eq) and molecular sieves 3 Å (7.8 g). The mixture was heated at 50° C. overnight. The mixture was cooled to 0° C., and NaBH$_4$ (0.6 g) was added in one portion. The reaction was stirred 40 min at 0° C. and diluted with DCM-MeOH (9-1, 20 mL). The mixture was filtered and the solids were washed with DCM-MeOH (9-1, 300 mL) and DCM (100 mL). The org. layer was washed with sat. NaHCO$_3$ (50 mL). The org. layer was dried over Na$_2$SO$_4$, filtered and concentrated to dryness. The residue was chromatographed (DCM-MeOH 93-7 containing 0.7% aq. NH$_4$OH) to afford the title compound as a white solid (0.93 g).

$^1$H NMR (d6-DMSO) (major rotamer) δ: 10.81 (s, 1H); 8.60 (d, J=4.5 Hz, 1H); 8.20 (d, J=9.0 Hz, 1H); 7.70 (d, J=8.1 Hz, 1H); 7.46 (d, J=4.5 Hz, 1H); 7.21 (d, J=9.0 Hz, 1H); 7.07 (d, J=8.1 Hz, 1H); 6.61 (d, J=9.3 Hz, 1H); 4.01 (s, 3H); 3.71 (br s, 2H); 3.70 (overlapped m, 1H); 3.56 (dd, J=3.0, 12.0 Hz, 1H); 3.50 (s, 2H); 2.74 (t, J=11.4 Hz, 1H); 2.31 (m, 1H); 1.95-1.79 (m, 5H); 1.35 (m, 1H); 1.13 (s, 9H); 1.12-1.00 (m, 5H).

MS (ESI, m/z): 579.2 [M+H$^+$].

1.xiv. (1R)-(trans-2-(6-methoxy-[1,5]naphthyridin-4-yl)-1-{4-[(3-oxo-3,4-dihydro-2H-pyrido[3,2-b][1,4]thiazin-6-ylmethyl)-amino]-cyclohexyl}-ethyl)-carbamic acid tert-butyl ester and (1S)-(trans-2-(6-methoxy-[1,5]naphthyridin-4-yl)-1-{4-[(3-oxo-3,4-dihydro-2H-pyrido[3,2-b][1,4]thiazin-6-ylmethyl)-amino]-cyclohexyl}-ethyl)-carbamic acid tert-butyl ester Starting from intermediate 1.xiii (0.05 g), dissolved in MeOH (25 mL), both enantiomers (0.023 g of each) were obtained enantiomerically pure after separation by chiral HPLC using a Chiralpk AD 4.6×250 mm, 5 μm column at ambient temperature. The eluent used was an EtOH (containing 0.1% of diethylamine)-Hex (90-10) mixture and the flow rate was 0.8 mL/min.

The first eluting enantiomer, hereafter called intermediate 1.xiv.a, came after 13.11 min (maximum intensity recorded at a wavelength of 210 nm).

The second eluting enantiomer, hereafter called intermediate 1.xiv.b, came after 21.23 min. (maximum intensity recorded at a wavelength of 210 nm).

1.xv. 6-(trans-{4-[(1R)-1-amino-2-(6-methoxy-[1,5]naphthyridin-4-yl)-ethyl]-cyclohexylamino}-methyl)-4H-pyrido[3,2-b][1,4]thiazin-3-one A solution of intermediate 1.xiv.a (0.023 g) in TFA (8 mL) was stirred at rt for 25 min. The solvent was evaporated and the mixture was taken up in sat. NaHCO$_3$ (40 mL) and 1M NaOH (4 mL). The mixture was extracted with DCM-MeOH (9-1, 200 mL). The org. layer was dried over Na$_2$SO$_4$, filtered and concentrated to dryness. The residue was triturated in ether to afford the title amine as an off-white solid (0.018 g).

MS (ESI, m/z): 479.2 [M+H$^+$].

Example 2

6-(trans-{4-[(1S)-1-amino-2-(6-methoxy-[1,5]naphthyridin-4-yl)-ethyl]-cyclohexylamino}-methyl)-4H-pyrido[3,2-b][1,4]thiazin-3-one 2 Different Preparation Methods were Used to Obtain the Compound of Example 2

Method A:

Starting from intermediate 1.xiv.b (0.023 g), the title enantiomer was obtained as an off-white solid (0.018 g) using the procedure described in Example 1, step 1.xv. The compound was triturated in ether.

MS (ESI, m/z): 479.2 [M+H$^+$].

Method B:

2.B.i. Methanesulfonic acid (1R)-trans-1-(4-benzyloxycarbonylamino-cyclohexyl)-2-(6-methoxy-[1,5]naphthyridin-4-yl)-ethyl ester To a ice-chilled mixture of intermediate 1.ix (1.3 g, 2.98 mmol) in DCM (30 mL) were added TEA (0.83 mL, 2 eq.), DMAP (0.036 g, 0.1 eq.) and MsCl (0.3 mL, 1.3 eq.). The reaction was stirred 15 min. at 0° C. and then 1 h at rt. Saturated NaHCO$_3$ (100 mL) was added. The two layers were decanted and the org. layer was dried over Na$_2$SO$_4$, filtered and concentrated to dryness. The residue was chromatographed (DCM-MeOH 97-3) to afford the title mesylate (1.5 g, 97% yield) as a white foam.

MS (ESI, m/z): 514.2 [M+H$^+$].

2.B.ii. trans-{4-[(1S)-1-azido-2-(6-methoxy-[1,5]naphthyridin-4-yl)-ethyl]-cyclohexyl}-carbamic acid benzyl ester To a solution of intermediate 2.B.i (1.48 g, 2.88 mmol) in DMF (20 mL) was added sodium azide (0.6 g). The mixture was stirred at 80° C. for 3 h. Water (200 mL) was added and. the resulting mixture was extracted with ether (4×75 mL). The ethereal layers were washed with brine (100 mL), dried over Na$_2$SO$_4$, filtered and concentrated to dryness. The residue was chromatographed (EA-Hept 4-1) to afford the title compound (1.1 g), contaminated with intermediate 5.v. (15 to 20%).

MS (ESI, m/z): 461.1 [M+H$^+$].

2.B.iii. trans-{4-[(1S)-1-amino-2-(6-methoxy-[1,5]naphthyridin-4-yl)-ethyl]-cyclohexyl}-carbamic acid benzyl ester To a solution of intermediate 2.B.ii (1.1 g, 2.39 mmol) in THF (20 mL) and water (2 mL) was added PPh$_3$ (1.1 g, 1.8 eq.). The mixture was heated at 60° C. for 2 h. Water (20 mL) was added. The reaction mixture was then stirred 15 min., cooled to rt and the volatiles were removed in vacuo. The residue was extracted with EA-MeOH (9-1, 200 mL). The org. layer was concentrated to dryness and the residue was chromatographed (DCM-MeOH 93-7 0 containing 7% aq. NH$_4$OH) to afford the title compound as a white solid (0.62 g, 59% yield).

$^1$H NMR (CDCl$_3$) δ: 8.67 (d, J=4.5 Hz, 1H); 8.19 (d, J=9.0 Hz, 1H); 7.39 (d, J=4.5 Hz, 1H); 7.37-7.30 (m, 5H); 7.11 (d, J=9.0 Hz, 1H); 5.09 (br s, 2H); 4.59 (m, 1H); 4.05 (s, 3H); 3.59-3.51 (m, 2H); 3.13 (m, 1H); 2.80 (dd, J=9.6, 12.3 Hz, 1H); 2.12 (br d, J=12.9 Hz, 2H); 2.04-1.93 (m, 2H); 1.47-1.13 (m, 7H).

2.B.iv. (1S)-(trans-2-(6-methoxy-[1,5]naphthyridin-4-yl)-1-{4-[(3-oxo-3,4-dihydro-2H-pyrido[3,2-b][1,4]thiazin-6-ylmethyl)-amino]-cyclohexyl}-ethyl)-carbamic acid tert-butyl ester Starting from intermediate 2.B.iii (0.62 g, 1.42 mmol), the title compound was obtained as a white solid (0.46 g, 0.8 mmol) using the procedures of Example 1, steps 1.xii and 1.xiii. The enantiomeric excess in favour of the title compound was 67%. The major enantiomer (0.120 g) was obtained pure using the procedure of Example 1, step 1.xiv.
MS (ESI, m/z): 579.3 [M+H$^+$].

2.B.v. 6-(trans-{4-[(1S)-1-amino-2-(6-methoxy-[1,5]naphthyridin-4-yl)-ethyl]-cyclohexylamino}-methyl)-4H-pyrido[3,2-b][1,4]thiazin-3-one Starting from intermediate 6.iv (0.120 g), in all respects identical to intermediate 1.xiv.b, the title enantiomer (0.098 g) was obtained as an off-white solid using the procedure described in Example 1, step 1.xv. The compound was triturated in ether.
MS (ESI, m/z): 479.2 [M+H$^+$].

Example 3

6-(trans-{4-[(1R*,2R*)-1-amino-2-hydroxy-2-(6-methoxy-[1,5]naphthyridin-4-yl)-ethyl]-cyclohexylamino}-methyl)-4H-pyrido[3,2-b][1,4]thiazin-3-one 3.i. trans-2-(4-tert-butoxycarbonylamino-cyclohexyl)-3-hydroxy-3-(6-methoxy-[1,5]naphthyridin-4-yl)-propionic acid methyl ester To a solution of trans-(4-tert-butoxycarbonylaminocyclohexyl)-acetic acid methyl ester (1.80 g, 6.63 mmol; prepared according to WO 2000/024717) in THF (20 mL) cooled to −78° C. was added LiHMDS (1M in THF, 17.1 mL) dropwise over 10 minutes. The resulting solution was stirred for 1.5 h in a dry-ice bath letting the temperature settle at −40° C. The reaction was cooled again to −78° C. and 6-methoxy-[1,5]naphthyridine-4-carbaldehyde (3.35 g, 17.82 mmol; prepared according to WO 2006/032466) was added quickly as a solid (2 mL THF were also added for rinse) and stirring was continued for 1.75 h at −78° C. Aq. NH$_4$Cl (50 mL) and EA (50 mL) were added. The two layers were separated and the aq. layer was extracted once with EA (50 mL). The combined org. layers were washed with brine (60 mL), dried over Na$_2$SO$_4$, filtered and concentrated to dryness. The residue was chromatographed (Hept-EA 1-1 to 1-4) to give the title compound as a pale yellow solid (2.68 g, 88% yield). The compound was obtained as a 1-1 mixture of (syn,anti)-isomers, contaminated by 10% of the starting aldehyde.
MS (ESI, m/z): 460.2 [M+H$^+$].

3.ii. trans-2-(4-tert-butoxycarbonylamino-cyclohexyl)-3-hydroxy-3-(6-methoxy-[1,5]naphthyridin-4-yl)-propionic acid To a solution of intermediate 3.i (3 g, 6.53 mmol) in MeOH/THF/water 2/2/1 (35 mL) was added LiOH.H$_2$O (0.587 g, 7.83 mmol) at rt. The resulting solution was stirred at 50° C. until completion. The reaction solution was concentrated in vacuo and the residue was partitioned between water (35 mL) and DCM-MeOH 9-1 (40 mL). The pH of the aq. layer was adjusted to 6-7 adding 1M HCl. The phases were separated and the aq. layer was extracted six times with DCM-MeOH 9-1 (6×40 mL). The combined org. layers were dried over Na$_2$SO$_4$, filtered and evaporated under reduced pressure. The solid residue was triturated in ether and filtered. After washing with ether (150 mL) and drying under HV the title compound was obtained as a white solid (1.57 g). The compound was obtained as a 1-1 mixture of (syn, anti)-isomers
MS (ESI, m/z): 446.1 [M+H$^+$].

3.iii. trans-{4-[(4R*,5R*)-5-(6-methoxy-[1,5]naphthyridin-4-yl)-2-oxo-oxazolidin-4-yl]-cyclohexyl}-carbamic acid tert-butyl ester To a solution of intermediate 3.ii (1.57 g, 3.52 mmol) in MeCN (20 mL) were added TEA (0.540 mL, 3.87 mmol) and DPPA (0.854 mL, 3.87 mmol) at rt. The suspension was heated to 85° C. for 45 min. Saturated NaHCO$_3$ (25 mL) and EA (25 mL) were added. The two layers were separated and the aq. layer was extracted twice with EA (2×25 mL). The combined org. layers were washed with brine (30 mL), dried over MgSO$_4$, filtered and concentrated to dryness. The residue was chromatographed on SiO$_2$ (EA-Hept 3-1 to 1-0) to give first the title (4R*,5R*)-isomer (0.495 g, Rf=0.20 in EA-Hept 3-1) as an off-white solid and then the (4S*,5R*)-isomer as an off-white solid (0.529 g, Rf=0.13 in EA-Hept 3-1).
$^1$H NMR (d6-DMSO) δ: 8.83 (d, J=4.4 Hz, 1H); 8.32 (d, J=9.1 Hz, 1H); 8.18 (s, 1H); 7.71 (dd, J=4.4 Hz, 1H); 7.31 (d, J=9.1 Hz, 1H); 6.36 (d, J=7.6 Hz, 1H); 6.36 (overlapped m, 1H); 4.32 (dd, J=7.6, 2.1 Hz, 1H); 3.98 (s, 3H); 2.91 (m 1H); 1.57-1.44 (m, 2H); 1.35-1.21 (m, 3H); 1.28 (s, 9H); 0.96 (m, 1H); 0.71-0.61 (m, 2H); 1.45 (m, 1H).
MS (ESI, m/z): 443.1 [M+H$^+$].

3.iv. trans-{4-[(1R*2R*)-1-amino-2-hydroxy-2-(6-methoxy-[1,5]naphthyridin-4-yl)-ethyl]-cyclohexyl}-carbamic acid tert-butyl ester To a solution of intermediate 3.iii (0.632 g, 1.42 mmol) in dioxane (14 mL) and water (9 mL) was added barium hydroxide octahydrate (0.706 g, 2.24 mmol). The resulting mixture was heated to reflux overnight. The solvent was evaporated under reduced pressure and the aq. residue was taken up in a DCM-MeOH mixture (9-1; 30 mL). The two layers were separated and the aq. layer was extracted three times (3×30 mL). The combined org. layers were dried over MgSO$_4$, filtered and evaporated under reduced pressure. After drying under HV, the title amino alcohol was obtained as a yellowish solid. The solid was triturated in Hept, filtered and dried under high vacuo to give the title amino acid (0.466 g, 78% yield) as a beige solid.
MS (ESI, m/z): 417.4 [M+H$^+$].

3.v. trans-{4-[(1R*,2R*)-1-(9H-fluoren-9-yl-methoxycarbonylamino)-2-hydroxy-2-(6-methoxy-[1,5]naphthyridin-4-yl)-ethyl]-cyclohexyl}-carbamic acid tert-butyl ester To a solution of intermediate 3.iv (0.460 g, 1.12 mmol) in acetone (6 mL), THF (6 mL) and water (6 mL) were added NaHCO$_3$ (0.444 g, 5.28 mmol) and then Fmoc-Cl (98%, 0.396 g, 1.50 mmol) at rt under vigorous stirring. The reaction proceeded for 5 h. The volatiles were removed under reduced pressure and the residue was filtered. The yellow solid was washed with water and dried under HV to give the title compound as a yellowish foam (0.787 g, 80% purity).
MS (ESI, m/z): 639.3 [M+H$^+$].

3.vi. [(1R*,2R*)-1-trans-(4-amino-cyclohexyl)-2-hydroxy-2-(6-methoxy-[1,5]naphthyridin-4-yl)-ethyl]-carbamic acid 9H-fluoren-9-ylmethyl ester A solution of intermediate 3.v (0.788 g, 0.98 mmol) in TFA (4.5 mL) was stirred at rt for 15 min. The solvent was removed in vacuo and the residue was partitioned between saturated NaHCO$_3$ (10 mL) and DCM-MeOH (9-1, 10 mL). The pH was adjusted to 13 by addition of 1M NaOH. The aq. layer was extracted five times with DCM-MeOH (9-1; 5×10 mL). The combined org. layers were dried over MgSO$_4$, filtered and evaporated under reduced pressure to give the title compound as a yellow gum (0.635 g, 75% purity).
MS (ESI, m/z): 539.2 [M+H$^+$].

3.vii. ((1R*,2R*)-2-hydroxy-2-(6-methoxy-[1,5]naphthyridin-4-yl)-1-trans-{4-[(3-oxo-3,4-dihydro-2H-pyrido[3,2-b][1,4]thiazin-6-ylmethyl)-amino]-cyclohexyl}-ethyl)-carbamic acid 9H-fluoren-9-ylmethyl ester Starting from intermediate 3.vi (0.635 g, 0.884 mmol), the title compound was obtained as a yellowish foam (0.277 g, 44% yield) using the procedure of Example 1, step 1.xiii. The compound was purified by chromatography (DCM-MeOH 93-7 containing 0.7% aq. NH$_4$OH).
MS (ESI, m/z): 717.1 [M+H$^+$].

3.viii. 6-(trans-{4-[(1R*2R*)-1-amino-2-hydroxy-2-(6-methoxy-[1,5]naphthyridin-4-yl)-ethyl]-cyclohexylamino}-methyl)-4H-pyrido[3,2-b][1,4]thiazin-3-one To a solution of intermediate 3.vii (0.277 g, 0.39 mmol) in DMF (8.6 mL) was added piperidine (99% yield, 0.462 mL, 4.63 mmol). The resulting mixture was stirred at rt for 45 min. LCMS showed complete reaction. The solvent was removed in vacuo and the residue was purified by column chromatography (DCM-MeOH 9-1 containing 1% NH$_4$OH then 6-1 containing 1% NH$_4$OH) to give the title compound as an off-white foam (0.129 g, 68% yield). The compound was obtained as a 3.5-1 mixture of syn-anti isomers.
MS (ESI, m/z): 495.3 [M+H$^+$].

Example 4 trans-{4-[(1RS)-1-amino-2-(6-methoxy-[1,5]naphthyridin-4-yl)-ethyl]-cyclohexyl}-[3-(2,5-difluoro-phenyl)-allyl]-amine

4.i. [1-trans-{(RS)-4-[3-(2,5-difluoro-phenyl)-allylamino]-cyclohexyl}-2-(6-methoxy-[1,5]naphthyridin-4-yl)-ethyl]-carbamic acid tert-butyl ester Starting from intermediate 1.xii (0.1 g, 0.25 mmol) and 3-(2,5-difluoro-phenyl)-propenal (see preparation A, 0.046 g, 1.1 eq.), the title compound was obtained as a white solid (0.103 g, 74% yield) using the procedure of Example 1, step 1.xiii. The compound was purified by chromatography (DCM-MeOH 93-7 0 containing 7% aq. NH$_4$OH).
MS (ESI, m/z): 493.2 [M+H$^+$].

4.ii. trans-{4-[(RS)-1-amino-2-(6-methoxy-[1,5]naphthyridin-4-yl)-ethyl]-cyclohexyl}-[3-(2,5-difluoro-phenyl)-allyl]-amine Starting from intermediate 4.i (0.1 g, 0.18 mmol), the title compound was obtained as a white solid (0.035 g, 42% yield) using the procedure of Example 1, step 1.xv. The compound was purified by trituration in ether.
MS (ESI, m/z): 493.2 [M+H$^+$].

Example 5

8-[(2RS)-2-amino-2-trans-{4-[(E)-3-(2,5-difluoro-phenyl)-allylamino]-cyclohexyl}-ethyl]-2-methoxy-quinoline-5-carboxylic acid methyl ester

5.i. 8-benzyloxy-5-bromo-2-methoxy-quinoline

To an ice-chilled solution of 8-benzyloxy-2-methoxy-quinoline (prepared as described in WO 2004/02992, 71.09 g, 268 mmol) in DCM (1.6 L) was added NBS (53.0 g, 1.11 eq.). The mixture was stirred for 5 h allowing the temperature to gradually reach rt. The solution was washed with saturated NaHCO$_3$ (6×500 mL), brine (4×500 mL), dried over Na$_2$SO$_4$, filtered and concentrated to dryness. The residue was dried under HV to give the title bromide as a light brown solid (89.37 g, 97% yield).
$^1$H NMR (CDCl$_3$) δ: 8.34 (d, J=9.0 Hz, 1H); 7.57-7.53 (m, 2H); 7.50 (d, J=8.2 Hz, 1H); 7.42-7.29 (m, 3H); 7.02 (d, J=9.0 Hz, 1H); 6.98 (d, J=8.2 Hz, 1H); 5.34 (s, 2H); 4.13 (s, 3H).

5.ii. 8-benzyloxy-2-methoxy-5-(E)-styryl-quinoline

To a solution of the intermediate 5.i. (59.76 g, 173.6 mmol), trans-2-phenylvinyl boronic acid (25.69 g, 1 eq.) in dioxane (320 mL) and water (80 mL) were added K$_2$CO$_3$ (31.2 g, 225.7 mmol) and Pd[P(Ph)$_3$]$_4$ (5 g, 2.5 mol %). The resulting mixture was heated to 100° C. overnight. After cooling to rt, EA (800 mL), water (500 mL) and 10% NaHSO$_4$ (300 mL) were added. The two layers were decanted and the aq. layer was extracted twice with DCM (2×300 mL). The combined org. layers were dried over Na$_2$SO$_4$, filtered and concentrated to dryness. The residue was triturated in ether, filtered and dried under HV to afford the title compound as a white solid (62 g, 97% yield).
$^1$H NMR (CDCl$_3$) δ: 8.39 (d, J=9.0 Hz, 1H); 7.66 (d, J=16.1 Hz, 1H); 7.60-7.53 (m, 5H); 7.43-7.27 (m, 6H); 7.14 (d, J=8.2 Hz, 1H); 7.05 (d, J=16.1 Hz, 1H); 6.99 (d, J=9.0 Hz, 1H); 5.39 (s, 2H); 4.14 (s, 3H).

5.iii. 8-benzyloxy-2-methoxy-quinoline-5-carbaldehyde

To a solution of intermediate 5.ii (24.1 g, 65.6 mmol) in DCM (300 mL) and water (50 mL) were added NMO (15.84 g, 2 eq.) and potassium osmate dihydrate (0.725 g, 3 mol %). The resulting mixture was stirred at rt overnight. After treatment with 10% NaHSO$_3$ (2×250 mL) and 10% NaHSO$_4$ (250 mL), the organic layer was dried over MgSO$_4$, filtered and concentrated to dryness to afford the title diol as a brown foam (25.7 g). The latter was taken up in acetone (400 mL), warmed with a water bath at a temperature in the vicinity of 40° C., and treated with a solution of sodium periodate (34.23 g, 160.0 mmol) in water (50 mL). The mixture was stirred at the same temperature for 30 min. Water (700 mL) was added and the volatiles were removed in vacuo. The aq. layer was extracted with DCM (500 mL). The org. layer was dried over MgSO$_4$, filtered and concentrated to dryness. The resulting residue was poured into water, filtered, rinsed several times with water and dried under HV to afford the title aldehyde as a dark solid (18.93 g, 64.5 mmol).

¹H NMR (CDCl₃) δ: 10.1 (s, 1H); 9.48 (d, J=9.1 Hz, 1H); 7.75 (d, J=8.2 Hz, 1H); 7.60-7.55 (m, 2H); 7.44-7.31 (m, 3H); 7.16 (d, J=8.2 Hz, 1H); 7.11 (d, J=9.1 Hz, 1H); 5.42 (s, 2H); 4.12 (s, 3H).

5.iv. 8-benzyloxy-2-methoxy-quinoline-5-carboxylic acid

To a solution of intermediate 5.iii (20 g, 68.2 mmol) in 2-methyl-2-propanol (500 mL) and DCM (100 mL) were added 2-methyl-2-butene (200 mL) and a solution of sodium chlorite (77 g, 10 eq., 80% purity) and sodium dihydrogen phosphate (75.27 g, 8 eq.) in water (300 mL). The reaction was stirred overnight at rt. The reaction mixture was diluted with water (200 mL) and EA (200 mL). The two layers were decanted and the aq. layer was extracted once with EA (200 mL). The combined org. layers were washed with brine, dried over Na₂SO₄, filtered and concentrated to dryness to afford the title acid as a white solid (16.0 g, 75% yield).
¹H NMR (CDCl₃) δ: 9.37 (d, J=9.4 Hz, 1H); 8.27 (d, J=8.50 Hz, 1H); 7.60-7.56 (m 2H); 7.44-7.30 (m, 3H); 7.10 (d, J=8.5 Hz, 1H); 7.08 (d, J=9.4 Hz, 1H); 5.42 (s, 2H); 4.14 (s, 3H).

5.v. 8-benzyloxy-2-methoxy-quinoline-5-carboxylic acid methyl ester

To a solution of intermediate 5.iv (15.8 g, 51.1 mmol) in benzene (450 mL) and MeOH (80 mL) was added a solution of TMSCHN₂ (2M in ether, 30 mL, 60 mmol) dropwise. The reaction was stirred 45 min at rt and AcOH (enough to destroy the excess of reagent) was added. The reaction mixture was diluted with saturated NaHCO₃ (300 mL). The aq. layer was separated and extracted twice with EA (2×200 mL). The combined org. layers were washed with brine (200 mL), dried over Na₂SO₄, filtered and concentrated to dryness to give the title compound as a white solid (15.8 g, 95% yield).
¹H NMR (d6-DMSO) δ: 9.15 (d, J=9.4 Hz, 1H); 8.06 (d, J=8.5 Hz, 1H); 7.59-7.53 (m, 2H); 7.44-7.36 (m, 2H); 7.35-7.29 (m, 2H); 7.18 (d, J=9.4 Hz, 1H); 5.40 (s, 2H); 4.01 (s, 3H); 3.87 (s, 3H).
MS (ESI, m/z): 324.2 [M+H⁺].

5.vi. 8-hydroxy-2-methoxy-quinoline-5-carboxylic acid methyl ester

To a solution of intermediate 5.v (15.8 g, 48.9 mmol) in EA (380 mL) was added 10% Pd/C (3.03 g). The reaction was stirred under hydrogen atmosphere for 2 h. The catalyst was removed by filtration and the filtrate evaporated under reduced pressure. After drying under HV, the title compound was obtained as a white solid (10.84 g, 95% yield).
¹H NMR (d6-DMSO) δ: 9.96 (br s, 1H); 9.18 (d, J=9.4 Hz, 1H); 8.03 (d, J=8.5 Hz, 1H); 7.16 (d, J=9.4 Hz, 1H); 7.10 (d, J=8.5 Hz, 1H); 4.06 (s, 3H); 3.85 (s, 3H).
MS (ESI, m/z): 234.3 [M+H⁺].

5.vii. 2-methoxy-8-trifluoromethanesulfonyloxy-quinoline-5-carboxylic acid methyl ester To a solution of intermediate 5.vi (10.84 g, 46.5 mmol) in DMF (110 mL) were added TEA (7.76 mL, 55.8 mmol) and N-phenyl-bis(trifluoromethanesulfonimide (18.27 g, 51.1 mmol). The reaction mixture was heated at 40° C. overnight. After cooling, the solvent was removed in vacuo and the residue was partitioned between saturated NaHCO₃ (100 mL) and DCM (150 mL). The organic layer was dried over Na₂SO₄, filtered and concentrated to dryness. The residue was filtered through silica (DCM) to afford the triflate (21.89 g) as an off-white solid, contaminated with a by-product.
MS (ESI, m/z): 366.1 [M+H⁺].

5.viii. 2-methoxy-8-(E)-styryl-quinoline-5-carboxylic acid methyl ester

Starting from intermediate 5.vii (theoretically 46.5 mmol) and using the procedure of step 5.ii, the title (E)-alkene was obtained as a yellowish solid (15.4 g). The crude material was purified by chromatography over SiO₂ using Hept-EA 4-1 as eluent.
MS (ESI, m/z): 320.3 [M+H⁺].

5.ix. 8-(1,2-dihydroxy-2-phenyl-ethyl)-2-methoxy-quinoline-5-carboxylic acid methyl ester Starting from intermediate 5.viii (15.4 g, 86% purity), the title diol was obtained as a yellowish solid (10.3 g, 70% yield) using the procedure of Example 1, step 1.vi, with the exception that the reaction was performed at 80° C. The crude material was purified by column chromatography (EA-Hept 2-1).
¹H NMR (CDCl₃) δ: 9.30 (d, J=9.4 Hz, 1H); 7.83 (d, J=7.5 Hz, 1H); 7.20-7.18 (m, 3H); 7.09 (d, J=9.4 Hz, 1H); 7.04-7.01 (m, 2H); 6.89 (d, J=7.5 Hz, 1H); 6.61 (d, J=9.3 Hz, 1H); 5.11 (d, J=7.5 Hz, 1H); 5.02 (m, 1H); 4.74 (br s), 4.03 (s, 3H); 3.97 (s, 3H).

5.x. 8-formyl-2-methoxy-quinoline-5-carboxylic acid methyl ester

To a solution of intermediate 5.ix (10.3 g, 29.1 mmol) in acetone (170 mL), warmed to 45° C. was added a solution of sodium periodate (15 g, 2.5 eq.) in water (60 mL). The mixture was stirred at the same temperature for 40 min. The volatiles were removed in vacuo and the residue was taken up in water (300 mL), filtered and the solids were washed with water, dried under HV to afford the title aldehyde (7.0 g, 97% yield) as a yellow solid.
¹H NMR (CDCl₃) δ: 11.41 (s, 1H); 9.16 (d, J=9.4 Hz, 1H); 8.23 (d, J=7.5 Hz, 1H); 8.13 (d, J=7.5 Hz, 1H); 7.11 (d, J=9.4 Hz, 1H); 4.14 (s, 3H); 4.04 (s, 3H).

5.xi. (E)-8-[2-trans-(tert-butoxycarbonylamino-cyclohexyl)-vinyl]-2-methoxy-quinoline-5-carboxylic acid methyl ester Starting from intermediate 1.iv (11.17 g, 26.5 mmol) and intermediate 5.x (6.5 g, 1 eq.), the title (E)-alkene was obtained as a white solid (3.56 g, 30% yield) using the procedure of Example 1, step 1.v. The crude material was purified by chromatography over SiO₂ (DCM).
¹H NMR (CDCl₃) δ: 9.22 (d, J=9.5 Hz, 1H); 8.06 (d, J=7.8 Hz, 1H); 7.80 (d, J=7.8 Hz, 1H); 7.61 (d, J=16.5 Hz, 1H); 7.03 (d, J=9.5 Hz, 1H); 6.51 (dd, J=6.9, 16.5 Hz, 1H); 4.41 (m, 1H); 4.12 (s, 3H); 3.98 (s, 3H); 3.48 (m, 1H); 2.26 (m, 1H); 2.14-2.11 (m, 2H); 2.01-1.97 (m, 2H); 1.48 (s, 9H); 1.48-1.35 (m, 2H); 1.30-1.17 (m, 2H).
MS (ESI, m/z): 441.3 [M+H⁺].

5.xii. 8-[rac-2-trans-(4-amino-cyclohexyl)-2-tert-butoxycarbonylamino-ethyl]-2-methoxy-quinoline-5-carboxylic acid methyl ester Starting from intermediate 5.xi (3.56 g, 8.1 mmol), the compound (0.47 g, 1.02 mmol) was prepared as a grey solid, following the sequence described in Example 1, step 1.vi (asymmetric dihydroxylation using AD-mix β, 98% yield), step 1.vii (carbonate formation, quant.), step 1.viii (hydrogenolysis at 50° C. for 1 day, 54% yield), step 1.ix (Boc deprotection, Cbz introduction, 70% yield), step 1.x (alcohol oxidation, 80% yield), step 1.xi (reductive amination at 50° C. for 6 h, 80% yield), step 1.xii (Boc formation and Cbz hydrogenolysis, 55% yield). If necessary, the crude intermediates were purified by chromatography using the appropriate solvent mixture.

$^1$H NMR (d6-DMSO) main rotamer δ: 9.03 (d, J=9.6 Hz, 1H); 7.92 (d, J=7.5 Hz, 1H); 7.57 (d, J=7.5 Hz, 1H); 7.14 (d, J=9.6 Hz, 1H); 6.56 (d, J=9.6 Hz, 1H); 4.00 (s, 3H); 3.88 (s, 3H); 3.71-3.59 (m, 3H); 2.76 (app t, J=12.0 Hz, 1H); 1.98 (br s, 1H); 1.78-1.73 (m, 5H); 1.35 (m, 1H); 1.12 (s, 9H); 1.12-0.98 (m, 4H).

MS (ESI, m/z): 458.3 [M+H$^+$].

5.xiii. 8-((2RS)-2-tert-butoxycarbonylamino-2-trans-{4-[3-(E)-(2,5-difluoro-phenyl)-allylamino]-cyclohexyl}-ethyl)-2-methoxy-quinoline-5-carboxylic acid methyl ester Starting from intermediate 7.xii (0.47 g, 1 mmol) and 3-(2,5-difluoro-phenyl)-propenal (0.190 g, 1.1 eq.), the title compound (0.402 g, 64% yield) was prepared as a white solid using the procedure described in Example 1, step 1.xiii. The compound was purified by chromatography (DCM-MeOH 19-1 0.5% aq. NH$_4$OH)

MS (ESI, m/z): 610.2 [M+H$^+$].

5.xiv. 8-[(2RS)-2-amino-2-trans-{4-[(E)-3-(2,5-difluoro-phenyl)-allylamino]-cyclohexyl}-ethyl]-2-methoxy-quinoline-5-carboxylic acid methyl ester Starting from intermediate 5.xiii (0.042 g, 0.07 mmol), the title compound was obtained as a white solid (0.027 g, 77% yield) using the procedure of Example 1, step 1.xv. The compound was purified by chromatography (DCM-MeOH 93-7 containing 0.7% aq. NH$_4$OH).

$^1$H NMR (d6-DMSO) δ: 9.07 (d, J=9.4 Hz, 1H); 7.98 (d, J=7.5 Hz, 1H); 7.63 (d, J=7.5 Hz, 1H); 7.45 (m, 1H); 7.22 (td, J=4.8, 9.3 Hz, 1H); 7.15 (d, J=9.3 Hz, 1H); 7.09 (m, 1H); 6.60 (d, J=15.9 Hz, 1H); 6.50 (td, J=4.8, 15.9 Hz, 1H); 4.00 (s, 3H); 3.91 (s, 3H); 3.53 (dd, J=3.9, 12.3 Hz, 1H); 3.37 (d, J=4.8 Hz, 2H); 2.93 (m, 1H); 2.74 (dd, J=9.3, 12.3 Hz, 1H); 2.34 (m, 1H); 1.99-1.87 (m, 4H); 1.75 (m, 1H); 1.50-1.10 (m, 5H); 0.98-0.92 (m, 2H).

MS (ESI, m/z): 510.3 [M+H$^+$].

Example 6

[8-((2RS)-2-amino-2-trans-{4-[3-(E)-(2,5-difluoro-phenyl)-allylamino]-cyclohexyl}-ethyl)-2-methoxy-quinolin-5-yl]-methanol 6.i. 8-[(2RS)-2-tert-butoxycarbonylamino-2-trans-(4-{tert-butoxycarbonyl-[3-(E)-(2,5-difluoro-phenyl)-allyl]-amino-cyclohexyl}-ethyl]-2-methoxy-quinoline-5-carboxylic acid methyl ester To a solution of intermediate 5.xiii (0.362 g, 0.59 mmol) in DCM (3.5 mL), were added TEA (0.165 mL, 1.19 mmol) and Boc$_2$O (0.144 g, 0.65 mmol). The reaction proceeded overnight. Sat. NaHCO$_3$ (10 mL) was added and the phases were separated. The aq. layer was extracted once with DCM-MeOH (9-1, 20 mL). The combined org. layers were washed with brine (20 mL), dried over MgSO$_4$, filtered and evaporated under reduced pressure. The residue was dried under HV and used without further purification. The title compound was obtained as an off-white solid (0.461 g, quant.).

MS (ESI, m/z): 710.5 [M+H$^+$].

6.ii. {4-[1-tert-butoxycarbonylamino-2-(5-hydroxymethyl-2-methoxy-quinolin-8-yl)-ethyl]-cyclohexyl}-[3-(E)-(2,5-difluoro-phenyl)-allyl]-carbamic acid tert-butyl ester To an ice-chilled solution of intermediate 6.i (theoretically 0.59 mmol) in ether (6.2 mL) was added DIBAH (1M in hexanes, 1.85 mL, 1.85 mmol). After 2 h at this temperature, DIBAH (1.85 mL) was added and the reaction proceeded 30 min at rt. Water (0.4 mL) was added. The reaction was stirred 40 min. and the mixture was diluted with ether (15 mL), and the solids were filtered off. The filtrate was concentrated to dryness. The residue was purified by column chromatography (DCM-MeOH 19-1) to give the title alcohol as a white foam (0.278 g).

MS (ESI, m/z): 682.3 [M+H$^+$].

6.iii. [8-((2RS)-2-amino-2-trans-{4-[3-(E)-(2,5-difluoro-phenyl)-allylamino]-cyclohexyl}-ethyl)-2-methoxy-quinolin-5-yl]-methanol Starting from intermediate 6.ii (0.025 g, 0.037 mmol), the title compound was obtained as a yellowish foam (0.017 g, 98% yield) using the procedure of Example 1, step 1.xv.

$^1$H NMR (d6-DMSO) δ: 8.37 (d, J=9.0 Hz, 1H); 7.46-7.40 (m, 2H); 7.31 (d, J=7.2 Hz, 1H); 7.21 (td, J=4.8, 9.0 Hz, 1H); 7.07 (m, 1H); 6.99 (d, J=9.0 Hz, 1H); 6.59 (d, J=16.2 Hz, 1H); 6.48 (td, J=4.8, 16.2 Hz, 1H); 5.23 (m, 1H); 4.84 (br s, 2H); 3.96 (s, 3H); 3.44 (dd, J=4.2, 12.3 Hz, 1H); 3.35 (d, J=4.8 Hz, 2H); 2.90 (m, 1H); 2.64 (dd, J=9.0, 12.3 Hz, 1H); 2.33 (m, 1H); 2.00-1.90 (m, 4H); 1.73 (m, 1H); 1.48-1.08 (m, 5H); 0.99-0.89 (m, 2H).

MS (ESI, m/z): 482.4 [M+H$^+$].

Example 7

6-(trans-{4-[(1RS)-1-amino-2-(3-methoxy-quinoxalin-5-yl)-ethyl]-cyclohexylamino}-methyl)-4H-pyrido[3,2-b][1,4]thiazin-3-one 7.i. (3-methoxy-quinoxalin-5-yl)-methanol To a stirred suspension of 3-methoxy-quinoxaline-5-carbaldehyde (prepared as described in WO 2006/032466, 5.0 g, 26.57 mmol) in EtOH (200 mL) cooled at 0° C., NaBH$_4$ (1.1 g) was added in one portion. The reaction mixture was warmed to rt and THF (50 mL) was added. A clear solution was obtained. The mixture was further stirred at rt for 30 min. Water (200 mL) was added and the volatiles were removed in vacuo. The residue was filtered off, washed with water. The solid was dried under HV to afford the title alcohol as a brown solid (4.8 g, 95% yield).

$^1$H NMR (d6-DMSO) δ: 8.58 (s, 1H); 7.86 (d, J=8.4 Hz, 1H); 7.82 (dd, J=1.2, 7.5 Hz, 1H); 7.61 (dd, J=7.5, 8.4 Hz, 1H); 5.22 (t, J=5.7 Hz, 1H); 5.04 (d, J=5.7 Hz, 2H); 4.02 (s, 3H).

MS (ESI, m/z): 482.4 [M+H$^+$].

7.ii. 8-bromomethyl-2-methoxy-quinoxaline

To a stirred solution of intermediate 7.i (4.8 g, 25.23 mmol) in DMF (45 mL), phosphorous tribromide (2.6 mL, 1.1 eq.)

was added dropwise at rt. The reaction was stirred 30 min and saturated NaHCO$_3$ was added. The solids were filtered off, thoroughly washed with water and taken up in EA (200 mL). The org. layer was washed with brine, dried over Na$_2$SO$_4$, filtered through a pad of SiO$_2$ and the filtrate was concentrated to dryness to give the title compound (5.5 g, 86% yield) as a beige solid.

$^1$H NMR (CDCl$_3$) δ: 8.51 (s, 1H); 8.00 (dd, J=1.5, 8.2 Hz, 1H); 7.78 (dd, J=1.5, 7.3 Hz, 1H); 7.53 (dd, J=7.3, 8.2 Hz, 1H); 5.09 (s, 2H); 4.16 (s, 3H).

7.iii. (RS)-2-(1,4-dioxa-spiro[4.5]dec-8-yl)-3-(3-methoxy-quinoxalin-5-yl)-propionic acid ethyl ester To a solution of DIPA (4.4 mL) in THF (40 mL) cooled to −78° C. was added BuLi (2.3N, 13 mL). The mixture was stirred 5 min to this temperature before warming to 0° C. The mixture was stirred 15 min before cooling to −78° C. After 5 min, a solution of (1,4-dioxa-spiro[4.5]dec-8-yl)-acetic acid ethyl ester (prepared as described in Org. Lett. (2005), 7, 4185; 4.6 g, 20 mmol) in THF (10 mL) was added dropwise over 35 min, keeping the internal temperature below −74° C. The solution was stirred 90 min below this temperature. A solution of intermediate 7.ii (5.06 g, 20 mmol) and HMPT (5 mL) in THF (15 mL) was added keeping the internal temperature below −45° C. After cooling to −78° C., the mixture was allowed to gradually warm up to −20° C. over 45 min. 10% aq. NaHSO$_4$ (100 mL) was added. The two layers were separated and the aq. layer was extracted with EA (150 mL). The combined org. layers were washed with brine, dried over Na$_2$SO$_4$, filtered and concentrated to dryness. The residue was chromatographed (Hept-EA 2-1) to afford the title compound as a yellowish oil (1.0 g, 12% yield).

$^1$H NMR (CDCl$_3$) δ: 8.47 (s, 1H); 7.87 (dd, J=1.5, 8.1 Hz, 1H); 7.49 (dd, J=1.5, 7.2 Hz, 1H); 7.42 (dd, J=7.2, 8.1 Hz, 1H); 4.11 (s, 3H); 3.95 (s, 4H); 3.93-3.84 (m, 2H); 3.73 (dd, J=4.2, 12.6 Hz, 1H); 3.05 (dd, J=11.1, 12.6 Hz, 1H); 2.82 (ddd, J=4.2, 7.5, 11.1 Hz, 1H), 2.03 (m, 1H); 1.86-1.49 (m, 8H); 0.96 (t, J=7.2 Hz, 3H).

MS (ESI, m/z): 401.4 [M+H$^+$].

7.iv. (RS)-2-(1,4-aioxa-spiro[4.5]dec-8-yl)-3-(3-methoxy-quinoxalin-5-yl)-propionic acid To a solution of intermediate 7.iii (1.0 g, 2.5 mmol) in EtOH (10 mL) was added 2N NaOH (2 mL). The mixture was heated at 90° C. for 24 h. The mixture was cooled to rt, and the volatiles were removed in vacuo. The residue was diluted with water (20 mL) and twice with ether (2×20 mL). The pH of the aq. layer was adjusted to 4-5 adding 1M HCl. The aq. layer was extracted twice with EA (2×50 mL). The combined extracts were washed with brine, dried over Na$_2$SO$_4$, filtered and concentrated to dryness to give the title acid as a colourless foam (0.665 g, 71% yield).

$^1$H NMR (CDCl$_3$) δ: 8.47 (s, 1H); 7.88 (dd, J=1.5, 8.1 Hz, 1H); 7.51 (dd, J=1.5, 7.2 Hz, 1H); 7.42 (dd, J=7.2, 8.1 Hz, 1H); 4.08 (s, 3H); 3.95 (s, 4H); 3.72 (dd, J=3.9, 12.6 Hz, 1H); 3.09 (dd, J=10.5, 12.6 Hz, 1H); 2.90 (ddd, J=4.2, 6.9, 10.5 Hz, 1H); 2.02 (m, 1H); 1.85-1.73 (m, 4H); 1.64-1.50 (m, 4H).

MS (ESI, m/z): 373.2 [M+H$^+$].

7.v. (RS)-[1-(1,4-dioxa-spiro[4.5]dec-8-yl)-2-(3-methoxy-quinoxalin-5-yl)-ethyl]-carbamic acid tert-butyl ester To a solution of intermediate 7.iv (0.665 g, 1.78 mmol) in toluene (5 ml) and 2-methyl-2-propanol (3 ml) were added TEA (0.3 mL) and DPPA (0.43 mL). The mixture was stirred 5 min. at rt before heating to 90° C. After 2 h, cuprous chloride (0.03 g) was added. The reaction was let under heating further 2 h. The reaction mixture was cooled to rt, and sat. NaHCO$_3$ (20 mL) and EA (30 mL) were added. The two layers were separated and the aq. layer was extracted twice with EA (2×50 mL). The combined org. layers were washed with brine, dried over Na$_2$SO$_4$, filtered and concentrated to dryness. The residue was chromatographed (DCM-MeOH 19-1) to afford the N-Boc protected amine as a yellowish solid (0.56 g, 70% yield).

MS (ESI, m/z): 444.4 [M+H$^+$].

7.vi. (RS)-[2-(3-methoxy-quinoxalin-5-yl)-1-(4-oxo-cyclohexyl)-ethyl]-carbamic acid tert-butyl ester A solution of intermediate 7.v (0.56 g, 1.26 mmol) in AcOH (8 mL), THF (8 mL) and water (3 mL) was heated at 60° C. for 3 h. The solvents were removed in vacuo and the residue was partitioned between saturated NaHCO$_3$ (50 mL) and EA (50 mL). The aq. layer was extracted once with EA (50 mL). The combined org. layers were washed with brine, dried over Na$_2$SO$_4$, filtered and concentrated to dryness to afford the title ketone as a brown solid (0.5 g, 99% yield).

MS (ESI, m/z): 400.5 [M+H$^+$].

7.vii. (RS)-[(cis and trans)-1-(4-amino-cyclohexyl)-2-(3-methoxy-quinoxalin-5-yl)-ethyl]-carbamic acid tert-butyl ester Starting from intermediate 7.vi (0.5 g, 1.25 mmol), the title amine was obtained as an off-white solid using the procedure of Example 1, step 1.xi. The compound, purified by chromatography over SiO$_2$ (DCM-MeOH 6-1 containing 1% aq. NH$_4$OH), was recovered as a cis-trans mixture.

MS (ESI, m/z): 401.3 [M+H$^+$].

7.viii. a. (RS)-(2-(3-methoxy-quinoxalin-5-yl)-1-{trans-4-[(3-oxo-3,4-dihydro-2H-pyrido[3,2-b][1,4]thiazin-6-ylmethyl)-amino]-cyclohexyl}-ethyl)-carbamic acid tert-butyl ester and b. (RS)-(2-(3-methoxy-quinoxalin-5-yl)-1-{cis-4-[(3-oxo-3,4-dihydro-2H-pyrido[3,2-b][1,4]thiazin-6-ylmethyl)-amino]-cyclohexyl}-ethyl)-carbamic acid tert-butyl ester Starting from intermediate 7.vii, the title compound was obtained using the procedure of Example 1, step 1.xiii. The crude material was purified by chromatography over SiO$_2$ (DCM-MeOH 93-7 containing 0.7% aq. NH$_4$OH) to afford first the cis-isomer (0.070 g, 16% yield) and then the trans-isomer (white solid, 0.25 g, 60% yield).

Intermediate 7.viii.a (trans-isomer): MS (ESI, m/z): 579.3 [M+H$^+$].

Intermediate 7.viii.a (ciss-isomer): MS (ESI, m/z): 579.3 [M+H$^+$].

7.ix. 6-(trans-{4-[(1RS)-1-amino-2-(3-methoxy-quinoxalin-5-yl)-ethyl]-cyclohexylamino}-methyl)-4H-pyrido[3,2-b][1,4]thiazin-3-one Starting from intermediate 7.viii.a (0.051 g, 0.088 mmol), the title compound was obtained as an off-white solid (0.03 g, 71% yield) using the procedure of Example 1, step 1.xv.

MS (ESI, m/z): 479.3 [M+H$^+$].

Example 8

6-(cis-{4-[(1RS)-1-amino-2-(3-methoxy-quinoxalin-5-yl)-ethyl]-cyclohexylamino}-methyl)-4H-pyrido[3,2-b][1,4]thiazin-3-one Starting from intermediate 7.viii.b (0.065 g, 0.112 mmol), the title compound was obtained as an off-white solid (0.043 g, 80% yield) using the procedure of Example 1, step 1.xv.
MS (ESI, m/z): 479.3 [M+H$^+$].

Example 9

6-(trans-{4-[(1RS)-1-amino-2-(6-methoxy-[1,5]naphthyridin-4-yl)-ethyl]-cyclohexylamino}-methyl)-4H-pyrido[3,2-b][1,4]oxazin-3-one Starting from intermediate 1.xii (0.09 g, 0.225 mmol) and 3-oxo-3,4-dihydro-2H-pyrido[3,2-b][1,4]oxazine-6-carbaldehyde (0.044 g, 1.1 eq.), the title compound was obtained as an off-white solid (0.035 g) using the procedures of Example 1, steps 1.xiii (reductive amination, purification by chromatography using DCM-MeOH 93-7 containing 0.7% aq. NH$_4$OH) and 1.xv (deprotection). The compound was triturated in ether.
$^1$H NMR (DMSO) δ: 10.81 (s, 1H); 8.56 (s, 1H); 7.83 (d, J=8.4 Hz, 1H); 7.69 (d, J=7.8 Hz, 1H); 7.60-7.50 (m, 2H); 7.07 (d, J=8.4 Hz, 1H); 4.01 (s, 3H); 3.70 (s, 2H); 3.50 (s, 2H); 3.42 (m, 1H); 2.86 (m, 1H); 2.70 (m, 1H); 2.30 (m, 1H); 2.00-1.90 (m, 4H); 1.74 (m, 1H); 1.30-1.10 (m, 6H); 0.98 (m, 1H).
MS (ESI, m/z): 463.2 [M+H$^+$].

Example 10 trans-6-({4-[(1RS)-1-amino-2-(3-fluoro-6-methoxy-quinolin-4-yl)-ethyl]-cyclohexylamino}-methyl)-4H-pyrido[3,2-b][1,4]thiazin-3-one

10.i. (3-fluoro-6-methoxy-quinolin-4-yl)-methanol

To a solution of DIPA (14.7 mL, 104.3 mmol) in THF (410 mL), cooled to −70° C., was added n-BuLi (2.5N in hexanes, 42 mL). The reaction mixture was stirred 10 min at this temperature before warming to 0° C. The reaction mixture was stirred 15 min before cooling to −70° C. again. 3-fluoro-6-methoxy-quinoline (prepared as described in FR 2004/01105, 18.48 g, 104.3 mmol) in THF (85 mL+20 mL rinse) was added and the mixture was stirred 4 h at −78° C. DMF (12.9 mL, 166.9 mmol) was added dropwise. The turbid mixture became clear after 5 min. After 20 min, the reaction mixture was warmed up to rt. 10% NaHSO$_4$ (40 mL) was added. The solvent was removed in vacuo and the residue was diluted with water (200 mL). pH was adjusted to 7 with sat. NaHCO$_3$. The aq. layer was extracted twice with EA (2×200 mL). The combined org. layers were washed with brine (200 mL), dried over Na$_2$SO$_4$, filtered and concentrated to dryness. The residue was chromatographed (Hept-EA 1-1) to afford the title aldehyde (11.83 g) as a yellow oil. The latter was taken up in MeOH (140 mL) and NaBH$_4$ (0.808 g, 20.9 mmol) in one portion. After 30 min, the reaction mixture was warmed to rt. Water (140 mL) was added and the volatiles were removed in vacuo. The residue was filtered off and washed with water. The residue was extracted twice with EA (2×200 mL). The combined org. layers were washed with brine (200 mL), dried over MgSO$_4$, filtered and evaporated under reduced pressure. The residue was chromatographed (EA-Hept 1-1 to 4-1) to afford the starting material (3.47 g) and then the title alcohol (4.02 g, 19 mmol) as an off-white solid.
$^1$H NMR (DMSO) δ: 8.70 (s, 1H); 7.94 (d, J=9.1 Hz, 1H); 7.55 (d, J=2.6 Hz, 1H); 7.37 (dd, J=2.6, 9.1 Hz, 1H); 5.49 (t, J=6.0 Hz, 1H); 4.91 (d, J=6.0 Hz, 2H); 3.90 (s, 3H).
MS (ESI, m/z): 208.3 [M+H$^+$].

10.ii. 4-bromomethyl-3-fluoro-6-methoxy-quinoline

Starting from intermediate 10.i (3.94 g, 19 mmol), the title bromide was obtained (4.11 g, 80% yield) according to the procedure of Example 7, step 7.ii. The compound was purified by chromatography (Hept-EA 2-1).
$^1$H NMR (DMSO) δ: 8.76 (s, 1H); 7.99 (d, J=9.1 Hz, 1H); 7.50 (d, J=2.6 Hz, 1H); 7.37 (dd, J=2.6, 9.1 Hz, 1H); 5.14 (s, 2H); 3.96 (s, 3H).
MS (ESI, m/z): 272.1 [M+H$^+$].

10.iii. [(1RS)-1-cis/trans-(4-amino-cyclohexyl)-2-(3-fluoro-6-methoxy-quinolin-4-yl)-ethyl]-carbamic acid tert-butyl ester The title compound was obtained as a yellowish foam (0.274 g), starting from intermediate 10.ii (4.09 g, 15.1 mmol), and using the procedures of Example 7, steps 7.iii to 7.vii [ester alkylation (55% yield), saponification (74% yield), Curtius degradation (24% yield), ketal hydrolysis (quant.) and amine formation (42% yield)]. If necessary, the crude reaction mixtures were purified by chromatography over SiO$_2$ using an appropriate eluent. The amine was obtained as a cis-trans mixture.
MS (ESI, m/z): 418.2 [M+H$^+$].

10.iv. a. (1RS)-(2-(3-fluoro-6-methoxy-quinolin-4-yl)-1-trans-{4-[(3-oxo-3,4-dihydro-2H-pyrido[3,2-b][1,4]thiazin-6-ylmethyl)-amino]-cyclohexyl}-ethyl)-carbamic acid tert-butyl ester and b. (1RS)-(2-(3-fluoro-6-methoxy-quinolin-4-yl)-1-cis-{4-[(3-oxo-3,4-dihydro-2H-pyrido[3,2-b][1,4]thiazin-6-ylmethyl)-amino]-cyclohexyl}-ethyl)-carbamic acid tert-butyl ester The title trans-compound was obtained as an off-white solid (0.076 g, 57% yield), starting from intermediate 10.iii (0.1 g, 0.24 mmol), and using the procedure described in Example 7, step 7.viii. The trans-compound was purified by chromatography (DCM-MeOH 93-7 containing 0.7% aq. NH$_4$OH). The cis-isomer (white solid; 0.03 g; 27% yield) was also recovered during the chromatography (first eluting isomer).
Intermediate 10.iv.a (trans-isomer): MS (ESI, m/z): 596.2 [M+H$^+$].
Intermediate 10.iv.b (cis-isomer): MS (ESI, m/z): 596.2 [M+H$^+$].

10.v. trans-6-({4-[(1RS)-1-amino-2-(3-fluoro-6-methoxy-quinolin-4-yl)-ethyl]-cyclohexylamino}-methyl)-4H-pyrido[3,2-b][1,4]thiazin-3-one The title compound was obtained as an off-white foam (0.029 g, 45% yield), starting from intermediate 10.iv.a (0.077 g, 0.13 mmol) and using the procedure of Example 1, step 1.xv. The compound was purified by chromatography over SiO$_2$ (DCM-MeOH 9-1 containing 1% aq. NH$_4$OH).
$^1$H NMR (DMSO) δ: 10.81 (s, 1H); 8.64 (s, 1H); 7.92 (d, J=8.1 Hz, 1H); 7.70 (d, J=9.0 Hz, 1H); 7.36-7.32 (m, 2H);

7.07 (d, J=9.0 Hz, 1H), 3.91 (s, 3H); 3.71 (s, 2H); 3.50 (s, 2H); 3.13 (m, 1H); 2.90 (m, 1H); 2.80 (m, 1H); 2.31 (m, 1H); 2.00-1.85 (m, 4H); 1.71 (m, 1H); 1.29-1.10 (m, 6H); 1.02 (m, 1H).

MS (ESI, m/z): 496.5 [M+H$^+$].

Example 11 cis-6-({4-[(1RS)-1-amino-2-(3-fluoro-6-methoxy-quinolin-4-yl)-ethyl]-cyclohexylamino}-methyl)-4H-pyrido[3,2-b][1,4]thiazin-3-one The title compound was obtained as an off-white foam (0.022 g, 88% yield), starting from intermediate 10.iv.b (0.03 g, 0.05 mmol) and using the procedure of Example 1, step 1.xv.

MS (ESI, m/z): 496.5 [M+H$^+$].

Example 12 trans-{4-[(1RS)-1-amino-2-(3-fluoro-6-methoxy-quinolin-4-yl)-ethyl]-cyclohexyl}-[3-(E)-(2,5-difluoro-phenyl)-allyl]-amine 12.i. a. [(1RS)-1-trans-{4-[3-(E)-(2,5-difluoro-phenyl)-allylamino]-cyclohexyl}-2-(3-fluoro-6-methoxy-quinolin-4-yl)-ethyl]-carbamic acid tert-butyl ester and b. [(1RS)-1-cis-{4-[3-(E)-(2,5-difluoro-phenyl)-allylamino]-cyclohexyl}-2-(3-fluoro-6-methoxy-quinolin-4-yl)-ethyl]-carbamic acid tert-butyl ester The title trans-compound was obtained as an off-white solid (0.050 g, 49% yield), starting from intermediate 10.iii (0.0752 g, 0.18 mmol) and (E)-3-(2,5-difluoro-phenyl)-propenal (0.033 g, 1.1 eq.) and using the procedures of Example 7, step 7.viii. The compound was purified by chromatography (DCM-MeOH 19-1 containing 0.5% aq. NH$_4$OH). The cis-isomer (0.033 g, 32% yield, white solid) was also recovered during the chromatography (first eluting isomer).

Intermediate 12.i.a (trans-isomer): MS (ESI, m/z): 570.2 [M+H$^{3o}$].

Intermediate 12.i.b (cis-isomer): MS (ESI, m/z): 570.3 [M+H$^{3o}$].

12.ii. trans-{4-[(1RS)-1-amino-2-(3-fluoro-6-methoxy-quinolin-4-yl)-ethyl]-cyclohexyl}-[3-(E)-(2,5-difluoro-phenyl)-allyl]-amine Starting from intermediate 12.i.a (0.048 g, 0.086 mmol), the title compound was obtained as an off-white solid (0.034 g, 85% yield) using the procedure of Example 1, step 1.xv. The compound was purified by chromatography over SiO$_2$ (DCM-MeOH 9-1 containing 1% aq. NH$_4$OH).

MS (ESI, m/z): 470.4 [M+H$^+$].

Example 13 cis-{4-[(1RS)-1-amino-2-(3-fluoro-6-methoxy-quinolin-4-yl)-ethyl]-cyclohexyl}-[3-(E)-(2,5-difluoro-phenyl)-allyl]-amine Starting from intermediate 12.i.b (0.031 g, 0.055 mmol), the title compound was obtained as an off-white solid (0.019 g, 75% yield) using the procedure of Example 1, step 1.xv. The compound was purified by chromatography over SiO$_2$ (DCM-MeOH 19-1 containing 0.5% aq. NH$_4$OH).

MS (ESI, m/z): 470.3 [M+H$^+$].

Example 14 trans-6-({4-[(1RS)-1-amino-2-(3-fluoro-6-methoxy-[1,5]naphthyridin-4-yl)-ethyl]-cyclohexylamino}-methyl)-4H-pyrido[3,2-b][1,4]thiazin-3-one 14.i. 8-bromomethyl-7-fluoro-2-methoxy-[1,5]naphthyridine Starting from 3-fluoro-6-methoxy-[1,5]naphthyridine-4-carbaldehyde (prepared as described in WO 2006/032466, 4.2 g, 20.3 mmol), the title bromide (5.4 g, 19.9 mmol) was obtained as a beige solid using the procedures of Example 7, steps 7.i and 7.ii.

$^1$H NMR (d6-DMSO) δ: 8.87 (s, 1H); 8.32 (d, J=9.1 Hz, 1H); 7.29 (d, J=9.1 Hz, 1H); 5.09 (s, 2H); 4.07 (s, 3H).

14.ii. [(1RS)-1-cis/trans-(4-amino-cyclohexyl)-2-(3-fluoro-6-methoxy-[1,5]naphthyridin-4-yl)-ethyl]-carbamic acid tert-butyl ester The title compound was obtained as a white solid (1.6 g), starting from intermediate 14.i (5.4 g, 19.9 mmol), and using the procedures of Example 7, steps 7.iii to 7.vii [ester alkylation (63% yield), saponification (82% yield), Curtius degradation (83% yield), ketal hydrolysis (quant.) and amine formation (53% yield)]. If necessary, the crude reaction mixtures were purified by chromatography over SiO$_2$ using an appropriate eluent. The amine was obtained as a cis-trans mixture.

$^1$H NMR (CDCl$_3$) δ: 8.62 (s, 1H); 8.18 (d, J=9.0 Hz, 1H); 7.09 (d, J=9.0 Hz, 1H); 4.99 (m, 1H); 4.11 (s, 3×0.4H); 4.10 (s, 3×0.6H); 3.90 (m, 1H); 3.49-3.17 (m, 3H); 2.70 (m, 1H); 2.02-1.82 (m, 4H); 1.74-1.48 (m, 3H); 1.36-1.00 (m, 3H); 1.12 (s, 9×0.6H); 1.11 (s, 9×0.4H).

MS (ESI, m/z): 419.2 [M+H$^+$].

14.iii. a. (1RS)-(2-(3-fluoro-6-methoxy-[1,5]naphthyridin-4-yl)-1-trans-{4-[(3-oxo-3,4-dihydro-2H-pyrido[3,2-b][1,4]thiazin-6-ylmethyl)-amino]-cyclohexyl}-ethyl)-carbamic acid tert butyl ester and b. (1RS)-(2-(3-fluoro-6-methoxy-[1,5]naphthyridin-4-yl)-1-cis-{4-[(3-oxo-3,4dihydro-2H pyrido[3,2-b][1,4]thiazin-6-ylmethyl)-amino]-cyclohexyl}-ethyl)-carbamic acid tert butyl ester The title trans-compound was obtained as a white solid (0.32 g, 56% yield), starting from intermediate 14.ii (0.4 g, 0.95 mmol), and using the procedure of Example 7, step 7.viii. The trans-compound was purified by chromatography (DCM-MeOH 19-1 containing 0.5% aq. NH$_4$OH). The cis-isomer (glassy solid; 0.2 g; 35% yield) was also recovered during the chromatography (first eluting isomer).

Intermediate 14.iii.a (Trans-Isomer):

$^1$H NMR (d6-DMSO) δ (major rotamer): 10.81 (s, 1H); 8.69 (s, 1H); 8.22 (d, J=9.0 Hz, 1H); 7.69 (d, J=7.8 Hz, 1H); 7.20 (d, J=9.0 Hz, 1H); 7.07 (d, J=7.8 Hz, 1H); 6.48 (d, J=9.6 Hz, 1H); 4.03 (s, 3H); 3.71 (s, 2H); 3.70 (overlapped m, 1H); 3.50 (s, 2H); 3.36 (d, J=11.4 Hz, 1H); 3.00 (t, J=11.4 Hz, 1H); 2.31 (m, 1H); 2.00-1.80 (m, 4H); 1.39 (m, 1H); 2.17-0.89 (m, 5H); 1.07 (s, 9H).

MS (ESI, m/z): 597.1 [M+H$^+$].

Intermediate 14.iii.b (Cis-Isomer):

$^1$H NMR (d6-DMSO) δ (major rotamer): 10.81 (s, 1H); 8.69 (s, 1H); 8.23 (d, J=9.0 Hz, 1H); 7.70 (d, J=7.8 Hz, 1H);

7.20 (d, J=9.0 Hz, 1H); 7.08 (d, J=7.8 Hz, 1H); 6.46 (d, J=9.9 Hz, 1H); 4.04 (s, 3H); 3.80 (m, 1H); 3.67 (s, 2H); 3.50 (s, 2H); 3.42 (d, J=12.0 Hz, 1H); 2.97 (t, J=12.0 Hz, 1H); 2.64 (m, 1H); 1.75-1.35 (m, 9H); 1.06 (overlapped m, 1H); 1.05 (s, 9H).

MS (ESI, m/z): 597.4 [M+H$^+$].

14.iv. trans-6-({4-[(1RS)-1-amino-2-(3-fluoro-6-methoxy-[1,5]naphthyridin-4-yl)-ethyl]-cyclohexylamino}-methyl)-4H-pyrido[3,2-b][1,4]thiazin-3-one Starting from intermediate 14.iii.a (0.32 g, 0.53 mmol), the title compound was obtained as an off-white solid (0.23 g, 86% yield) using the procedure of Example 1, step 1.xv.

$^1$H NMR (d6-DMSO) δ: 10.81 (s, 1H); 8.73 (s, 1H); 8.25 (d, J=9.0 Hz, 1H); 7.70 (d, J=7.8 Hz, 1H); 7.20 (d, J=9.0 Hz, 1H); 7.07 (d, J=9.0 Hz, 1H); 4.00 (s, 3H); 3.70 (s, 2H); 3.50 (s, 2H); 3.20 (m, 1H); 2.98-2.89 (m, 2H); 2.30 (m, 1H); 2.00-1.80 (m, 3H); 1.77-1.72 (m, 2H); 1.31-0.98 (m, 7H).

MS (ESI, m/z): 497.3 [M+H$^+$].

Example 15 cis-6-({4-[(1RS)-1-amino-2-(3-fluoro-6-methoxy-[1,5]naphthyridin-4-yl)-ethyl]-cyclohexylamino}-methyl)-4H-pyrido[3,2-b][1,4]thiazin-3-one Starting from intermediate 14.iii.b (0.2 g, 0.33 mmol), the title compound was obtained as an off-white solid (0.12 g, 72% yield) using the procedure of Example 1, step 1.xv.

MS (ESI, m/z): 497.4 [M+H$^+$].

Example 16 trans-6-({4-[(1RS)-1-amino-2-(3-fluoro-6-methoxy-quinolin-4-yl)-ethyl]-cyclohexylamino}-methyl)-4H-benzo[1,4]oxazin-3-one 16.i. (trans-(2RS)-2-(3-fluoro-6-methoxy-quinolin-4-yl)-1-{4-[(3-oxo-3,4-dihydro-2H-benzo[1,4]oxazin-6-ylmethyl)-amino]-cyclohexyl}-ethyl)-carbamic acid tert-butyl ester The title trans-compound was obtained as an off-white solid (0.052 g, 47% yield), starting from intermediate 10.iii (0.079 g, 0.19 mmol) and 3-oxo-3,4-dihydro-2H-benzo[1,4]oxazine-6-carbaldehyde (0.037 g, 1.1 eq.) and using the procedure of Example 1, step 1.xiii. The compound was purified by chromatography (DCM-MeOH 93-7 containing 0.7% aq. NH$_4$OH). The cis-isomer (0.018 g, 16% yield, white solid) was also recovered during the chromatography (first eluting isomer).

MS (ESI, m/z): 579.3 [M+H$^+$].

16.ii. trans-6-({4-[(1RS)-1-amino-2-(3-fluoro-6-methoxy-quinolin-4-yl)-ethyl]-cyclohexylamino}-methyl)-4H-benzo[1,4]oxazin-3-one Starting from intermediate 16.i. (0.048 g, 0.084 mmol), the title compound was obtained as a yellowish solid (0.031 g, 78% yield) using the procedure of Example 1, step 1.xv. The compound was purified by chromatography over SiO$_2$ (DCM-MeOH 6-1 containing 1% aq. NH$_4$OH).

MS (ESI, m/z): 479.4 [M+H$^+$].

Example 17 trans-(1R*,2R*)-2-amino-2-{4-[(2,3-dihydro-benzo[1,4]dioxin-6-ylmethyl)-amino]-cyclohexyl}-1-(6-methoxy-[1,5]naphthyridin-4-yl)-ethanol 17.i. 2-(1,4-dioxa-spiro[4.5]dec-8-yl)-3-hydroxy-3-(6-methoxy-[1,5]naphthyridin-4-yl)-propionic acid ethyl ester To a solution of (1,4-dioxa-spiro[4.5]dec-8-yl)-acetic acid ethyl ester (3.6 g, 15.77 mmol) in THF (50 mL) cooled to −78° C. was added LiHMDS (1M in THF, 18.1 mL) under argon. The resulting solution was stirred for 1 h at −40° C., then recooled to −78° C. 6-methoxy-[1,5]naphthyridine-4-carbaldehyde (3.56 g, 18.92 mmol; prepared according to WO 2006/032466) was added portionwise and stirring was continued for 30 min at −78° C. The reaction mixture was quenched by the addition of aq. NH$_4$Cl. The two layers were separated and the aq. layer was extracted with EA. The combined org. layers were washed with brine, dried over Na$_2$SO$_4$, filtered and concentrated to dryness. The residue was chromatographed (Hept-EA 1-2→EA) to afford a diastereoisomeric 1:1 mixture of the title compound as a pale yellow oil (4.44 g, 68% yield).

MS (ESI, m/z): 417.5 [M+H$^+$].

17.ii. 2-(1,4-dioxa-spiro[4.5]dec-8-yl)-3-hydroxy-3-(6-methoxy-[1,5]naphthyridin-4-yl)-propionic acid To a solution of intermediate 17.i (5.2 g, 12.49 mmol) in 2:2:1 MeOH/THF/water (100 mL) was added LiOH monohydrate (3.14 g, 74.92 mmol) at rt. The resulting solution was stirred at 60° C. for 3 h. The resulting orange solution was concentrated. The residue was diluted with water and ether. The aq. layer was washed once more with ether and the pH of the aq. layer was adjusted to 4 by adding 3M HCl. The precipitate was filtered and washed with ether. The filtrate was extracted 4 times with DCM-MeOH (9:1) and the combined org. layers were concentrated. The residue was combined with the solid material obtained by filtration and concentrated to dryness to obtain a diastereoisomeric 1:1 mixture of the title compound as a colourless solid (4.46 g, 92% yield).

MS (ESI, m/z): 389.1 [M+H$^+$].

17.iii. 4-(1,4-dioxa-spiro[4.5]dec-8-yl)-5-(6-methoxy-[1,5]naphthyridin-4-yl)-oxazolidin-2-one To a suspension of intermediate 17.ii (4.46 g, 11.47 mmol) in MeCN (60 mL) were added TEA (1.8 mL, 12.62 mmol) and DPPA (3.0 mL, 12.62 mmol) at rt. The suspension was heated to 85° C. while the mixture became a clear solution. The reaction proceeded 30 min. After cooling to rt saturated NaHCO$_3$ and EA were added. The two layers were separated and the aq. layer was extracted twice with EA. The combined org. layers were washed with brine, dried over Na$_2$SO$_4$, filtered and concentrated to dryness. Thereby, a precipitate was formed that was filtered. The residue was concentrated to dryness. The residue was chromatographed (1000:25:2 DCM-MeOH—NH$_4$OH) to afford both diastereoisomers in their racemic form. The first compound to elute was the (4R,5S) and (4S,5R) isomers (1.48 g, colourless solid) followed by the (4R,5R) and (4S,5S) isomers (1.03 g, colourless solid).

MS (ESI, m/z): 386.3 [M+H$^+$].

17.iv. (4R*,5R*)-5-(6-methoxy-[1,5]naphthyridin-4-yl)-4-(4-oxo-cyclohexyl)-oxazolidin-2-one A solution of intermediate 17.iii ((4R,5R) and (4S,5S) isomers, 1.03 g, 2.67 mmol) in AcOH (20 mL), THF (10 mL) and water (10 mL) was heated to 70° C. for 4 h. The solvent was removed in vacuo and the residue was diluted with aq. NaHCO$_3$. The aq. layer was extracted with 9-1 DCM-MeOH. The combined org. extracts were dried over MgSO$_4$ and concentrated to afford the title intermediate as a yellow solid (0.92 g, 100% yield).

MS (ESI, m/z): 342.2 [M+H$^+$].

17.v. trans-(4R*,5R*)-4-(4-amino-cyclohexyl)-5-(6-methoxy-[1,5]naphthyridin-4-yl)-oxazolidin-2-one To a solution of intermediate 17.iv (0.92 g, 2.70 mmol) in MeOH (20 mL) and DCM (7 mL) were added ammonium acetate (5.19 g, 67.4 mmol) and sodium cyanoborohydride (339 mg, 5.39 mmol). The mixture was stirred at rt overnight. DCM (80 mL) and saturated NaHCO$_3$ (80 mL) were added. The two layers were separated and the aq. layer was extracted 12 times with DCM-MeOH (9:1). The combined org. layers were washed with brine, dried over Na$_2$SO$_4$, filtered and concentrated to dryness. The residue was chromatographed (1000:200:16 DCM-MeOH—NH$_4$OH) to afford the title intermediate as a pale yellow solid (0.47 g, 51% yield).

MS (ESI, m/z): 343.3 [M+H$^+$].

17.vi. trans-(4R*,5R*)-4-{4-[(2,3-dihydro-benzo[1,4]dioxin-6-ylmethyl)-amino]-cyclohexyl}-5-(6-methoxy-[1,5]naphthyridin-4-yl)-oxazolidin-2-one To a solution of intermediate 17.v (85 mg, 0.248 mmol) in MeOH (1 mL) and 1,2-DCE (4 mL) were added 3 Å molecular sieves (1 g) and 2,3-dihydro-benzo[1,4]dioxine-6-carbaldehyde (43 mg, 0.261 mmol). The mixture was stirred at 50° C. overnight. The reaction mixture was cooled to 0° C. and NaBH$_4$ (75 mg, 2.0 mmol) was added. The reaction proceeded for 30 min. DCM-MeOH (9:1) was added. The solids were filtered and washed with DCM-MeOH (9:1). Aq. NH$_4$OH was added and the phases were separated. The aq. layer was extracted with DCM-MeOH (9:1) and the combined org. layers were dried over Na$_2$SO$_4$ and concentrated. The residue was chromatographed (1000:50:4 DCM-MeOH—NH$_4$OH) to afford the title intermediate as a colourless solid (88 mg, 72% yield).

MS (ESI, m/z): 491.2 [M+H$^+$].

17.vii. trans-(1R*,2R*)-2-amino-2-{4-[2,3-dihydro-benzo[1,4]dioxin-6-ylmethyl)-amino]-cyclohexyl}-1-(6-methoxy-[1,5]naphthyridin-4-yl)-ethanol To a solution of intermediate 17.vi (75 mg, 0.153 mmol) in 1:1 water/dioxane (4 mL) was added KOH (69 mg, 1.22 mmol). The mixture was heated at 100° C. for 4 h. Water was added and the mixture was extracted with DCM-MeOH (9:1). The combined org. layers were dried over MgSO$_4$ and concentrated. The residue was chromatographed (1000:100:8 then 1000:200:16 DCM-MeOH—NH$_4$OH) to afford the title intermediate as a colourless solid (24 mg, 34% yield).

$^1$H NMR (CDCl$_3$) δ: 8.75 (d, J=4.4 Hz, 1H), 8.22 (dd, J=9.1, 0.6 Hz, 1H), 7.60 (d, J=4.4 Hz, 1H), 7.12 (d, J=9.1 Hz, 1H), 6.82 (m, 3H), 5.59 (d, J=3.2 Hz, 1H), 4.23 (s, 4H), 4.04 (s, 3H), 3.70 (s, 2H), 3.01 (dd, J=5.9, 3.2 Hz, 1H), 2.48 (m, 1H), 2.15-1.10 (m, 13H).

MS (ESI, m/z): 465.4 [M+H$^+$].

Example 18 trans-(1R*,2R*)-2-amino-2-{4-[(E)-3-(2,5-difluoro-phenyl)-allylamino]-cyclohexyl}-1-(6-methoxy-[1,5]naphthyridin-4-yl)-ethanol

18.i. trans-(4R*,5R*)-4-{4-[(E)-3-(2,5-difluoro-phenyl)-allylamino]-cyclohexyl}-5-(6-methoxy-[1,5]naphthyridin-4-yl)-oxazolidin-2-one To a solution of intermediate 17.v (40 mg, 0.117 mmol) in MeOH (0.3 mL) and 1,2-DCE (1 mL) were added 3 Å molecular sieves (10.5 g) and 3-(2,5-difluoro-phenyl)-propenal (21 mg, 0.123 mmol). The mixture was stirred at 50° C. overnight. The reaction mixture was cooled to 0° C. and NaBH$_4$ (44 mg, 1.2 mmol) was added. The reaction proceeded for 30 min. DCM-MeOH (9-1) was added. The solids were filtered and washed with DCM-MeOH (9-1). Aq. NH$_4$OH was added and the phases were separated. The aq. layer was extracted with DCM-MeOH (9-1) and the combined org. layers were dried over Na$_2$SO$_4$ and concentrated. The residue was chromatographed (1000:50:4 DCM/MeOH/NH$_4$OH) to afford the title compound as a colourless solid (34 mg, 59% yield).

MS (ESI, m/z): 495.4 [M+H$^+$].

18.ii. trans-(1R*,2R*)-2-amino-2-{4-[(E)-3-(2,5-difluoro-phenyl)-allylamino]-cyclohexyl}-1-(6-methoxy-[1,5]naphthyridin-4-yl)-ethanol To a solution of intermediate 18.i (10 mg, 0.02 mmol) in 1:1 water/dioxane (0.5 mL) was added KOH (4.5 mg, 0.08 mmol). The mixture was heated at 100° C. for 4 h and at 80° C. overnight. Additional KOH (9 mg, 0.16 mmol) was added and stirring was continued at 80° C. for 5 h. Water was added and the mixture was extracted with DCM-MeOH (9:1). The combined org. layers were dried over MgSO$_4$ and concentrated. The residue was chromatographed (1000:100:8 then 1000:200:16 DCM-MeOH—NH$_4$OH) to afford the title compound as a colourless solid (5 mg, 53% yield).

MS (ESI, m/z): 469.0 [M+H$^+$].

Example 19 trans-6-({4-[(1RS)-1-amino-2-(6-methoxy-quinolin-4-yl)-ethyl]-cyclohexylamino}-methyl)-4H-benzo[1,4]oxazin-3-one

19.i. 6-methoxy-quinoline-4-carboxylic acid ethyl ester

To a suspension of 6-methoxy-quinoline-4-carboxylic acid (prepared according to U.S. Pat. No. 5,338,851; 43.8 g, 215.6 mmol) in DMF (215 mL) were added K$_2$CO$_3$ (99%; 60.2 g, 431.2 mmol) and iodoethane (19.4 mL, 237.2 mmol). The mixture was heated at 55° C. overnight. The solvent was evaporated to dryness, and the residue was partitioned between EA (1.5 L) and water (600 mL). The org. layer was washed twice with brine (2×300 mL), dried over Na$_2$SO$_4$, filtered and concentrated to dryness to yield a purple solid (37.5 g).

¹H NMR (d6-DMSO) δ: 8.87 (d, J=4.5 Hz, 1H); 8.05 (d, J=3.0 Hz, 1H); 8.02 (d, J=9.0 Hz, 1H); 7.91 (d, J=4.5 Hz, 1H); 7.49 (dd, J=3.0, 9.0 Hz, 1H); 4.44 (q, J=7.2 Hz, 2H); 3.90 (s, 3H); 1.39 (t, J=7.2 Hz, 3H).
MS (ESI, m/z): 232.4 [M+H⁺].

19.ii. (6-methoxy-quinolin-4-yl)-methanol

To a solution of intermediate 19.i (37.0 g, 160 mmol) in THF (1.4 L) and ethanol (145 mL) was added at rt NaBH₄ (24.7 g, 640 mmol) portionwise. The reaction was stirred for 40 min at rt before heating at 50° C. overnight. The reaction mixture was diluted with water (1 L) and the volatiles were removed in vacuo. The solids were filtered and washed with water (500 mL), then Hept (500 mL). After drying under HV, the title compound was obtained as a pink solid (16.8 g, 55% yield).
MS (ESI, m/z): 190.1 [M+H⁺].

19.iii. 4-bromomethyl-6-methoxy-quinoline

Starting from intermediate 19.ii (16.8 g, 88.8 mmol), the title bromide was obtained as a brown solid (14.54 g, 65% yield) using the procedure of Example 7, step 7.ii.
¹H NMR (d6-DMSO) δ: 8.69 (d, J=4.5 Hz, 1H); 7.96 (d, J=9.0 Hz, 1H); 7.58 (d, J=4.5 Hz, 1H); 7.50 (d, J=3.0 Hz, 1H); 7.43 (dd, J=3.0, 9.0 Hz, 1H); 5.17 (s, 2H); 3.93 (s, 3H).
MS (ESI, m/z): 251.9 [M+H⁺].

19.iv. [(1RS)-1-cis/trans-(4-amino-cyclohexyl)-2-(6-methoxy-quinolin-4-yl)-ethyl]-carbamic acid tert-butyl ester The title compound was obtained as a yellowish foam (0.431 g), starting from intermediate 19.iii (5.04 g, 20 mmol), and using the procedures of Example 7, steps 7.iii to 7.vii [ester alkylation (48% yield), saponification (91% yield), Curtius degradation (41% yield), ketal hydrolysis (quant.) and amine formation (59% yield)]. If necessary, the crude reaction mixtures were purified by chromatography over SiO₂ using an appropriate eluent. The amine was obtained as a cis-trans mixture.
MS (ESI, m/z): 400.5 [M+H⁺].

19.v. (1RS)-(2-(6-methoxy-quinolin-4-yl)-1-cis/trans-{4-[(3-oxo-3,4-dihydro-2H-benzo[1,4]oxazin-6-ylmethyl)-amino]-cyclohexyl}-ethyl)-carbamic acid tert-butyl ester The title compound was obtained as a yellowish solid (0.548 g, 91% yield), starting from intermediate 19.iv (0.431 g, 1.08 mmol) and 3-oxo-3,4-dihydro-2H-benzo[1,4]oxazine-6-carbaldehyde (0.210 g, 1.1 eq.) and using the procedure of Example 1, step 1.xiii. The compound was purified by chromatography (DCM-MeOH 19-1 containing 0.5% aq. NH₄OH).
MS (ESI, m/z): 561.5 [M+H⁺].

19.vi. trans-6-({4-[(1RS)-1-amino-2-(6-methoxy-quinolin-4-yl)-ethyl]-cyclohexylamino}-methyl)-4H-benzo[1,4]oxazin-3-one Starting from intermediate 19.v (0.548 g, 0.98 mmol), the title compound was obtained as an off-white solid (0.23 g, 86% yield) using the procedure of Example 1, step 1.xv. The trans-compound was obtained as a pure isomer after chromatography over SiO₂ (DCM-MeOH 9-1 containing 1% aq. NH₄OH).
¹H NMR (d6-DMSO) δ: 8.59 (d, J=4.5 Hz, 1H); 7.89 (d, J=9.0 Hz, 1H); 7.38-7.29 (m, 3H); 6.88-6.83 (m, 3H); 4.50 (s, 2H); 3.89 (s, 3H); 3.62 (s, 2H); 3.30-3.15 (partially overlapped m, 2H); 2.81 (m, 1H); 2.70 (m, 1H); 2.30 (m, 1H); 1.97-1.84 (m, 3H); 1.73 (m, 1H); 1.88-1.19 (br. s, 3H); 1.25-1.13 (m, 2H); 1.05-0.96 (m, 2H).
MS (ESI, m/z): 461.2 [M+H⁺].

Example 20 trans-6-({4-[(1RS)-amino-2-(6-methoxy-quinolin-4-yl)-ethyl]-cyclohexylamino}-methyl)-4H-pyrido[3,2-b][1,4]thiazin-3-one 20.i. (1RS)-(2-(6-methoxy-quinolin-4-yl)-1-trans-{4-[(3-oxo-3,4-dihydro-2H-pyrido[3,2-b][1,4]thiazin-6-ylmethyl)-amino]-cyclohexyl}-ethyl)-carbamic acid tert-butyl ester Starting from intermediate 19.iv (0.201 g, 0.505 mmol), and 3-oxo-3,4-dihydro-2H-pyrido[3,2-b][1,4]thiazine-6-carbaldehyde (0.114 g, 1.1 eq.), the title compound was obtained as a yellowish foam (0.203 g, 66% yield) using the procedure of Example 1, step 1.xiii. The crude reaction mixture was purified by chromatography over SiO₂ (DCM-MeOH 9-1 containing 1% aq. NH₄OH) to afford the pure trans-isomer. The cis-isomer was discarded.
MS (ESI, m/z): 578.2 [M+H⁺].

20.ii. trans-6-({4-[(1RS)-amino-2-(6-methoxy-quinolin-4-yl)-ethyl]-cyclohexylamino}-methyl)-4H-pyrido[3,2-b][1,4]thiazin-3-one Starting from intermediate 20.i (0.203 g, 0.35 mmol), the title compound was obtained as a yellowish foam (0.118 g, 71% yield) using the procedure of Example 1, step 1.xv. The compound was triturated in ether.
MS (ESI, m/z): 478.2 [M+H⁺].

Example 21 trans-6-({4-[(1RS)-amino-2-(6-methoxy-quinolin-4-yl)-ethyl]-cyclohexylamino}-methyl)-4H-pyrido[3,2-b][1,4]oxazin-3-one 21.i. (2-(6-methoxy-quinolin-4-yl)-1-{4-[(3-oxo-3,4-dihydro-2H-pyrido[3,2-b][1,4]oxazin-6-ylmethyl)-amino]-cyclohexyl}-ethyl)-carbamic acid tert-butyl ester Starting from intermediate 19.iv (0.201 g, 0.505 mmol) and 3-oxo-3,4-dihydro-2H-pyrido[3,2-b][1,4]oxazine-6-carbaldehyde (0.101 g, 1.1 eq.), the title compound was obtained as an off-white solid (0.145 g, 51% yield) using the procedure of Example 1, step 1.xiii. The crude reaction mixture was purified by chromatography over SiO₂ (DCM-MeOH 9-1 containing 1% aq. NH₄OH) to afford the pure trans-isomer. The cis-isomer was discarded.
MS (ESI, m/z): 562.4 [M+H⁺].

21.ii. trans-6-({4-[(1RS)-amino-2-(6-methoxy-quinolin-4-yl)-ethyl]-cyclohexylamino}-methyl)-4H-pyrido[3,2-b][1,4]oxazin-3-one Starting from intermediate 21.i (0.145 g, 0.26 mmol), the title compound was obtained as an off-white solid (0.03 g, 25% yield) using the procedure of Example 1, step 1.xv. The trans-compound was obtained as a pure isomer after chromatography over SiO$_2$ (DCM-MeOH 9-1 containing 1% aq. NH$_4$OH).

MS (ESI, m/z): 462.1 [M+H$^+$].

PHARMACOLOGICAL PROPERTIES OF THE INVENTION COMPOUNDS

In Vitro Assays
Experimental Methods:

These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards: Villanova, Pa., USA, 1997". Minimal inhibitory concentrations (MICs; mg/l) were determined in cation-adjusted Mueller-Hinton Broth (BBL) by a microdilution method following NCCLS guidelines (National Committee for Clinical Laboratory Standards. Methods for Dilution Antimicrobial Susceptibility). The pH of the test medium was 7.2-7.3.

Results:

All Example compounds were tested against a variety of bacteria including *Acetinobacter* and *P. aeruginosa* bacteria.

When tested on the strain *S. aureus* A 798, the compounds of the Examples showed MICs ranging from 0.031 mg/l to 4 mg/l, with a mean value of about 0.4 mg/l. When tested on the strain *P. aeruginosa* A1124, the compounds of the Examples showed MICs ranging from 0.125 mg/l to 2 mg/l, with a mean value of about 0.63 mg/l. When tested on the strain *A. baumanii* T6474, the compounds of the Examples showed MICs ranging from 0.125 mg/l to 32 mg/l, with a mean value of about 11 mg/l.

Typical antibacterial test results are given in the table hereafter (MIC in mg/l).

| Example No. | *S. aureus* A798 | *P. aeruginosa* A1124 | *A. baumanii* T6474 |
|---|---|---|---|
| 1 | 4 | 0.063 | 32 |
| 6 | 0.125 | 0.5 | 16 |
| 11 | 0.5 | 0.125 | 4 |
| 17 | 0.063 | 2 | 16 |

Besides, the following results have been obtained on *S. aureus* A798 (MIC in mg/l):

| Example No. | *S. aureus* A798 |
|---|---|
| 1 | 4 |
| 2 | 0.125 |
| 3 | 0.125 |
| 4 | 0.063 |
| 5 | 0.125 |
| 6 | 0.125 |
| 7 | 0.063 |
| 8 | 1 |
| 9 | 0.5 |
| 10 | 0.031 |
| 11 | 0.5 |
| 12 | ≦0.031 |
| 13 | 0.063 |
| 14 | ≦0.031 |
| 15 | 0.25 |
| 16 | 0.063 |
| 17 | 0.063 |

-continued

| Example No. | *S. aureus* A798 |
|---|---|
| 18 | ≦0.031 |
| 19 | 1 |
| 20 | 0.125 |
| 21 | 0.5 |

The invention claimed is:

1. A compound of formula I

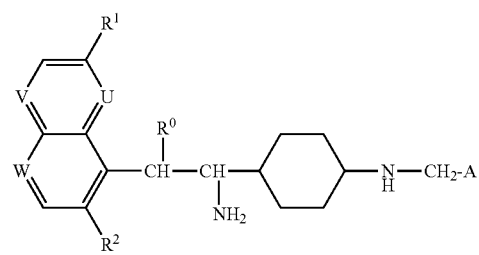

I wherein

R$^0$ represents H or OH;

R$^1$ represents alkoxy;

U and W represent N, V represents CH and R$^2$ represents H or F

A represents the group CH═CH—B or a binuclear heterocyclic system D;

B represents a mono- or di-substituted phenyl group wherein the substituents are halogen atoms;

D represents either the group

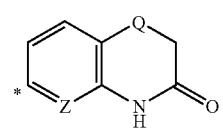

wherein the sign * designates the point of attachment of the group to the rest of the molecule, Z represents CH or N, and Q represents O or S, or the group

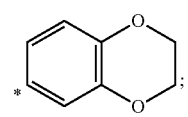

wherein the sign * designates the point of attachment of the group to the rest of the molecule;

or a pharmaceutically acceptable salt of such a compound.

2. A compound of formula I according to claim 1, which is also a compound of formula I$_p$;

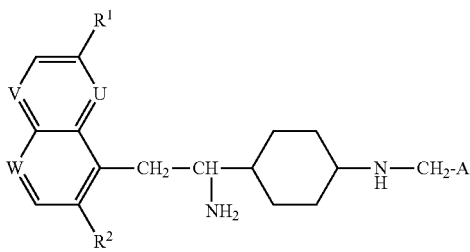

wherein
R¹ represents alkoxy;
U and W represent N, V represents CH and R² represents H or F;
A represents the group CH=CH—B or a binuclear heterocyclic system D;
B represents a mono- or di-substituted phenyl group wherein the substituents are halogen atoms;
D represents the group

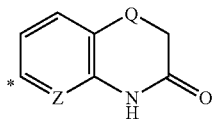

wherein
the sign * designates the point of attachment of the group to the rest of the molecule,
Z represents CH or N, and
Q represents O or S;
or a pharmaceutically acceptable salt of such a compound.

3. A compound of formula I according to claim 1, wherein R¹ represents methoxy;
or a pharmaceutically acceptable salt of such a compound.

4. A compound of formula I according to claim 1, which is:
6-(trans-{4-[(1R)-1-amino-2-(6-methoxy-[1,5]naphthyridin-4-yl)-ethyl]cyclohexylamino}-methyl)-4H-pyrido[3,2-b][1,4]thiazin-3-one;
6-(trans-{4-[(1S)-1-amino-2-(6-methoxy-[1,5]naphthyridin-4-yl)-ethyl]-cyclohexylamino}-methyl)-4H-pyrido[3,2-b][1,4]thiazin-3-one;
6-(trans-{4-[(1R*,2R*)-1-amino-2-hydroxy-2-(6-methoxy-[1,5]naphthyridin-4-yl)-ethyl]-cyclohexylamino}-methyl)-4H-pyrido[3,2-b][1,4]thiazin-3-one;
trans-{4-[1-amino-2-(6-methoxy-[1,5]naphthyridin-4-yl)-ethyl]-cyclohexyl}-[3-(2,5-difluoro-phenyl)-allyl]-amine;
6-(trans-{4-[1-amino-2-(6-methoxy-[1,5]naphthyridin-4-yl)-ethyl]-cyclohexylamino}-methyl)-4H-pyrido[3,2-b][1,4]oxazin-3-one;
trans-6-({4-[1-amino-2-(3-fluoro-6-methoxy-[1,5]naphthyridin-4-yl)-ethyl]-cyclohexylamino}-methyl)-4H-pyrido[3,2-b][1,4]thiazin-3-one;
cis-6-({4-[1-amino-2-(3-fluoro-6-methoxy-[1,5]naphthyridin-4-yl)-ethyl]-cyclohexylamino}-methyl)-4H-pyrido[3,2-b][1,4]thiazin-3-one;
trans-(1R*,2R*)-2-amino-2-{4-[(2,3-dihydro-benzo[1,4]dioxin-6-ylmethyl)-amino]-cyclohexyl}-1-(6-methoxy-[1,5]naphthyridin-4-yl)-ethanol;
trans-(1R*,2R*)-2-amino-2-{4-[(E)-3-(2,5-difluoro-phenyl)-allylamino]-cyclohexyl}-1-(6-methoxy-[1,5]naphthyridin-4-yl)-ethanol;
or a pharmaceutically acceptable salt of one of these compounds.

5. A pharmaceutical composition comprising a compound of formula I as defined in claim 1 or a pharmaceutically acceptable salt thereof, and at least one therapeutically inert excipient.

6. A compound of formula I according to claim 1, wherein A represents the group CH=CH—B wherein B represents a mono- or di-substituted phenyl group wherein the substituents are halogen atoms;
or a pharmaceutically acceptable salt of such a compound.

7. A compound of formula I according to claim 1, wherein A represents the group

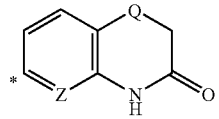

wherein
the sign "*" designates the point of attachment of the group to the rest of the molecule,
Z represents CH or N, and
Q represents O or S;
or a pharmaceutically acceptable salt of such a compound.

8. A compound of formula I according to claim 1, wherein A represents the group

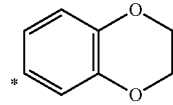

wherein the sign "*" designates the point of attachment of the group to the rest of the molecule;
or a pharmaceutically acceptable salt of such a compound.

* * * * *